(12) United States Patent
Deem et al.

(10) Patent No.: US 12,161,552 B2
(45) Date of Patent: Dec. 10, 2024

(54) HYDRAULIC DELIVERY SYSTEMS FOR PROSTHETIC HEART VALVE DEVICES AND ASSOCIATED METHODS

(71) Applicant: Twelve, Inc., Redwood City, CA (US)

(72) Inventors: Mark Deem, Mountain View, CA (US); Hanson Gifford, III, Woodside, CA (US); John Morriss, San Francisco, CA (US); Matt McLean, San Francisco, CA (US); Michael Luna, San Jose, CA (US)

(73) Assignee: Twelve, Inc., Redwood City, CA (US)

( * ) Notice: Subject to any disclaimer, the term of this patent is extended or adjusted under 35 U.S.C. 154(b) by 304 days.

(21) Appl. No.: 17/485,921

(22) Filed: Sep. 27, 2021

(65) Prior Publication Data

US 2022/0008194 A1 Jan. 13, 2022

Related U.S. Application Data

(60) Continuation of application No. 16/288,679, filed on Feb. 28, 2019, now Pat. No. 11,129,714, which is a continuation of application No. 15/286,623, filed on Oct. 6, 2016, now Pat. No. 10,258,468, which is a
(Continued)

(51) Int. Cl.
*A61F 2/24* (2006.01)
*A61F 2/95* (2013.01)
*A61B 50/30* (2016.01)
*A61F 2/00* (2006.01)

(52) U.S. Cl.
CPC ............ *A61F 2/243* (2013.01); *A61F 2/2436* (2013.01); *A61F 2/95* (2013.01); *A61B 50/30* (2016.02); *A61F 2/0095* (2013.01)

(58) Field of Classification Search
CPC .......... A61F 2/243; A61F 2/2436; A61F 2/95; A61F 2/0095; A61B 50/30
See application file for complete search history.

(56) References Cited

U.S. PATENT DOCUMENTS

| | | |
|---|---|---|
| 3,526,219 A | 9/1970 | Balamuth |
| 3,565,062 A | 2/1971 | Kurtis |
| 3,589,363 A | 6/1971 | Banko et al. |

(Continued)

FOREIGN PATENT DOCUMENTS

| | | |
|---|---|---|
| CN | 1440261 | 6/2005 |
| CN | 101076290 | 11/2007 |

(Continued)

OTHER PUBLICATIONS

US 9,265,606 B2, 02/2016, Buchbinder et al. (withdrawn)
(Continued)

*Primary Examiner* — Richard G Louis
(74) *Attorney, Agent, or Firm* — Medler Ferro Woodhouse & Mills PLLC

(57) ABSTRACT

Systems, apparatuses, and methods for treating native heart valves are disclosed herein. A system for delivering a prosthetic device into a heart of a patient includes an elongated catheter body and a delivery capsule. The delivery capsule can be hydraulically driven to deploy at least a portion of a prosthetic heart valve device. The delivery capsule can release the prosthetic heart valve device at a desired treatment site in a patient.

17 Claims, 63 Drawing Sheets

Related U.S. Application Data division of application No. 13/781,504, filed on Feb. 28, 2013, now Pat. No. 9,579,198.

(60) Provisional application No. 61/760,399, filed on Feb. 4, 2013, provisional application No. 61/605,699, filed on Mar. 1, 2012.

(56) References Cited

U.S. PATENT DOCUMENTS

| | | |
|---|---|---|
| 3,667,474 A | 6/1972 | Lapkin et al. |
| 3,823,717 A | 7/1974 | Pohlman et al. |
| 3,861,391 A | 1/1975 | Antonevich et al. |
| 3,896,811 A | 7/1975 | Storz |
| 4,042,979 A | 8/1977 | Angell |
| 4,188,952 A | 2/1980 | Loschilov et al. |
| 4,282,882 A | 8/1981 | Langham |
| 4,431,006 A | 2/1984 | Trimmer et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Laughlin et al. |
| 4,602,911 A | 7/1986 | Ahmadi et al. |
| 4,646,736 A | 3/1987 | Auth |
| 4,649,922 A | 3/1987 | Wiktor |
| 4,692,139 A | 9/1987 | Stiles |
| 4,747,821 A | 5/1988 | Kensey et al. |
| 4,750,902 A | 6/1988 | Wuchinich et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,986,830 A | 1/1991 | Owens et al. |
| 4,990,134 A | 2/1991 | Auth |
| 5,058,570 A | 10/1991 | Idemoto et al. |
| 5,069,664 A | 12/1991 | Guess et al. |
| 5,076,276 A | 12/1991 | Sakurai et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,344,426 A | 9/1994 | Lau et al. |
| 5,352,199 A | 10/1994 | Tower |
| 5,356,418 A | 10/1994 | Shturman |
| 5,397,293 A | 3/1995 | Alliger |
| 5,411,025 A | 5/1995 | Webster, Jr. |
| 5,411,552 A | 5/1995 | Andersen et al. |
| 5,443,446 A | 8/1995 | Shturman |
| 5,449,373 A | 9/1995 | Pinchasik et al. |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,656,036 A | 8/1997 | Palmaz |
| 5,662,671 A | 9/1997 | Barbut et al. |
| 5,681,336 A | 10/1997 | Clement et al. |
| 5,695,507 A | 12/1997 | Auth et al. |
| 5,725,494 A | 3/1998 | Brisken |
| 5,782,931 A | 7/1998 | Yang et al. |
| 5,817,101 A | 10/1998 | Fiedler |
| 5,827,229 A | 10/1998 | Auth et al. |
| 5,827,321 A | 10/1998 | Roubin et al. |
| 5,840,081 A | 11/1998 | Andersen et al. |
| 5,853,422 A | 12/1998 | Huebsch et al. |
| 5,855,601 A | 1/1999 | Bessler et al. |
| 5,868,781 A | 2/1999 | Killion |
| 5,873,811 A | 2/1999 | Wang et al. |
| 5,904,679 A | 5/1999 | Clayman |
| 5,910,129 A | 6/1999 | Koblish et al. |
| 5,957,882 A | 9/1999 | Nita et al. |
| 5,972,004 A | 10/1999 | Williamson, IV et al. |
| 5,989,208 A | 11/1999 | Nita |
| 5,989,280 A * | 11/1999 | Euteneuer ............ A61M 29/02 623/1.1 |
| 6,047,700 A | 4/2000 | Eggers et al. |
| 6,056,759 A | 5/2000 | Fiedler |
| 6,085,754 A | 7/2000 | Alferness et al. |
| 6,113,608 A * | 9/2000 | Monroe ................ A61F 2/966 623/1.11 |
| RE36,939 E | 10/2000 | Tachibana et al. |
| 6,129,734 A | 10/2000 | Shturman et al. |
| 6,132,444 A | 10/2000 | Shturman et al. |
| 6,159,139 A | 12/2000 | Chiu |
| 6,168,579 B1 | 1/2001 | Tsugita |
| 6,217,595 B1 | 4/2001 | Shturman et al. |
| 6,254,635 B1 | 7/2001 | Schroeder et al. |
| 6,295,712 B1 | 10/2001 | Shturman et al. |
| 6,306,414 B1 | 10/2001 | Koike |
| 6,321,109 B2 | 11/2001 | Ben-Haim et al. |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |
| 6,494,891 B1 | 12/2002 | Cornish et al. |
| 6,505,080 B1 | 1/2003 | Sutton |
| 6,514,261 B1 | 2/2003 | Randall et al. |
| 6,530,952 B2 | 3/2003 | Vesely |
| 6,540,782 B1 | 4/2003 | Snyders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,460 B1 | 6/2003 | Cryer |
| 6,582,462 B1 | 6/2003 | Andersen et al. |
| 6,595,912 B2 | 7/2003 | Lau et al. |
| 6,605,109 B2 | 8/2003 | Fiedler |
| 6,616,689 B1 | 9/2003 | Ainsworth et al. |
| 6,623,452 B2 | 9/2003 | Chien et al. |
| 6,638,288 B1 | 10/2003 | Shturman et al. |
| 6,648,854 B1 | 11/2003 | Patterson et al. |
| 6,689,086 B1 | 2/2004 | Nita et al. |
| 6,702,748 B1 | 3/2004 | Nita et al. |
| 6,730,121 B2 | 5/2004 | Ortiz et al. |
| 6,746,463 B1 | 6/2004 | Schwartz |
| 6,811,801 B2 | 11/2004 | Nguyen et al. |
| 6,818,001 B2 | 11/2004 | Wulfman et al. |
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |
| 6,986,775 B2 | 1/2006 | Morales et al. |
| 7,018,404 B2 | 3/2006 | Holmberg et al. |
| 7,052,487 B2 | 5/2006 | Cohn et al. |
| 7,077,861 B2 | 7/2006 | Spence |
| 7,125,420 B2 | 10/2006 | Rourke et al. |
| 7,163,552 B2 | 1/2007 | Diaz |
| 7,186,264 B2 | 3/2007 | Liddicoat et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |

(56) References Cited

U.S. PATENT DOCUMENTS

| | | |
|---|---|---|
| 7,442,204 B2 | 10/2008 | Schwammenthal et al. |
| 7,473,275 B2 | 1/2009 | Marquez |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |
| 7,942,928 B2 | 5/2011 | Webler et al. |
| 7,985,238 B2 | 7/2011 | Balgobin et al. |
| 8,002,826 B2 | 8/2011 | Seguin |
| 8,052,750 B2 | 11/2011 | Tuval et al. |
| 8,062,355 B2 | 11/2011 | Figulla et al. |
| 8,109,996 B2 | 2/2012 | Stacchino et al. |
| 8,114,154 B2 | 2/2012 | Righini et al. |
| 8,252,051 B2 | 8/2012 | Chau et al. |
| 8,398,704 B2 | 3/2013 | Straubinger et al. |
| 8,403,981 B2 | 3/2013 | Forster et al. |
| 8,403,983 B2 | 3/2013 | Quadri et al. |
| 8,414,643 B2 | 4/2013 | Tuval et al. |
| 8,449,599 B2 | 5/2013 | Chau et al. |
| 8,496,671 B1 | 7/2013 | Hausen |
| 8,512,252 B2 | 8/2013 | Ludomirsky et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,540,767 B2 | 9/2013 | Zhang |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Seguin et al. |
| 8,634,935 B2 | 1/2014 | Gaudiani |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guehring et al. |
| 8,715,160 B2 | 5/2014 | Raman et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Rahdert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,812,431 B2 | 8/2014 | Voigt et al. |
| 8,828,043 B2 | 9/2014 | Chambers |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,514 B2 | 10/2014 | Crooke et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,894,702 B2 | 11/2014 | Quadri et al. |
| 8,900,214 B2 | 12/2014 | Nance et al. |
| 8,900,295 B2 | 12/2014 | Migliazza et al. |
| 8,920,411 B2 | 12/2014 | Gelbart et al. |
| 8,926,694 B2 | 1/2015 | Costello |
| 8,932,348 B2 | 1/2015 | Solem et al. |
| 8,936,027 B2 | 1/2015 | Santamore et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,023,101 B2 | 5/2015 | Krahbichler |
| 9,050,188 B2 | 6/2015 | Schweich, Jr. et al. |
| 9,066,800 B2 | 6/2015 | Clague et al. |
| 9,084,676 B2 | 7/2015 | Chau et al. |
| 9,095,433 B2 | 8/2015 | Lutter et al. |
| 9,119,713 B2 | 9/2015 | Board et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,180,005 B1 | 11/2015 | Lashinski et al. |
| 9,192,466 B2 | 11/2015 | Kowalsky et al. |
| 9,192,471 B2 | 11/2015 | Bolling |
| 9,226,825 B2 | 1/2016 | Starksen et al. |
| 9,232,942 B2 | 1/2016 | Seguin et al. |
| 9,232,998 B2 | 1/2016 | Wilson et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,254,192 B2 | 2/2016 | Lutter et al. |
| 9,259,317 B2 | 2/2016 | Wilson et al. |
| 9,271,833 B2 | 3/2016 | Kim et al. |
| 9,289,291 B2 | 3/2016 | Gorman, III et al. |
| 9,289,297 B2 | 3/2016 | Wilson et al. |
| 9,289,927 B2 | 3/2016 | Weber et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,326,852 B2 | 5/2016 | Spenser |
| 9,333,073 B2 | 5/2016 | Quadri et al. |
| 9,333,074 B2 | 5/2016 | Quadri et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,108 B2 | 6/2016 | Boertlein et al. |
| 9,387,075 B2 | 7/2016 | Boertlein et al. |
| 9,387,078 B2 | 7/2016 | Gross et al. |
| 9,393,111 B2 | 7/2016 | Ma et al. |
| 9,425,916 B2 | 8/2016 | Nakao et al. |
| 9,579,198 B2 | 2/2017 | Deem et al. |
| 9,629,719 B2 | 4/2017 | Rothstein |

(56) References Cited

U.S. PATENT DOCUMENTS

| | | |
|---|---|---|
| 9,675,454 B2 | 6/2017 | Vidlund et al. |
| 9,681,951 B2 | 6/2017 | Ratz et al. |
| 9,687,342 B2 | 6/2017 | Figulla et al. |
| 9,687,343 B2 | 6/2017 | Boertlein et al. |
| 9,693,859 B2 | 7/2017 | Braido et al. |
| 9,693,862 B2 | 7/2017 | Campbell et al. |
| 9,694,121 B2 | 7/2017 | Alexander et al. |
| 9,700,409 B2 | 7/2017 | Braido et al. |
| 9,700,411 B2 | 7/2017 | Klima et al. |
| 9,730,791 B2 | 8/2017 | Ratz et al. |
| 9,730,794 B2 | 8/2017 | Carpentier et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |
| 9,763,658 B2 | 9/2017 | Eigler et al. |
| 9,763,782 B2 | 9/2017 | Solem |
| 9,770,328 B2 | 9/2017 | Macoviak |
| 9,788,931 B2 | 10/2017 | Giordano et al. |
| 9,801,717 B2 | 10/2017 | Edquist et al. |
| 9,827,092 B2 | 11/2017 | Vidlund et al. |
| 9,827,101 B2 | 11/2017 | Solem et al. |
| 9,833,313 B2 | 12/2017 | Board et al. |
| 9,833,315 B2 | 12/2017 | Vidlund et al. |
| 9,839,511 B2 | 12/2017 | Ma et al. |
| 9,844,435 B2 | 12/2017 | Eidenschink |
| 9,848,880 B2 | 12/2017 | Coleman et al. |
| 9,848,983 B2 | 12/2017 | Lashinski et al. |
| 9,861,477 B2 | 1/2018 | Backus et al. |
| 9,861,480 B2 | 1/2018 | Zakai et al. |
| 9,968,453 B2 | 5/2018 | Vola et al. |
| 10,258,468 B2 | 4/2019 | Deem et al. |
| 10,433,961 B2 | 10/2019 | McLean |
| 10,575,950 B2 | 3/2020 | McLean |
| 10,646,338 B2 | 5/2020 | Mauch et al. |
| 2001/0021872 A1 | 9/2001 | Bailey et al. |
| 2001/0049492 A1 | 12/2001 | Frazier et al. |
| 2002/0007219 A1 | 1/2002 | Merrill et al. |
| 2002/0013571 A1 | 1/2002 | Goldfarb et al. |
| 2002/0045929 A1* | 4/2002 | Diaz ............... A61F 2/966 623/1.11 |
| 2002/0072792 A1 | 6/2002 | Burgermeister et al. |
| 2002/0077627 A1 | 6/2002 | Johnson et al. |
| 2002/0082637 A1 | 6/2002 | Lumauig |
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0106989 A1 | 6/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0186558 A1 | 9/2004 | Pavcnik et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |
| 2005/0075720 A1 | 4/2005 | Nguyen et al. |
| 2005/0075727 A1 | 4/2005 | Wheatley |
| 2005/0096647 A1 | 5/2005 | Steinke et al. |
| 2005/0107661 A1 | 5/2005 | Lau et al. |
| 2005/0137682 A1 | 6/2005 | Justino |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0267523 A1 | 12/2005 | Devellian et al. |
| 2006/0058872 A1 | 3/2006 | Salahieh et al. |
| 2006/0106456 A9 | 5/2006 | Machold et al. |
| 2006/0142833 A1 | 6/2006 | Von Oepen et al. |
| 2006/0149360 A1 | 7/2006 | Schwammenthal et al. |
| 2006/0167543 A1 | 7/2006 | Bailey et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0056346 A1 | 3/2007 | Spenser et al. |
| 2007/0061010 A1 | 3/2007 | Hauser et al. |
| 2007/0073391 A1 | 3/2007 | Bourang et al. |
| 2007/0088431 A1 | 4/2007 | Bourang et al. |
| 2007/0135826 A1 | 6/2007 | Zaver et al. |
| 2007/0142906 A1 | 6/2007 | Figulla et al. |
| 2007/0173932 A1 | 7/2007 | Cali et al. |
| 2007/0203561 A1 | 8/2007 | Forster et al. |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2008/0243246 A1 | 10/2008 | Ryan et al. |
| 2009/0024137 A1 | 1/2009 | Chuter et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0105794 A1* | 4/2009 | Ziarno ............... A61F 2/2436 600/481 |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023117 A1 | 1/2010 | Yoganathan et al. |
| 2010/0030330 A1 | 2/2010 | Bobo et al. |
| 2010/0035703 A1 | 2/2010 | Ishikawa et al. |
| 2010/0049313 A1 | 2/2010 | Alon et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0160931 A1 | 6/2010 | Karpiel et al. |
| 2010/0185275 A1 | 7/2010 | Richter et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0286768 A1 | 11/2010 | Alkhatib et al. |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |

(56) References Cited

U.S. PATENT DOCUMENTS

| | | |
|---|---|---|
| 2011/0029071 A1 | 2/2011 | Zlotnick et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0201874 A1 | 8/2011 | Birk et al. |
| 2011/0208293 A1 | 8/2011 | Tabor |
| 2011/0224785 A1 | 9/2011 | Hacohen |
| 2011/0251681 A1 | 10/2011 | Shipley et al. |
| 2011/0264203 A1 | 10/2011 | Dwork et al. |
| 2011/0319988 A1 | 12/2011 | Schankereli et al. |
| 2012/0022639 A1 | 1/2012 | Hacohen |
| 2012/0035703 A1 | 2/2012 | Lutter et al. |
| 2012/0035713 A1 | 2/2012 | Lutter et al. |
| 2012/0053680 A1 | 3/2012 | Bolling et al. |
| 2012/0053682 A1 | 3/2012 | Kowalsky et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2013/0035628 A1 | 2/2013 | Garrison et al. |
| 2013/0138090 A1 | 5/2013 | Fargahi |
| 2013/0172978 A1 | 7/2013 | Vidlund et al. |
| 2013/0190860 A1 | 7/2013 | Sundt, III |
| 2013/0190861 A1 | 7/2013 | Chau et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guehring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0274870 A1* | 10/2013 | Lombardi ............ A61F 2/2418 623/2.11 |
| 2013/0282059 A1 | 10/2013 | Ketai et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304180 A1 | 11/2013 | Green et al. |
| 2013/0304181 A1 | 11/2013 | Green et al. |
| 2013/0304197 A1 | 11/2013 | Buchbnder et al. |
| 2013/0304198 A1 | 11/2013 | Solem |
| 2013/0304200 A1 | 11/2013 | McLean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | McLean et al. |
| 2013/0204358 A1 | 12/2013 | Matheny |
| 2013/0325110 A1 | 12/2013 | Khalil et al. |
| 2013/0325114 A1 | 12/2013 | McLean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0345715 A1 | 12/2013 | Gifford et al. |
| 2013/0345797 A1 | 12/2013 | Dahlgren et al. |
| 2013/0345803 A1 | 12/2013 | Bergheim, III |
| 2014/0005778 A1 | 1/2014 | Buchbnder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Joensson et al. |
| 2014/0172084 A1 | 6/2014 | Callas et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |
| 2014/0194969 A1 | 7/2014 | Headley |
| 2014/0194976 A1 | 7/2014 | Starksen et al. |
| 2014/0200397 A1 | 7/2014 | Raman et al. |
| 2014/0200649 A1 | 7/2014 | Essinger et al. |
| 2014/0200657 A1 | 7/2014 | Maurer et al. |
| 2014/0200662 A1 | 7/2014 | Eftel et al. |
| 2014/0214159 A1 | 7/2014 | Vidlund et al. |
| 2014/0172085 A1 | 8/2014 | Quadri et al. |
| 2014/0219524 A1 | 8/2014 | Takeguchi et al. |
| 2014/0222040 A1 | 8/2014 | Park et al. |
| 2014/0222135 A1 | 8/2014 | Forster et al. |
| 2014/0222138 A1 | 8/2014 | Machold et al. |
| 2014/0225942 A1 | 8/2014 | Liu |
| 2014/0225946 A1 | 8/2014 | Quinn et al. |
| 2014/0228942 A1 | 8/2014 | Krahbichler et al. |
| 2014/0228946 A1 | 8/2014 | Chau et al. |
| 2014/0242056 A1 | 8/2014 | Karandikar et al. |
| 2014/0242086 A1 | 8/2014 | Lal et al. |
| 2014/0243560 A1 | 8/2014 | Lorenz et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |

(56) References Cited

U.S. PATENT DOCUMENTS

| | | |
|---|---|---|
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Börtlein et al. |
| 2014/0277410 A1 | 9/2014 | Börtlein et al. |
| 2014/0277411 A1 | 9/2014 | Börtlein et al. |
| 2014/0277412 A1 | 9/2014 | Börtlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lamelas et al. |
| 2014/0309730 A1 | 10/2014 | Alon et al. |
| 2014/0309731 A1 | 10/2014 | Quadri et al. |
| 2014/0309732 A1 | 10/2014 | Solem |
| 2014/0316516 A1 | 10/2014 | Vidlund et al. |
| 2014/0323448 A1 | 10/2014 | Kim et al. |
| 2014/0324164 A1 | 10/2014 | Gross |
| 2014/0330111 A1 | 11/2014 | Lichtenstein et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371843 A1 | 12/2014 | Wilson et al. |
| 2014/0371844 A1 | 12/2014 | Dale et al. |
| 2014/0371846 A1 | 12/2014 | Wilson et al. |
| 2014/0378464 A1 | 12/2014 | Oslob et al. |
| 2014/0378491 A1 | 12/2014 | Oslob et al. |
| 2014/0379074 A1 | 12/2014 | Spence et al. |
| 2014/0379076 A1 | 12/2014 | Vidlund et al. |
| 2015/0004165 A1 | 1/2015 | Yue et al. |
| 2015/0005874 A1 | 1/2015 | Vidlund et al. |
| 2015/0005875 A1 | 1/2015 | Tuval et al. |
| 2015/0012069 A1 | 1/2015 | Puskas |
| 2015/0018353 A1 | 1/2015 | Kim et al. |
| 2015/0018940 A1 | 1/2015 | Quill et al. |
| 2015/0025311 A1 | 1/2015 | Kadan et al. |
| 2015/0025623 A1 | 1/2015 | Granada et al. |
| 2015/0032127 A1 | 1/2015 | Gammie et al. |
| 2015/0032204 A1 | 1/2015 | Johansson |
| 2015/0045878 A1 | 2/2015 | Rowe |
| 2015/0057738 A1 | 2/2015 | Hepke et al. |
| 2015/0066138 A1 | 3/2015 | Alexander et al. |
| 2015/0066140 A1 | 3/2015 | Quadri et al. |
| 2015/0094802 A1 | 4/2015 | Buchbinder et al. |
| 2015/0094803 A1 | 4/2015 | Navia |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |
| 2015/0134055 A1 | 5/2015 | Spence et al. |
| 2015/0139911 A1 | 5/2015 | Santamore et al. |
| 2015/0141855 A1 | 5/2015 | Inoue |
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | Macoviak et al. |
| 2015/0164637 A1 | 6/2015 | Khairkhahan et al. |
| 2015/0164639 A1 | 6/2015 | Starksen et al. |
| 2015/0164641 A1 | 6/2015 | Annest |
| 2015/0173897 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0238314 A1 | 8/2015 | Börtlein et al. |
| 2015/0238729 A1 | 8/2015 | Jenson et al. |
| 2015/0250590 A1 | 9/2015 | Gries et al. |
| 2015/0257877 A1 | 9/2015 | Hernandez |
| 2015/0257878 A1 | 9/2015 | Lane et al. |
| 2015/0257879 A1 | 9/2015 | Börtlein et al. |
| 2015/0257881 A1 | 9/2015 | Börtlein et al. |
| 2015/0257882 A1 | 9/2015 | Börtlein et al. |
| 2015/0272734 A1 | 10/2015 | Sheps et al. |
| 2015/0272737 A1 | 10/2015 | Dale et al. |
| 2015/0305861 A1 | 10/2015 | Annest |
| 2015/0305864 A1 | 10/2015 | Quadri et al. |
| 2015/0313739 A1 | 11/2015 | Hummen et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0342733 A1 | 12/2015 | Alkhatib et al. |
| 2015/0351906 A1 | 12/2015 | Hammer et al. |
| 2015/0351908 A1 | 12/2015 | Keraenen et al. |
| 2015/0359628 A1 | 12/2015 | Keraenen |
| 2015/0359629 A1 | 12/2015 | Ganesan et al. |
| 2015/0359631 A1 | 12/2015 | Sheahan et al. |
| 2015/0366666 A1 | 12/2015 | Khairkhahan et al. |
| 2015/0374495 A1 | 12/2015 | Ruyra Baliarda et al. |
| 2016/0000562 A1 | 1/2016 | Siegel |
| 2016/0000564 A1 | 1/2016 | Buchbinder |
| 2016/0000983 A1 | 1/2016 | Mohl et al. |
| 2016/0008129 A1 | 1/2016 | Siegel |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0030171 A1 | 2/2016 | Quijano et al. |
| 2016/0038246 A1 | 2/2016 | Wang et al. |
| 2016/0038280 A1 | 2/2016 | Morriss et al. |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113764 A1 | 4/2016 | Sheahan et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158002 A1 | 6/2016 | Wallace et al. |
| 2016/0158003 A1 | 6/2016 | Wallace et al. |
| 2016/0184095 A1 | 6/2016 | Spence et al. |
| 2016/0206280 A1 | 7/2016 | Vidlund et al. |
| 2016/0206424 A1 | 7/2016 | Al-Jilaihawi et al. |
| 2016/0262881 A1 | 9/2016 | Schankereli et al. |
| 2016/0158001 A1 | 11/2016 | Wallace et al. |
| 2016/0317290 A1 | 11/2016 | Chau et al. |
| 2017/0079790 A1 | 3/2017 | Vidlund et al. |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |

(56) References Cited

U.S. PATENT DOCUMENTS

| | | | |
|---|---|---|---|
| 2017/0128205 A1 | 5/2017 | Tamir et al. |
| 2017/0128206 A1 | 5/2017 | Rafiee |
| 2017/0128208 A1 | 5/2017 | Christianson et al. |
| 2017/0156860 A1 | 6/2017 | Lashinski |
| 2017/0165054 A1 | 6/2017 | Benson et al. |
| 2017/0165055 A1 | 6/2017 | Hauser et al. |
| 2017/0165064 A1 | 6/2017 | Nyuli et al. |
| 2017/0172737 A1 | 6/2017 | Kuetting |
| 2017/0181851 A1 | 6/2017 | Annest |
| 2017/0189177 A1 | 7/2017 | Schweich, Jr. et al. |
| 2017/0189179 A1 | 7/2017 | Ratz et al. |
| 2017/0189180 A1 | 7/2017 | Alkhatib |
| 2017/0189181 A1 | 7/2017 | Alkhatib et al. |
| 2017/0196688 A1 | 7/2017 | Christianson et al. |
| 2017/0231762 A1 | 8/2017 | Quadri et al. |
| 2017/0231763 A1 | 8/2017 | Yellin |
| 2017/0258585 A1 | 9/2017 | Marquez et al. |
| 2017/0266001 A1 | 9/2017 | Vidlund et al. |
| 2017/0281345 A1 | 10/2017 | Yang et al. |
| 2017/0290659 A1 | 10/2017 | Ulmer et al. |
| 2017/0296338 A1 | 10/2017 | Campbell et al. |
| 2017/0296339 A1 | 10/2017 | Thambar et al. |
| 2017/0319333 A1 | 11/2017 | Tegels et al. |
| 2017/0325842 A1 | 11/2017 | Siegel |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0325949 A1 | 11/2017 | Rodgers et al. |
| 2017/0325953 A1 | 11/2017 | Klima et al. |
| 2017/0325954 A1 | 11/2017 | Perszyk |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348097 A1 | 12/2017 | Taft et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinski et al. |
| 2017/0360558 A1 | 12/2017 | Ma |
| 2017/0360585 A1 | 12/2017 | White |
| 2017/0361065 A1 | 12/2017 | Legaspi et al. |
| 2018/0296325 A1 | 10/2018 | McLean |
| 2018/0344454 A1 | 12/2018 | Mauch et al. |
| 2020/0155305 A1 | 5/2020 | McLean |

FOREIGN PATENT DOCUMENTS

| | | |
|---|---|---|
| CN | 101291637 | 10/2008 |
| CN | 102196784 A | 9/2011 |
| CN | 103491900 | 3/2017 |
| DE | 19605042 | 1/1998 |
| DE | 102006052564 | 12/2007 |
| EP | 0875216 B1 | 7/2003 |
| EP | 1512383 | 3/2005 |
| EP | 1545371 | 6/2005 |
| EP | 1551274 | 7/2005 |
| EP | 1629794 | 3/2006 |
| EP | 1646332 | 4/2006 |
| EP | 1702247 | 9/2006 |
| EP | 1734903 | 12/2006 |
| EP | 186104 | 2/2008 |
| EP | 1891914 | 2/2008 |
| EP | 2010103 | 1/2009 |
| EP | 2026280 | 2/2009 |
| EP | 2037829 | 3/2009 |
| EP | 2081519 | 7/2009 |
| EP | 2111190 | 10/2009 |
| EP | 2142143 | 1/2010 |
| EP | 2167742 | 3/2010 |
| EP | 2203124 | 7/2010 |
| EP | 2278944 | 2/2011 |
| EP | 2306821 | 4/2011 |
| EP | 2327429 | 6/2011 |
| EP | 2400924 | 1/2012 |
| EP | 2400926 | 1/2012 |
| EP | 2410947 | 2/2012 |
| EP | 2416739 | 2/2012 |
| EP | 2419050 | 2/2012 |
| EP | 2444031 | 4/2012 |
| EP | 2470119 | 7/2012 |
| EP | 2488126 | 8/2012 |
| EP | 2509263 | 10/2012 |
| EP | 2509538 | 10/2012 |
| EP | 2510620 | 10/2012 |
| EP | 2522307 | 11/2012 |
| EP | 2549955 | 1/2013 |
| EP | 2549956 | 1/2013 |
| EP | 2566416 | 3/2013 |
| EP | 2586492 | 5/2013 |
| EP | 2611389 | 7/2013 |
| EP | 2618784 | 7/2013 |
| EP | 2623068 | 8/2013 |
| EP | 2626012 | 8/2013 |
| EP | 2626013 | 8/2013 |
| EP | 2629699 | 8/2013 |
| EP | 2633457 | 9/2013 |
| EP | 2637659 | 9/2013 |
| EP | 2641569 | 9/2013 |
| EP | 2644158 | 10/2013 |
| EP | 2654624 | 10/2013 |
| EP | 2656794 | 10/2013 |
| EP | 2656795 | 10/2013 |
| EP | 2656796 | 10/2013 |
| EP | 2667823 | 12/2013 |
| EP | 2670358 | 12/2013 |
| EP | 2676640 | 12/2013 |
| EP | 2688041 | 1/2014 |
| EP | 2693984 | 2/2014 |
| EP | 2697721 | 2/2014 |
| EP | 2713953 | 4/2014 |
| EP | 2714068 | 4/2014 |
| EP | 2717803 | 4/2014 |
| EP | 2723272 | 4/2014 |
| EP | 2723273 | 4/2014 |
| EP | 2723277 | 4/2014 |
| EP | 2739214 | 6/2014 |
| EP | 2741711 | 6/2014 |
| EP | 2750630 | 7/2014 |
| EP | 2750631 | 7/2014 |
| EP | 2755562 | 7/2014 |
| EP | 2755602 | 7/2014 |
| EP | 2757962 | 7/2014 |
| EP | 2760375 | 8/2014 |
| EP | 2777616 | 9/2014 |
| EP | 2777617 | 9/2014 |
| EP | 2782523 | 10/2014 |
| EP | 2785282 | 10/2014 |
| EP | 2786817 | 10/2014 |
| EP | 2790609 | 10/2014 |
| EP | 2793751 | 10/2014 |
| EP | 2797915 | 11/2014 |
| EP | 2800063 | 11/2014 |
| EP | 2809263 | 12/2014 |
| EP | 2810620 | 12/2014 |
| EP | 2811939 | 12/2014 |
| EP | 2814428 | 12/2014 |
| EP | 2814429 | 12/2014 |
| EP | 2819617 | 1/2015 |
| EP | 2819618 | 1/2015 |
| EP | 2819619 | 1/2015 |
| EP | 2822473 | 1/2015 |
| EP | 2833836 | 2/2015 |
| EP | 2838475 | 2/2015 |
| EP | 2839815 | 2/2015 |
| EP | 2844190 | 3/2015 |
| EP | 2849680 | 3/2015 |
| EP | 2849681 | 3/2015 |
| EP | 2852354 | 4/2015 |
| EP | 2854719 | 4/2015 |
| EP | 2870933 | 5/2015 |
| EP | 2873011 | 5/2015 |

(56) References Cited

FOREIGN PATENT DOCUMENTS

| | | |
|---|---|---|
| EP | 2875797 | 5/2015 |
| EP | 2882374 | 6/2015 |
| EP | 2886082 | 6/2015 |
| EP | 2886083 | 6/2015 |
| EP | 2886084 | 6/2015 |
| EP | 2895111 | 7/2015 |
| EP | 2901966 | 8/2015 |
| EP | 2907479 | 8/2015 |
| EP | 2911594 | 9/2015 |
| EP | 2945572 | 11/2015 |
| EP | 2948094 | 12/2015 |
| EP | 2948102 | 12/2015 |
| EP | 2964152 | 1/2016 |
| EP | 2967847 | 1/2016 |
| EP | 2967859 | 1/2016 |
| EP | 2967860 | 1/2016 |
| EP | 2967866 | 1/2016 |
| EP | 2968847 | 1/2016 |
| EP | 2976043 | 1/2016 |
| EP | 2981208 | 2/2016 |
| EP | 2982336 | 2/2016 |
| EP | 2999433 | 3/2016 |
| EP | 2999436 | 3/2016 |
| EP | 3003187 | 4/2016 |
| EP | 3003219 | 4/2016 |
| EP | 3003220 | 4/2016 |
| EP | 3010447 | 4/2016 |
| EP | 3013281 | 5/2016 |
| EP | 3017792 | 5/2016 |
| EP | 3021792 | 5/2016 |
| EP | 3023117 | 5/2016 |
| EP | 3027143 | 6/2016 |
| EP | 3027144 | 6/2016 |
| EP | 3033048 | 6/2016 |
| EP | 3037064 | 6/2016 |
| EP | 3079633 | 10/2016 |
| EP | 3082656 | 10/2016 |
| EP | 3110368 | 1/2017 |
| EP | 3110369 | 1/2017 |
| EP | 3132773 | 2/2017 |
| EP | 3184081 | 6/2017 |
| EP | 3191027 | 7/2017 |
| EP | 3206628 | 8/2017 |
| EP | 3223751 | 10/2017 |
| EP | 3229736 | 10/2017 |
| EP | 3245980 | 11/2017 |
| EP | 3250154 | 12/2017 |
| EP | 3256074 | 12/2017 |
| EP | 3256077 | 12/2017 |
| EP | 3258883 | 12/2017 |
| EP | 3270825 | 1/2018 |
| EP | 3273910 | 1/2018 |
| JP | 2002509756 | 4/2002 |
| JP | 2005280917 | 10/2005 |
| JP | H10258124 | 5/2006 |
| JP | 2008528117 | 7/2008 |
| JP | 2008541863 | 11/2008 |
| JP | 2009195712 | 9/2009 |
| JP | 2010518947 | 6/2010 |
| JP | 2010523534 A | 7/2010 |
| JP | 2012500665 A | 1/2012 |
| JP | 2012523894 A | 10/2012 |
| JP | 5219518 | 6/2013 |
| JP | 6504516 | 5/2016 |
| WO | WO 1992017118 | 10/1992 |
| WO | WO 1995011055 | 4/1995 |
| WO | WO 1995016407 | 6/1995 |
| WO | WO 1999004730 | 2/1999 |
| WO | WO 1999039648 | 8/1999 |
| WO | WO 1999049799 | 10/1999 |
| WO | WO 2001010343 | 2/2001 |
| WO | WO 2002003892 | 1/2002 |
| WO | WO 2002028421 | 4/2002 |
| WO | WO 2002039908 | 5/2002 |
| WO | WO 2003043685 | 5/2003 |
| WO | WO 2004084746 | 10/2004 |
| WO | WO 2004093728 | 11/2004 |
| WO | WO 2004096097 | 11/2004 |
| WO | WO 2004112657 | 12/2004 |
| WO | WO 2005002466 | 1/2005 |
| WO | WO 2005007219 | 1/2005 |
| WO | WO 2005009285 | 2/2005 |
| WO | WO 2005009506 | 2/2005 |
| WO | WO 2005087140 | 9/2005 |
| WO | WO 2006041877 | 4/2006 |
| WO | WO 2006063199 | 6/2006 |
| WO | WO 2007008371 | 1/2007 |
| WO | WO 2007067820 | 6/2007 |
| WO | WO 2007098232 | 8/2007 |
| WO | WO 2008022077 | 2/2008 |
| WO | WO 2008028569 | 3/2008 |
| WO | WO 2008035337 | 3/2008 |
| WO | WO 2008046593 | 4/2008 |
| WO | WO 2008103497 | 8/2008 |
| WO | WO 2008103722 | 8/2008 |
| WO | 2008125153 A1 | 10/2008 |
| WO | WO 2008129405 | 10/2008 |
| WO | WO 2009045338 | 4/2009 |
| WO | WO 2009091509 | 7/2009 |
| WO | WO 2010006627 | 1/2010 |
| WO | WO 2010008549 | 1/2010 |
| WO | WO 2010022138 | 2/2010 |
| WO | WO 2010057262 | 5/2010 |
| WO | WO 2010080594 | 7/2010 |
| WO | WO 2010098857 | 9/2010 |
| WO | WO 2010099032 | 9/2010 |
| WO | WO 2010117680 | 10/2010 |
| WO | WO 2010121076 | 10/2010 |
| WO | WO 2011025981 | 3/2011 |
| WO | WO 2011047168 | 4/2011 |
| WO | WO 2011051043 | 5/2011 |
| WO | WO 2011057087 | 5/2011 |
| WO | WO 2011072084 | 6/2011 |
| WO | WO 2011106137 | 9/2011 |
| WO | WO 2011106544 | 9/2011 |
| WO | WO 2011111047 | 9/2011 |
| WO | WO 2011137531 | 11/2011 |
| WO | WO 2011139747 | 11/2011 |
| WO | WO 2012011018 | 1/2012 |
| WO | WO 2012011108 | 1/2012 |
| WO | WO 2012027487 | 3/2012 |
| WO | WO 2012035279 | 3/2012 |
| WO | WO 2012038550 | 3/2012 |
| WO | WO 2012040655 | 3/2012 |
| WO | WO 2012047644 | 4/2012 |
| WO | WO 2012052718 | 4/2012 |
| WO | WO 2012055498 | 5/2012 |
| WO | WO 2012087842 | 6/2012 |
| WO | WO 2012095455 | 7/2012 |
| WO | WO 2012102928 | 8/2012 |
| WO | WO 2012106602 | 8/2012 |
| WO | WO 2012118508 | 9/2012 |
| WO | WO 2012118816 | 9/2012 |
| WO | WO 2012118894 | 9/2012 |
| WO | WO 2012177942 | 12/2012 |
| WO | WO 2013021374 | 2/2013 |
| WO | WO 2013021375 | 2/2013 |
| WO | WO 2013028387 | 2/2013 |
| WO | WO 2013059743 | 4/2013 |
| WO | WO 2013059747 | 4/2013 |
| WO | WO 2013114214 | 8/2013 |
| WO | WO 2013120181 | 8/2013 |
| WO | WO 2013123059 | 8/2013 |
| WO | WO 2013128432 | 9/2013 |
| WO | WO 2013130641 | 9/2013 |
| WO | WO 2013131925 | 9/2013 |
| WO | WO 2013140318 | 9/2013 |
| WO | WO 2013148017 | 10/2013 |
| WO | WO 2013148018 | 10/2013 |
| WO | WO 2013148019 | 10/2013 |
| WO | WO 2013150512 | 10/2013 |
| WO | WO 2013152161 | 10/2013 |
| WO | WO 2013158613 | 10/2013 |
| WO | WO 2013169448 | 11/2013 |

(56) References Cited

FOREIGN PATENT DOCUMENTS

| | | |
|---|---|---|
| WO | WO 2013175468 | 11/2013 |
| WO | WO 2013176583 | 11/2013 |
| WO | WO 2013188077 | 12/2013 |
| WO | WO 2013192107 | 12/2013 |
| WO | WO 2014010169 | 1/2014 |
| WO | WO 2014036113 | 3/2014 |
| WO | WO 2014043527 | 3/2014 |
| WO | WO 2014047111 | 3/2014 |
| WO | WO 2014047325 | 3/2014 |
| WO | WO 2014055981 | 4/2014 |
| WO | WO 2014059432 | 4/2014 |
| WO | WO 2014064694 | 5/2014 |
| WO | WO 2014066365 | 5/2014 |
| WO | WO 2014089424 | 6/2014 |
| WO | WO 2014093861 | 6/2014 |
| WO | WO 2014110169 | 7/2014 |
| WO | WO 2014111918 | 7/2014 |
| WO | WO 2014114794 | 7/2014 |
| WO | WO 2014114795 | 7/2014 |
| WO | WO 2014114796 | 7/2014 |
| WO | WO 2014114798 | 7/2014 |
| WO | WO 2014116502 | 7/2014 |
| WO | WO 2014121280 | 8/2014 |
| WO | WO 2014128705 | 8/2014 |
| WO | WO 2014134277 | 9/2014 |
| WO | WO 2014138194 | 9/2014 |
| WO | WO 2014138284 | 9/2014 |
| WO | WO 2014138482 | 9/2014 |
| WO | WO 2014138868 | 9/2014 |
| WO | WO 2014144100 | 9/2014 |
| WO | WO 2014144937 | 9/2014 |
| WO | WO 2014145338 | 9/2014 |
| WO | WO 2014147336 | 9/2014 |
| WO | WO 2014152306 | 9/2014 |
| WO | WO 2014152375 | 9/2014 |
| WO | WO 2014152503 | 9/2014 |
| WO | WO 2014153544 | 9/2014 |
| WO | WO 2014158617 | 10/2014 |
| WO | WO 2014162181 | 10/2014 |
| WO | WO 2014162306 | 10/2014 |
| WO | WO 2014163705 | 10/2014 |
| WO | WO 2014168655 | 10/2014 |
| WO | WO 2014179391 | 11/2014 |
| WO | WO 2014181336 | 11/2014 |
| WO | WO 2014189974 | 11/2014 |
| WO | WO 2014190329 | 11/2014 |
| WO | WO 2014191994 | 12/2014 |
| WO | WO 2014193951 | 12/2014 |
| WO | WO 2014194178 | 12/2014 |
| WO | WO 2014197924 | 12/2014 |
| WO | WO 2014200764 | 12/2014 |
| WO | WO 2014201384 | 12/2014 |
| WO | WO 2014201452 | 12/2014 |
| WO | WO 2014205064 | 12/2014 |
| WO | WO 2014205223 | 12/2014 |
| WO | WO 2014205234 | 12/2014 |
| WO | WO 2014207699 | 12/2014 |
| WO | WO 2014210124 | 12/2014 |
| WO | WO 2014210299 | 12/2014 |
| WO | WO 2015003183 | 1/2015 |
| WO | WO 2015006575 | 1/2015 |
| WO | WO 2015009503 | 1/2015 |
| WO | WO 2015013238 | 1/2015 |
| WO | WO 2015020971 | 2/2015 |
| WO | WO 2015028986 | 3/2015 |
| WO | WO 2015031898 | 3/2015 |
| WO | WO 2015051430 | 4/2015 |
| WO | WO 2015052663 | 4/2015 |
| WO | WO 2015057407 | 4/2015 |
| WO | WO 2015057735 | 4/2015 |
| WO | WO 2015057995 | 4/2015 |
| WO | WO 2015061378 | 4/2015 |
| WO | WO 2015061431 | 4/2015 |
| WO | WO 2015061463 | 4/2015 |
| WO | WO 2015061533 | 4/2015 |
| WO | WO 2015061558 | 4/2015 |
| WO | WO 2015075128 | 5/2015 |
| WO | WO 2015081775 | 6/2015 |
| WO | WO 2015089334 | 6/2015 |
| WO | WO 2015092554 | 6/2015 |
| WO | WO 2015120122 | 8/2015 |
| WO | WO 2015125024 | 8/2015 |
| WO | WO 2015127264 | 8/2015 |
| WO | WO 2015127283 | 8/2015 |
| WO | WO 2015128739 | 9/2015 |
| WO | WO 2015128741 | 9/2015 |
| WO | WO 2015128747 | 9/2015 |
| WO | WO 2015132667 | 9/2015 |
| WO | WO 2015132668 | 9/2015 |
| WO | WO 2015135050 | 9/2015 |
| WO | WO 2015142648 | 9/2015 |
| WO | WO 2015142834 | 9/2015 |
| WO | WO 2015148241 | 10/2015 |
| WO | WO 2015171190 | 11/2015 |
| WO | WO 2015171743 | 11/2015 |
| WO | WO 2015179181 | 11/2015 |
| WO | WO 2015191604 | 12/2015 |
| WO | WO 2015191839 | 12/2015 |
| WO | WO 2015195823 | 12/2015 |
| WO | WO 2016005803 | 1/2016 |
| WO | WO 2016011185 | 1/2016 |
| WO | WO 2016020918 | 2/2016 |
| WO | WO 2016027272 | 2/2016 |
| WO | WO 2016059533 | 4/2016 |
| WO | WO 2016065158 | 4/2016 |
| WO | WO 2016073741 | 5/2016 |
| WO | WO 2016077783 | 5/2016 |
| WO | WO 2016083551 | 6/2016 |
| WO | WO 2016093877 | 6/2016 |
| WO | WO 2016097337 | 6/2016 |
| WO | WO 2016108181 | 7/2016 |
| WO | WO 2016133950 | 8/2016 |
| WO | WO 2017062640 | 4/2017 |
| WO | WO 2017087701 | 5/2017 |
| WO | WO 2017096157 | 6/2017 |
| WO | WO 2017100927 | 6/2017 |
| WO | WO 2017101232 | 6/2017 |
| WO | WO 2017117388 | 7/2017 |
| WO | WO 2017127939 | 8/2017 |
| WO | WO 2017136287 | 8/2017 |
| WO | WO 2017136596 | 8/2017 |
| WO | WO 2017165810 | 9/2017 |
| WO | WO 2017189040 | 11/2017 |
| WO | WO 2017192960 | 11/2017 |
| WO | WO 2017196511 | 11/2017 |
| WO | WO 2017196909 | 11/2017 |
| WO | WO 2017196977 | 11/2017 |
| WO | WO 2017197064 | 11/2017 |
| WO | WO 2017197065 | 11/2017 |
| WO | WO 2017218671 | 12/2017 |
| WO | WO 2018017886 | 1/2018 |

OTHER PUBLICATIONS

Bernard et al., "Aortic Valve Area Evolution After Percutaneous Aortic Valvuloplasty," European Heart Journal vol. 11, No. 2, Jul. 1990, pp. 98-107.

BlueCross BlueShield of Northern Carolina Corporate Medical Policy "Balloon valvuloplasty, Percutaneous", (Jun. 1994).

Cimino et al., "Physics of Ultrasonic Surgery using Tissue Fragmentation: Part I and Part II", Ultrasound in Medicine and Biology, vol. 22, No. 1, Jun. 1996, pp. 89-100, and pp. 101-117.

Cimino, "Ultrasonic surgery: power quantification and efficiency optimization", Aesthetic surgery journal, May 2001, 233-241.

Office Action dated Feb. 23, 2011 from Japanese Patent Application No. 2007545650 together with an English language translation, 10 pages.

Cowell et al., "A randomized Trial of Intensive Lipid-Lowering Therapy in Calcific Aortic Stenosis," NEJM vol. 352 No. 23, Jun. 9, 2005, pp. 2389-2397.

De Korte et al., "Characterization of plaque components and vulnerability with intravascular ultrasound elastography" Phys. Med. Biol. vol. 45, Jun. 2000, pp. 1465-1475.

(56) References Cited

OTHER PUBLICATIONS

European Search Report for European App. No. 05853460.3, completed Mar. 13, 2015, 3 pages.
Feldman, "Restenosis Following Successful Balloon Valvuloplasty: Bone Formation in Aortic Valve Leaflets," Cathet Cardiovasc Diagn, vol. 29 No. 1, May 1993, pp. 1-7.
Final Office Action for U.S. Appl. No. 12/870,270, Mailed Jul. 3, 2012, 7 pages.
Final Office Action for U.S. Appl. No. 11/299,246, Mailed Feb. 17, 2010, 6 pages.
Final Office Action for U.S. Appl. No. 11/299,246, Mailed Jun. 6, 2008, 5 pages.
Final Office Action for U.S. Appl. No. 13/329,083, Mailed Jan. 6, 2014, 9 pages.
Final Office Action for U.S. Appl. No. 13/842,785, Mailed Aug. 29, 2014, 5 pages.
Final Office Action for U.S. Appl. No. 13/946,552, Mailed Aug. 29, 2014, 5 pages.
Final Office Action for U.S. Appl. No. 13/946,628, Mailed Sep. 2, 2014, 6 pages.
Fitzgerald et al., "Intravascular Sonotherapy Decreased Neointimal Hyperplasia After Stent Implantation in Swine," Circulation, vol. 103, Apr. 10, 2001, pp. 1828-1831.
Freeman et al., "Ultrasonic Aortic Valve Decalcification: Serial Doppler Echocardiographic Follow up," J Am Coll Cardiol., vol. 16, No. 3, Sep. 1990, pp. 623-630.
Greenleaf et al., "Selected Methods for Imaging Elastic Properties of Biological Tissues" Annu. Rev. Biomed. Eng., vol. 5, 2pp. 57-78, (2003).
Gunn et al., "New Developments in Therapeutic Ultrasound-Assisted Coronary Angioplasty," Curr Interv Cardiol Rep., vol. 1 No. 4, Dec. 1990, pp. 281-290.
Guzman et al., "Bioeffects Caused by Changes in Acoustic Cavitation Bubble Density and Cell Concentration: A Unified Explanation Based on Cell-to-Bubble Ratio and Blast Radius," Ultrasound in Med. & Biol., vol. 29, No. 8, Aug. 2003, pp. 1211-1222.
Hallgrimsson et al., "Chronic Non-Rheumatic Aortic Valvular Disease: a Population Study Based on Autopsies," J Chronic Dis., vol. 32 No. 5, 1979, pp. 355-363. (Applicant points out, in accordance with MPEP 609.04(a), that the year of publication, 1979, is sufficiently earlier than the effective U.S. filing date, so that the particular month of publication is not in issue.).
International Search Report and Written Opinion dated May 1, 2012; International Application No. PCT/US2011/065627; Applicant: Foundry Newco XII, Inc.; 10 pages.
International Search Report and Written Opinion dated Dec. 10, 2012; International Application No. PCT/US2012/043636; Applicant: Foundry Newco XII, Inc.; 21 pages.
International Search Report and Written Opinion dated Jan. 30, 2013; International Application No. PCT/US2012/061215; Applicant: Foundry Newco XII, Inc.; 11 pages.
International Search Report and Written Opinion dated Jan. 30, 2013; International Application No. PCT/US2012/061219; Applicant: Foundry Newco XII, Inc.; 9 pages.
International Search Report and Written Opinion dated Aug. 3, 2018 for PCT Application No. PCT/US2018035086, 15 pages.
International Search Report and Written Opinion dated Aug. 9, 2018 for PCT Application No. PCT/US2018/035081, 11 pages.
International Search Report and Written Opinion dated Jul. 11, 2018 for PCT Application No. PCT/US2018/027990, 15 pages.
International Search Report and Written Opinion dated Jun. 28, 2018 for PCT Application No. PCT/US2018/027983, 15 pages.
International Search report and Written Opinion for International App. No PCT/US2005/044543, dated May 22, 2007, 8 pages.
International Search Report and Written Opinion for International App. No. PCT/US2014/014704, mailed Sep. 4, 2014, 18 pages.
International Search Report and Written Opinion for International Application No. PCT/US2014/029549, mailed Mar. 2, 2015, 20 pages.
Isner et al., "Contrasting Histoarchitecture of calcified leaflets from stenotic bicuspid versus stenotic tricuspid aortic valves," J Am Coll Cardiol., vol. 15, No. 5, Apr. 1990, pp. 1104.
Lung et al., "A Prospective Survey of Patients with Valvular Heart Disease in Europe: The Euro Heart Survey on Valvular Heart Disease," Euro Heart Journal, vol. 24, Jul. 2003, pp. 1231-1243.
McBride et al "Aortic Valve Decalcification," J Thorac Cardiovasc-Surg, vol. 100, Jul. 1990, pp. 36-42.
Miller et al., "Lysis and Sonoporation of Epidermoid and Phagocytic Monolayer Cells by Diagnostic Ultrasound Activation of Contrast Agent Gas Bodies," Ultrasound in Med. & Biol., vol. 27, No. 8, Aug. 2001, pp. 1107-1113.
Mohler, "Mechanisms of Aortic Valve Calcification," Am J Cardiol, vol. 94 No. 11, Dec. 1, 2004, pp. 1396-1402, A6.
Non Final Office Action for U.S. Appl. No. 11/299,246, Mailed Apr. 7, 2009, 6 pages.
Non Final Office Action for U.S. Appl. No. 11/299,246, Mailed Oct. 16, 2008, 7 pages.
Non Final Office Action for U.S. Appl. No. 11/299,246, Mailed Aug. 22, 2007, 4 pages.
Non Final Office Action for U.S. Appl. No. 12/870,270, Mailed Nov. 18, 2011, 9 pages.
Non Final Office Action for U.S. Appl. No. 13/329,083, Mailed Jul. 25, 2013, 16 pages.
Non Final Office Action for U.S. Appl. No. 13/842,785, Mailed Feb. 3, 2014, 24 pages.
Non Final Office Action for U.S. Appl. No. 13/946,552, Mailed Feb. 3, 2014, 23 pages.
Non Final Office Action for U.S. Appl. No. 13/946,628, Mailed Feb. 4, 2014, 24 pages.
Non Final Office Action for U.S. Appl. No. 13/949,098, Mailed Feb. 24, 2014, 28 pages.
Notice of Allowance for U.S. Appl. No. 11/299,246, Mailed May 27, 2010, 6 pages.
Notice of Allowance for U.S. Appl. No. 13/842,785, mailed Apr. 7, 2015, 8 pages.
Notice of Allowance for U.S. Appl. No. 13/946,552, mailed Mar. 25, 2015, 8 pages.
Notice of Allowance for U.S. Appl. No. 13/946,628, mailed Mar. 25, 2015, 8 pages.
Otto et al., "Three-Year Outcome After Balloon Aortic Valvuloplasty. Insights into Prognosis of Valvular Aortic Stenosis," Circulation, vol. 89, Feb. 1994, pp. 642-650.
Passik et al., "Temporal Changes in the Causes of Aortic Stenosis: A Surgical Pathologic Study of 646 Cases," Mayo Clin Proc, vol. 62, Feb. 1987, pp. 19-123.
Quaden et al., "Percutaneous Aortic Valve Replacement: Resection Before Implantation," Eur J Cardiothorac Surg, vol. 27, May 2005, pp. 836-840.
Riebman et al., "New Concepts in the Management of Patients With Aortic Valve Disease." Abstract, Valvular Heart Disease, JACC, 2004, p. 34A. (Applicant points out, in accordance with MPEP 609.04(a), that the year of publication, 2004, is sufficiently earlier than the effective U.S. filing date, so that the particular month of publication is not in issue.).
Rosenschein et al., "Percutaneous Transluminal Therapy of Occluded Saphenous Vein Grafts," Circulation, vol. 99, Jan. 1999, pp. 26-29.
Sakata et al., "Percutaneous Balloon Aortic Valvuloplasty: Antegrade Transseptal vs. Conventional Retrograde Transarterial Approach," Catheter Cardiovasc Interv, vol. 64, No. 3, Mar. 2005, pp. 314.
Sasaki et al., "Scanning electron microscopy and Fourier transformed infrared spectroscopy analysis of bone removal using Er:YAG and C02 lasers" J Periodontal.; vol. 73, No. 6, Jun. 2002, pp. 643-652.
Search Report and Written Opinion dated Dec. 6, 2016 for PCT Application No. PCT/US2016/047831.
The CoreValve System Medtronic, 2012, 4 Pages.
Van Den Brand et al., "Histological Changes in the Aortic Valve after Balloon Dilation: Evidence for a Delayed Healing Process," Br Heart J, Jun. 1992; vol. 67, pp. 445-459.
Verdaadadonk et al., "The Mechanism of Action of the Ultrasonic Tissue Resectors Disclosed Using High-Speed and Thermal Imaging Techniques," SPIE, vol. 3594, Jan. 1999, pp. 221-231.

(56) References Cited

OTHER PUBLICATIONS

Voelker et al., "Inoperative Valvuloplasty in Calcific Aortic Stenosis: a Study Comparing the Mechanism of a Novel Expandable Device with conventional Balloon Dilation," Am Heart J. vol. 122 No. 5, Nov. 1991, pp. 1327-1333.
Waller et al., "Catheter Balloon Valvuloplasty of Stenotic Aortic Valves. Part II: Balloon Valvuloplasty During Life Subsequent Tissue Examination," Clin Cardiol., vol. 14 No. 11, Nov. 1991, pp. 924-930.
Wang, "Balloon Aortic Valvuloplasty," Prog Cardiovasc Dis., vol. 40, No. 1, pp. 27-36. (Jul.-Aug. 1997).
Wilson et al., "Elastography—The movement Begins" Phys. Med. Biol., vol. 45, Jun. 2000, pp. 1409-1421.
Yock et al, "Catheter-Based Ultrasound Thrombolysis," Circulation, vol. 95 No. 6, Mar. 18, 1997, pp. 1411-1416.
Prosecution History from U.S. Appl. No. 13/781,504, dated Feb. 20, 2015 through Nov. 16, 2016, 60 pp.
Prosecution History from U.S. Appl. No. 15/286,623, dated Apr. 20, 2018 through Jan. 17, 2019, 35 pp.
U.S. Appl. No. 15/611,823, filed Jun. 2, 2017, by Mauch et al.
U.S. Appl. No. 15/490,008, filed Apr. 18, 2017, by McLean et al.
Office Action from counterpart Canadian Application No. 2,898,991, dated Dec. 16, 2019, 8 pp.
Office Action, and translation thereof, from counterpart Japanese Application No. 2019-087182, dated Mar. 13, 2020, 8 pp.
U.S. Appl. No. 16/870,012, filed May 8, 2020, naming inventor Mauch et al.
Notice of Reasons for Rejection, Japanese Patent Application No. 2021-038323, mailed Jan. 26, 2022 (with translation).
Notice of Reasons for Rejection, JP Patent Application 2023-003903, mailed Sep. 12, 2023.

\* cited by examiner

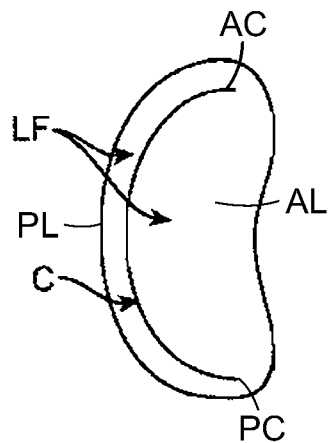
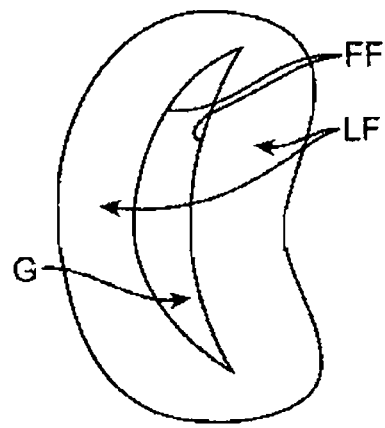
*FIG.1C-1*  *FIG.1C-2*
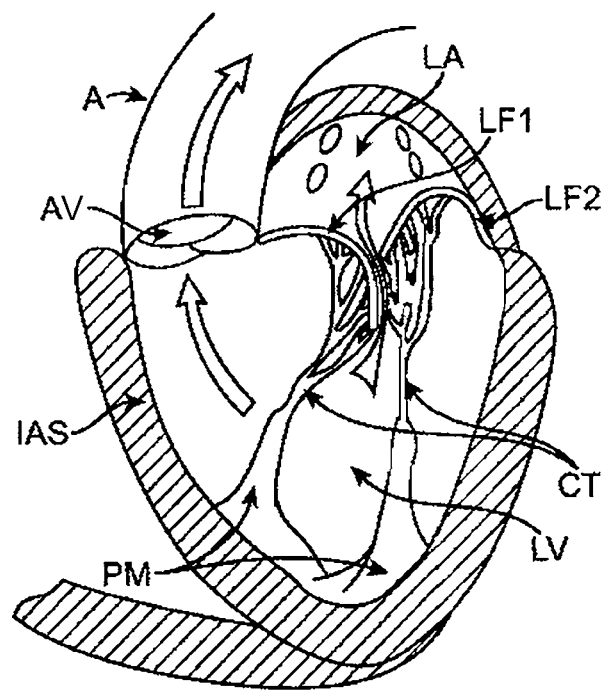
*FIG.1D*

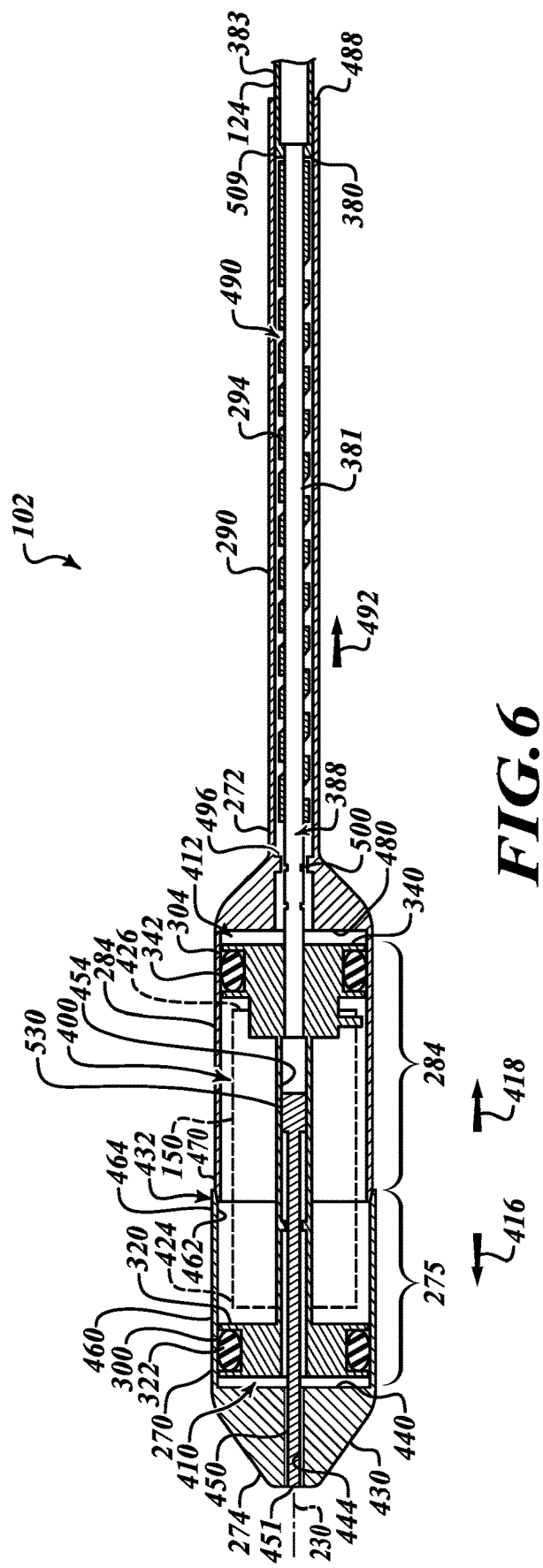

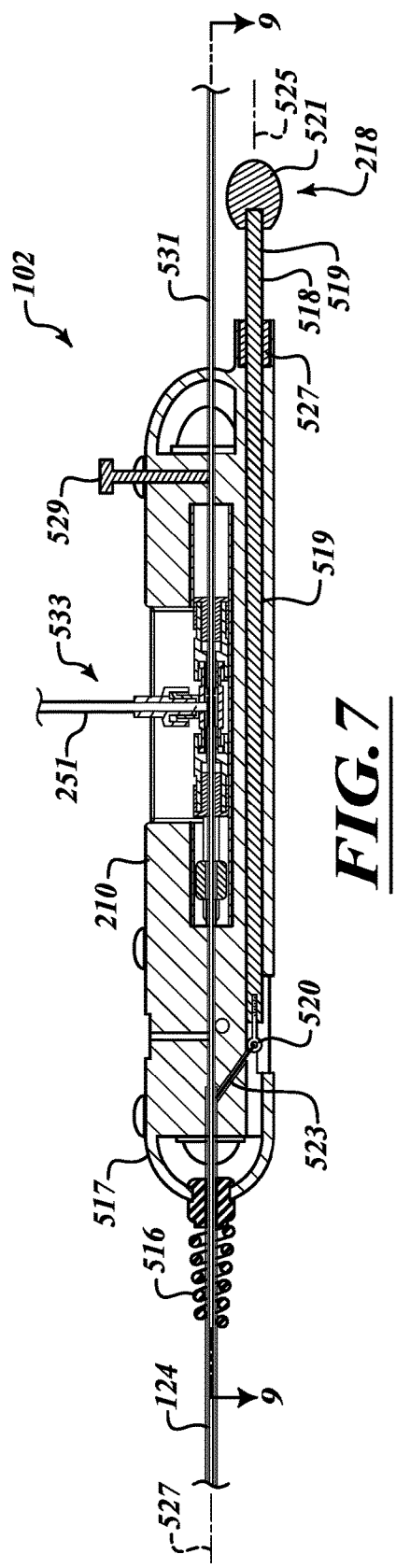
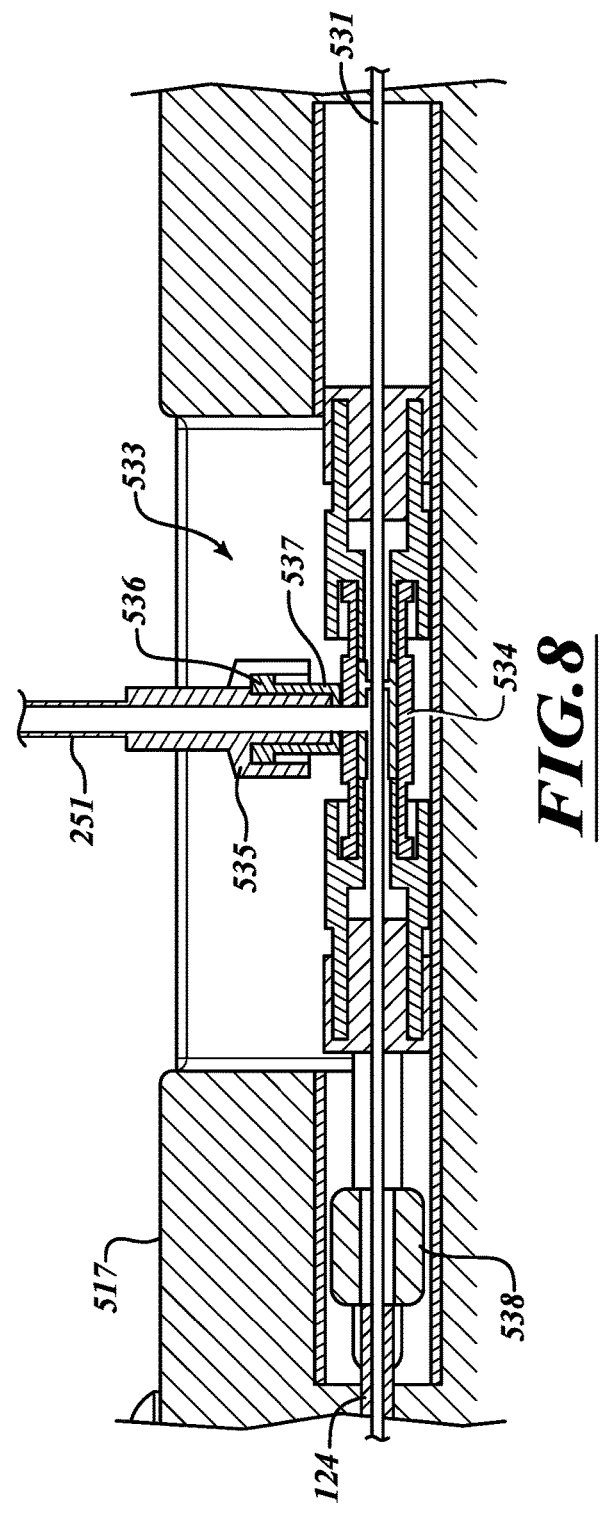

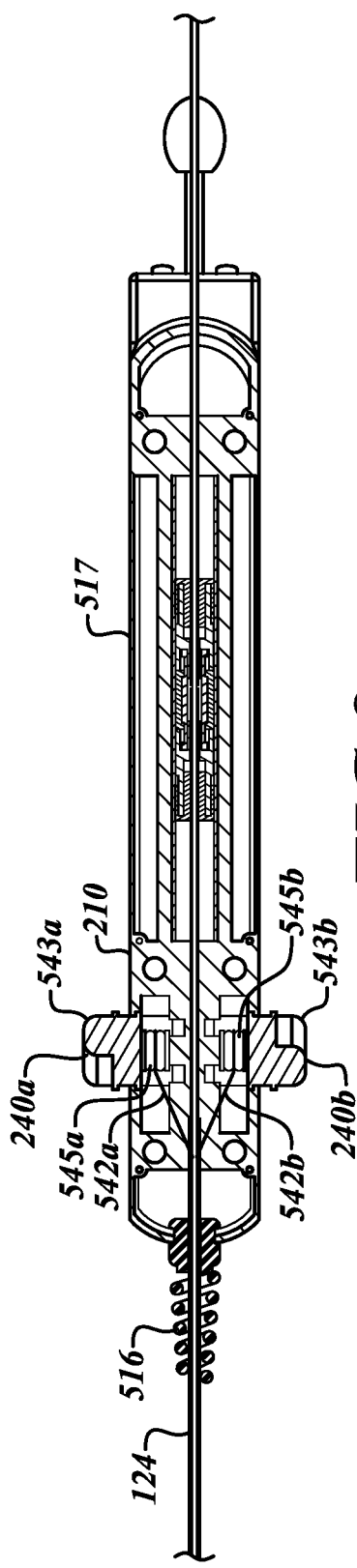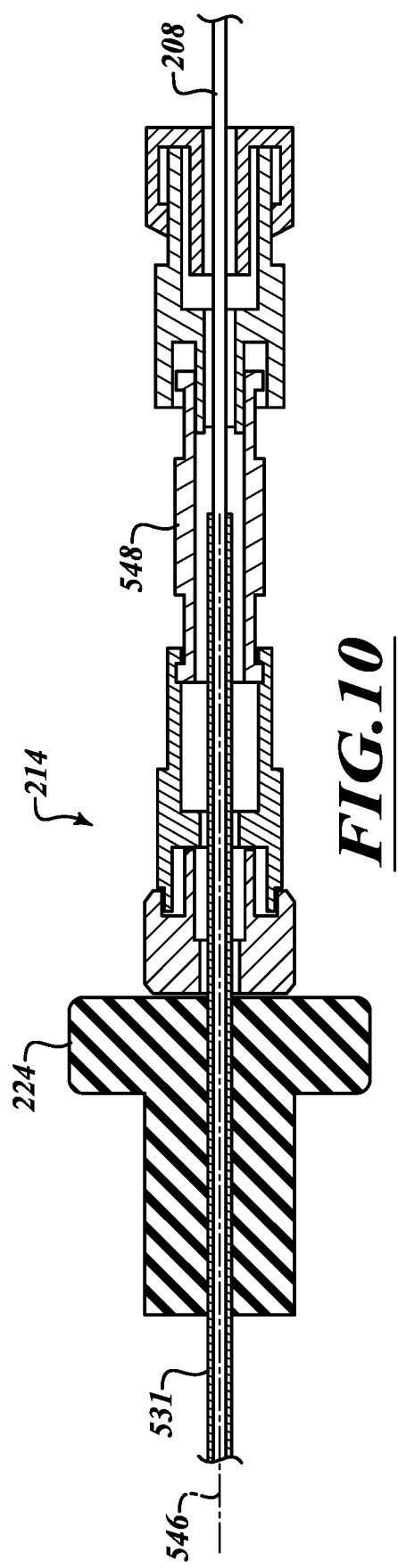

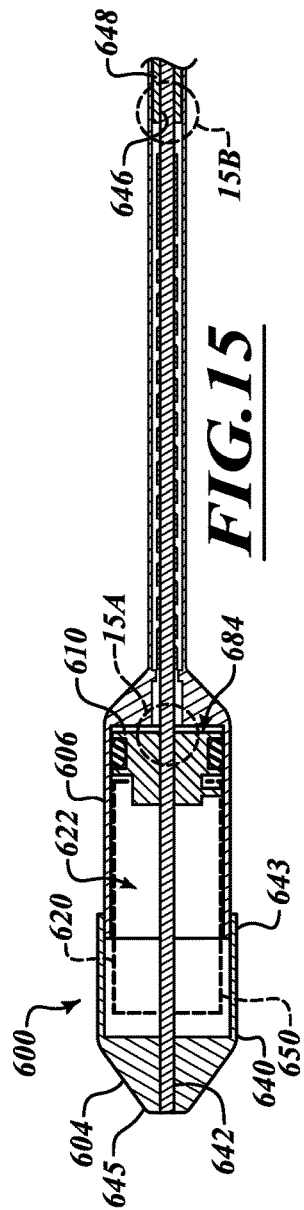
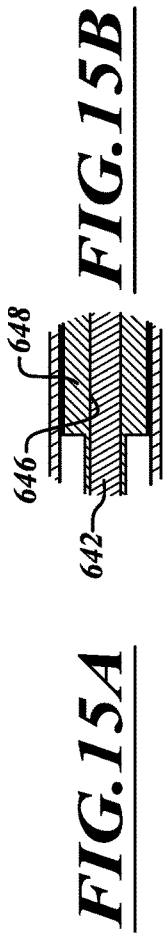
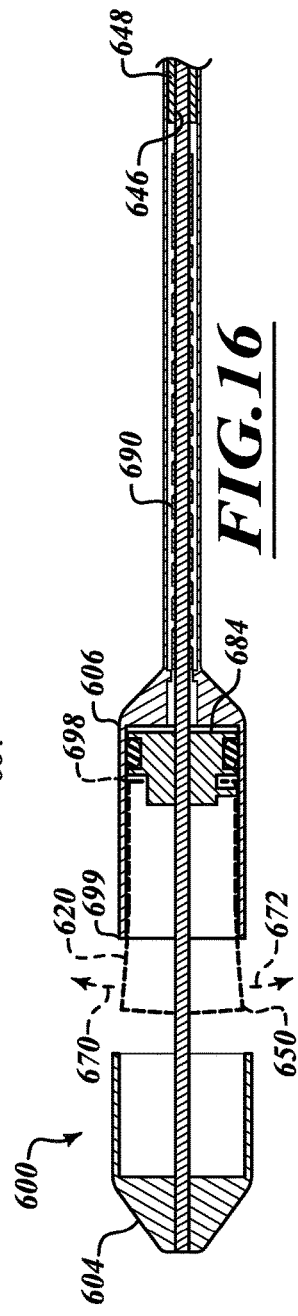
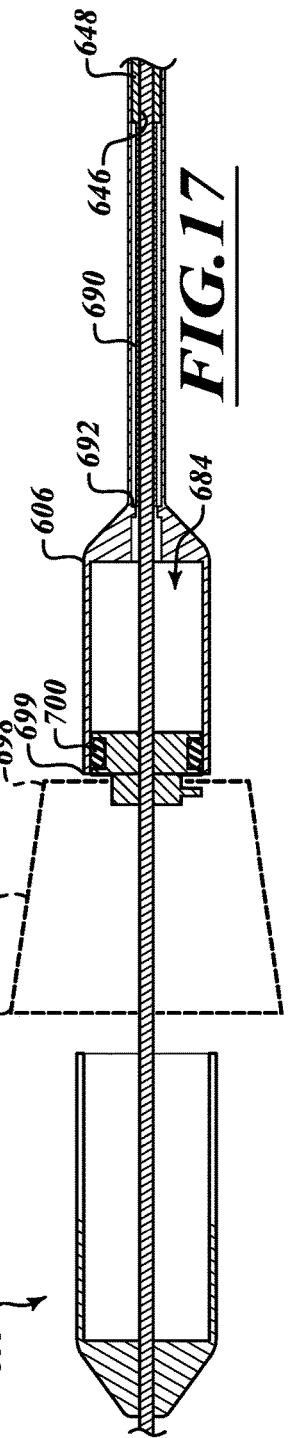

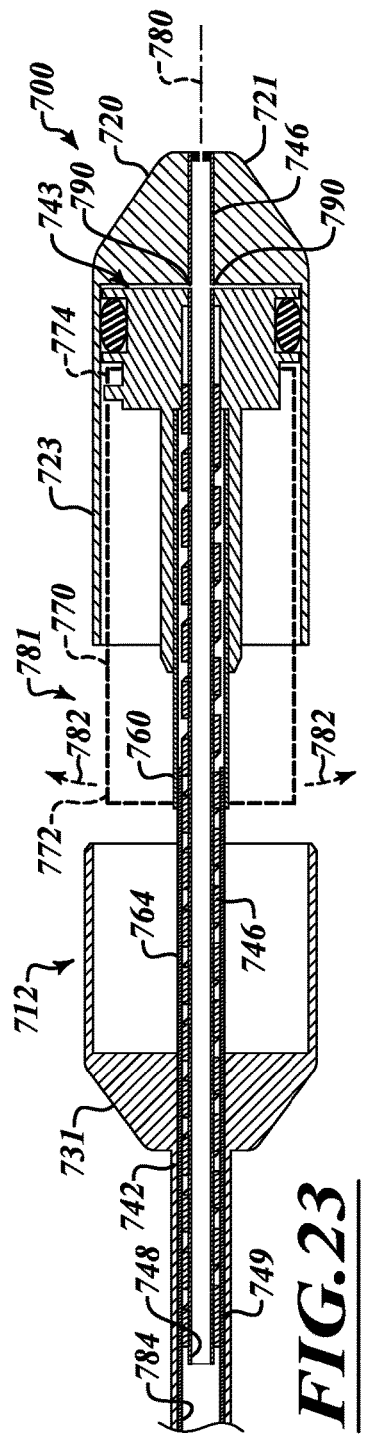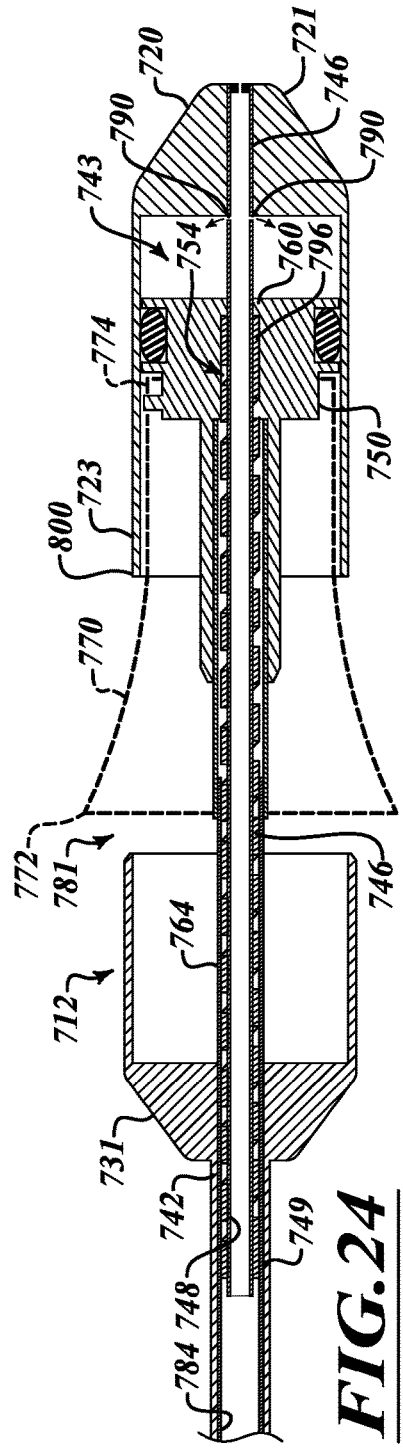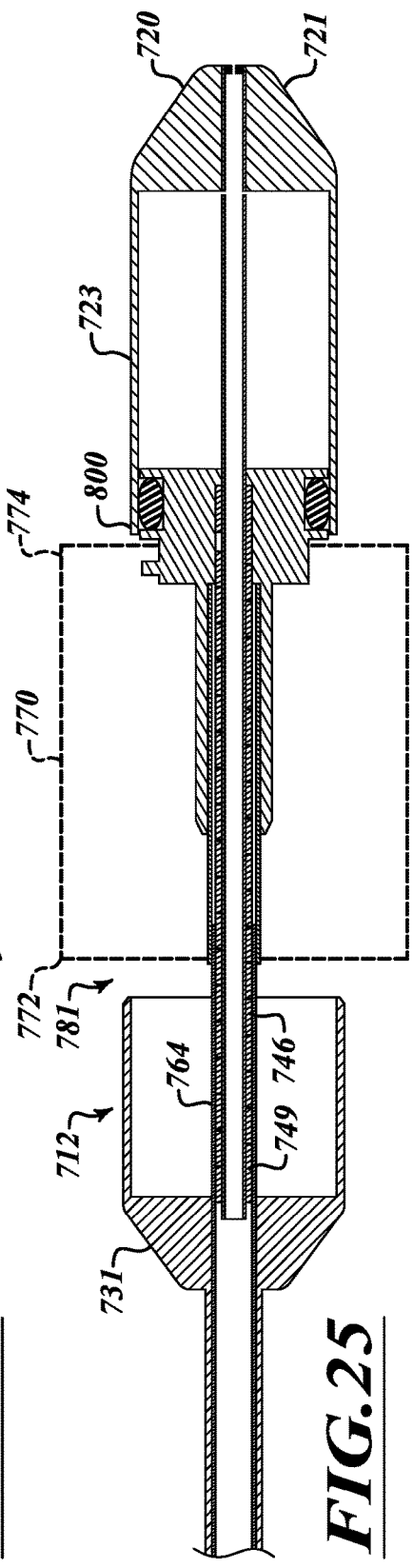

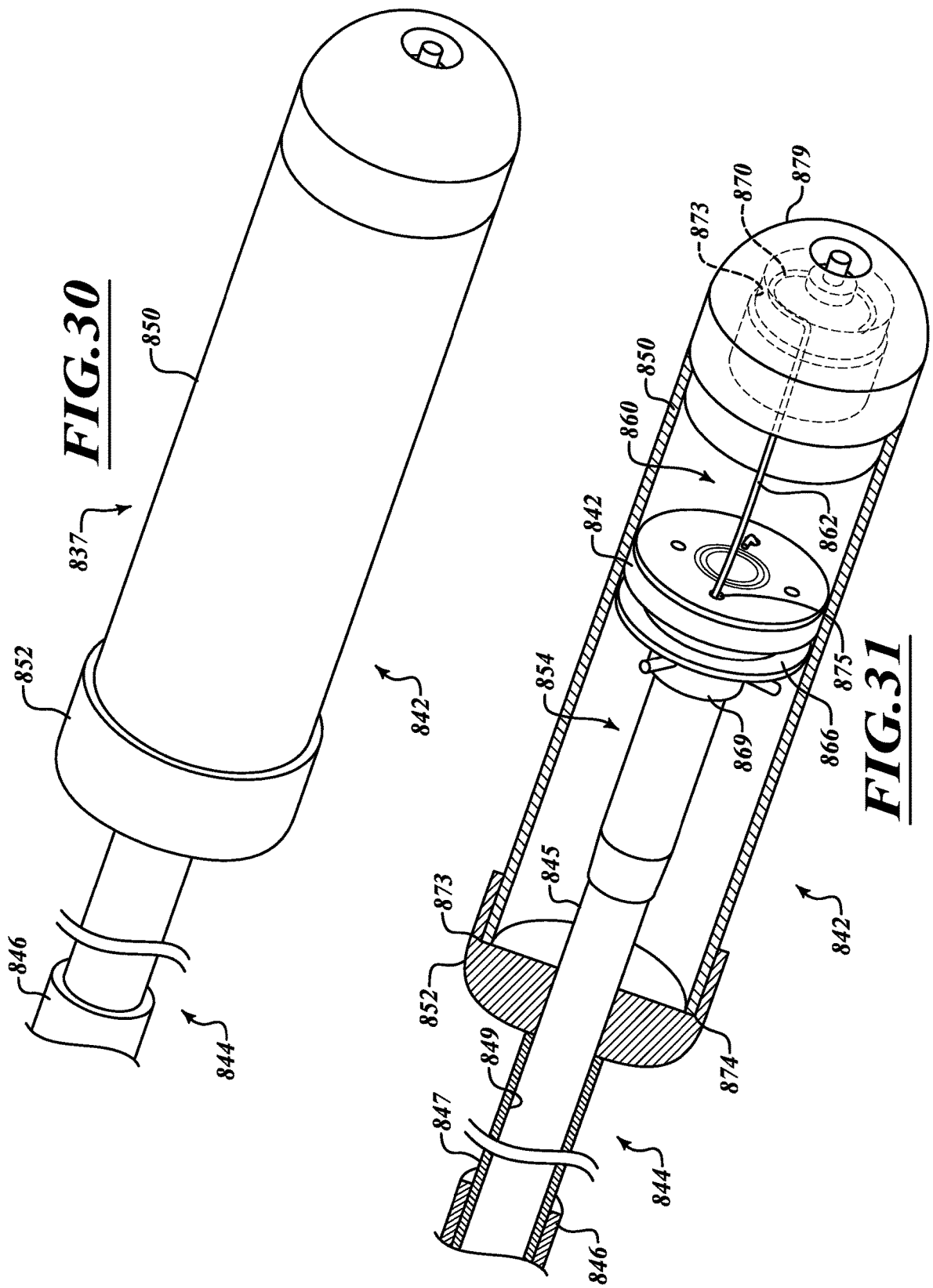

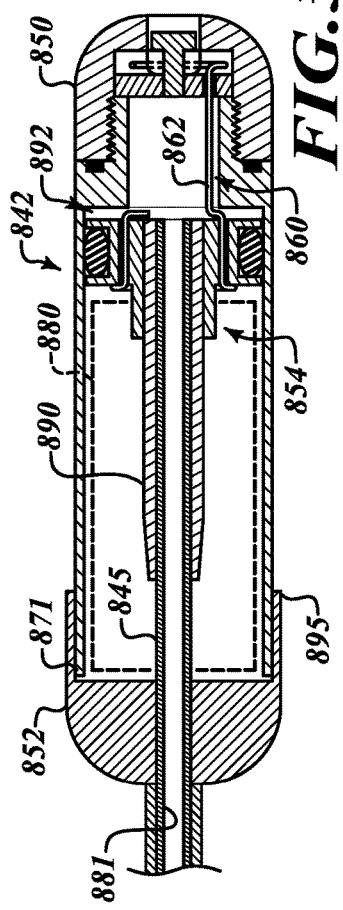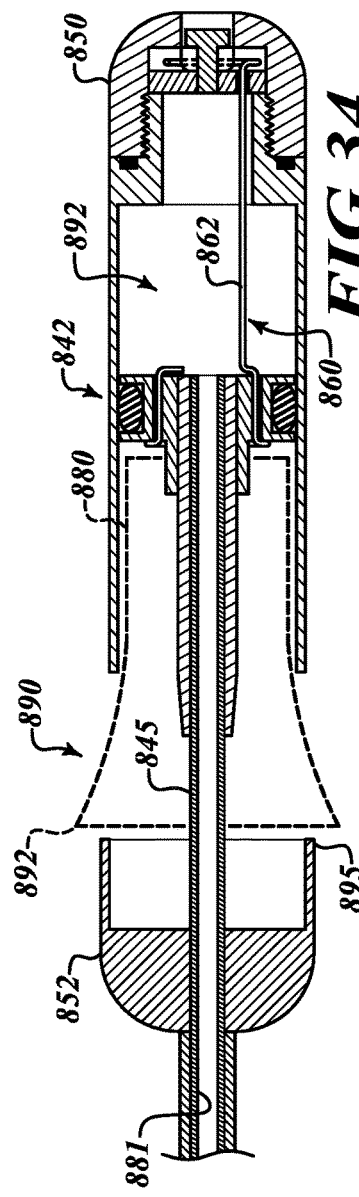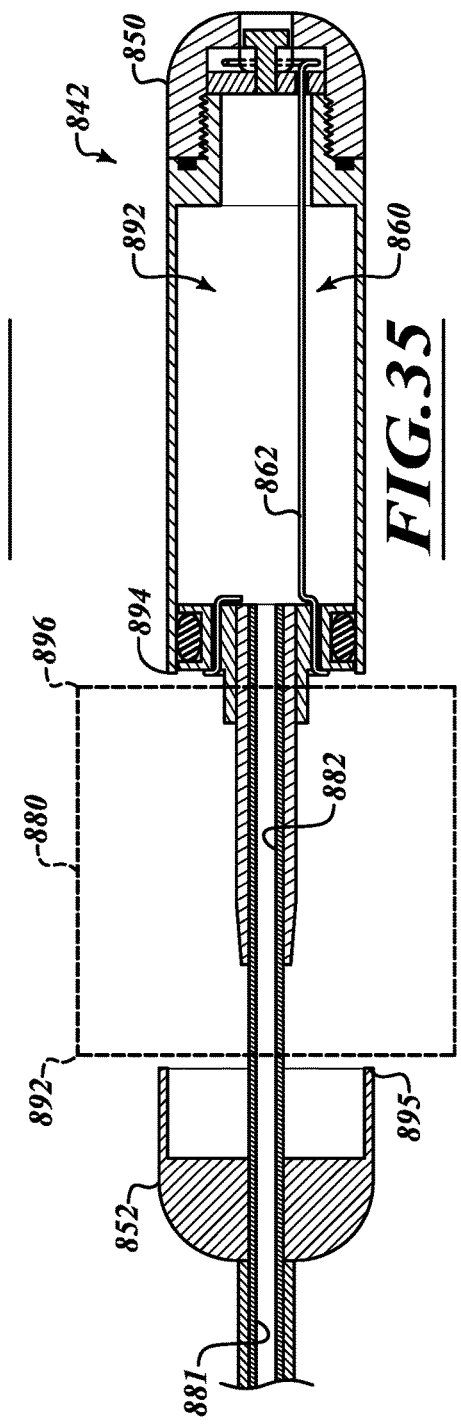

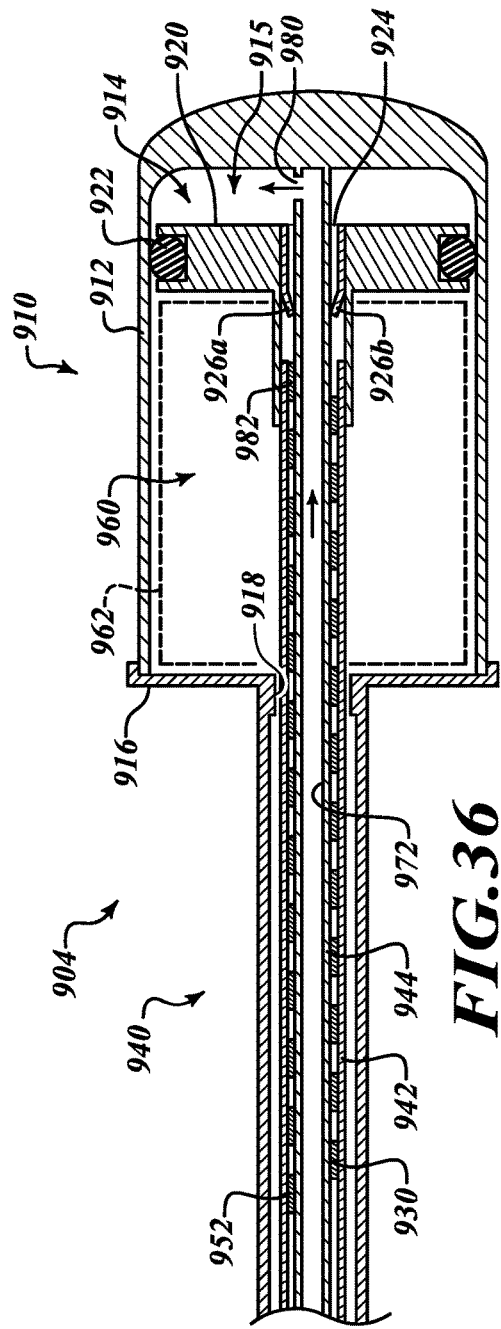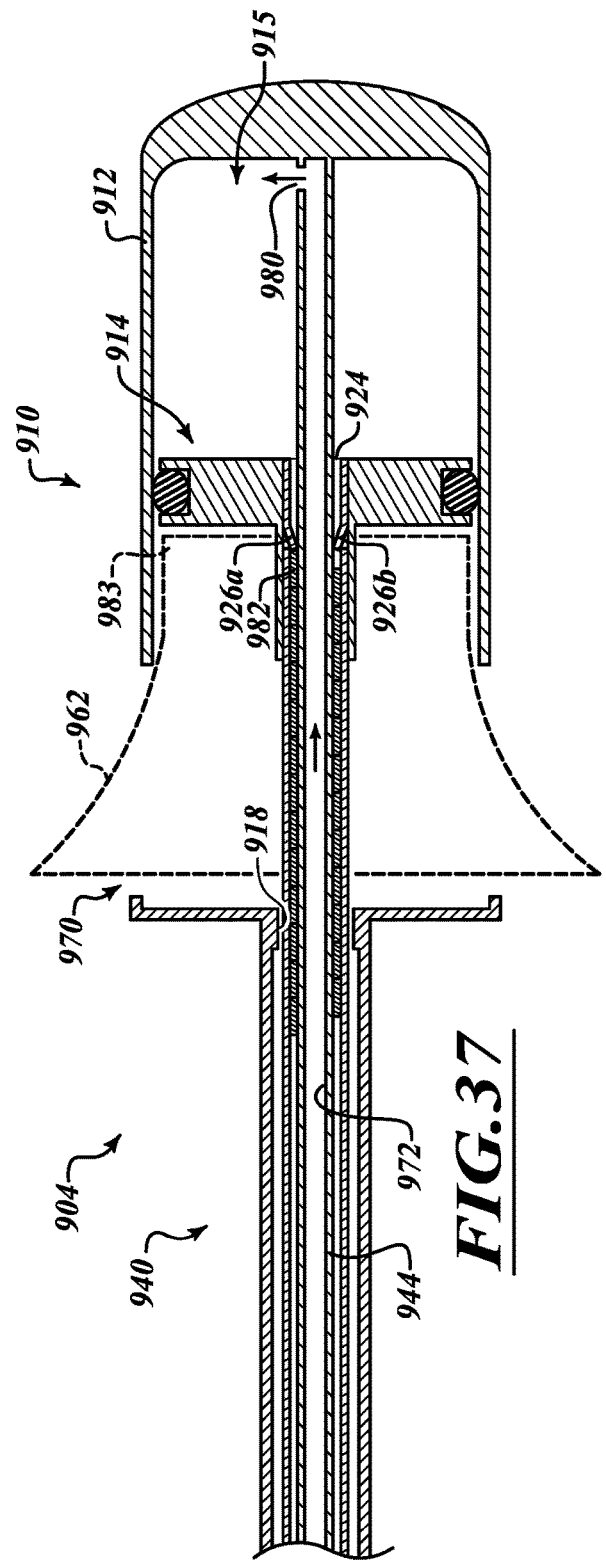

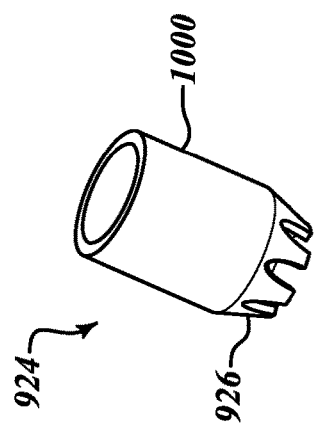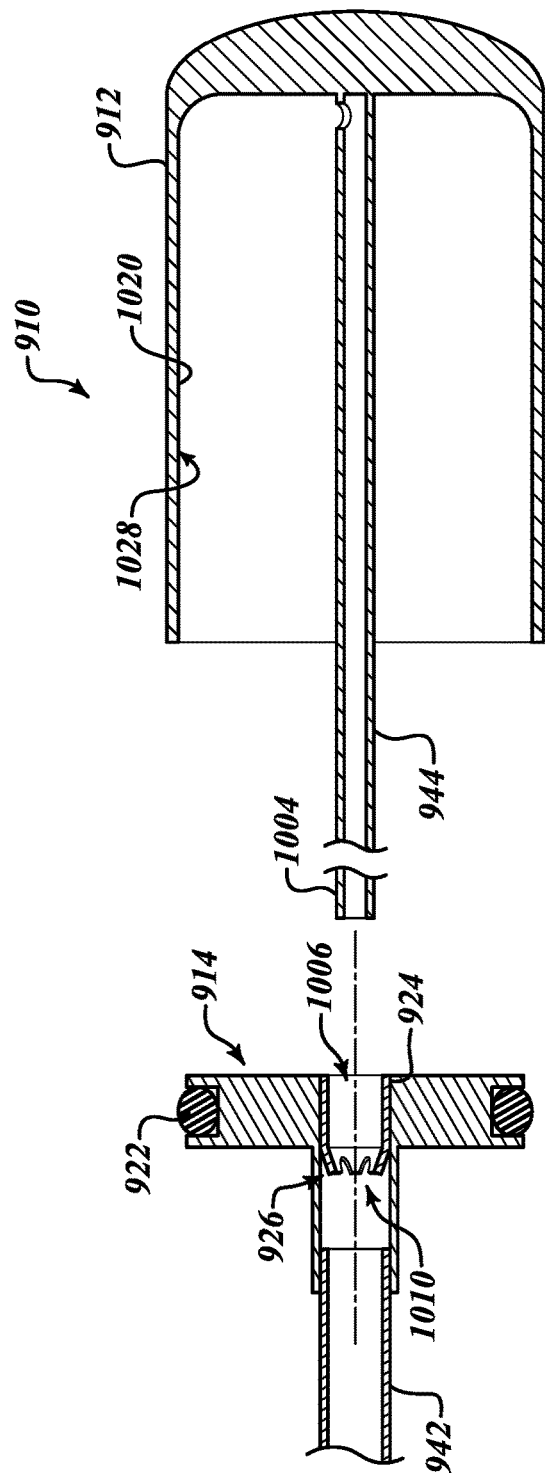
FIG.38
FIG.39

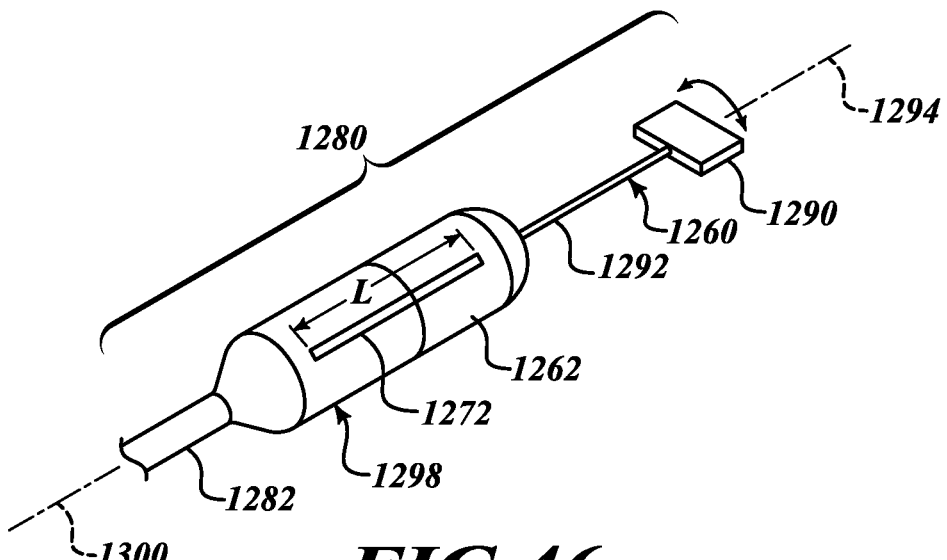
FIG.46
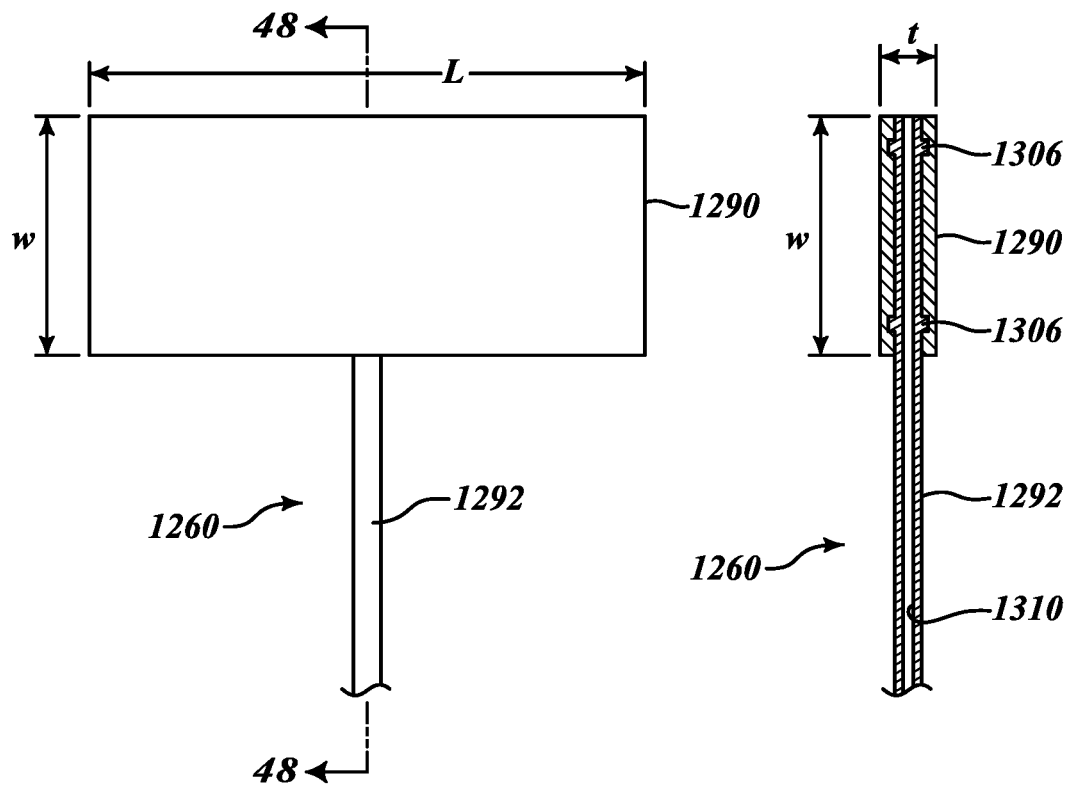 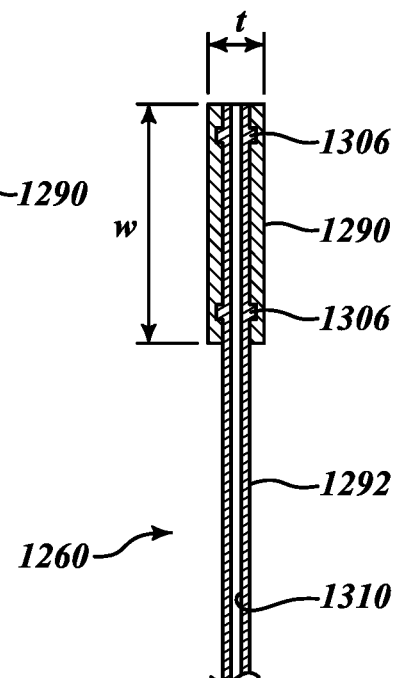
FIG.47  FIG.48

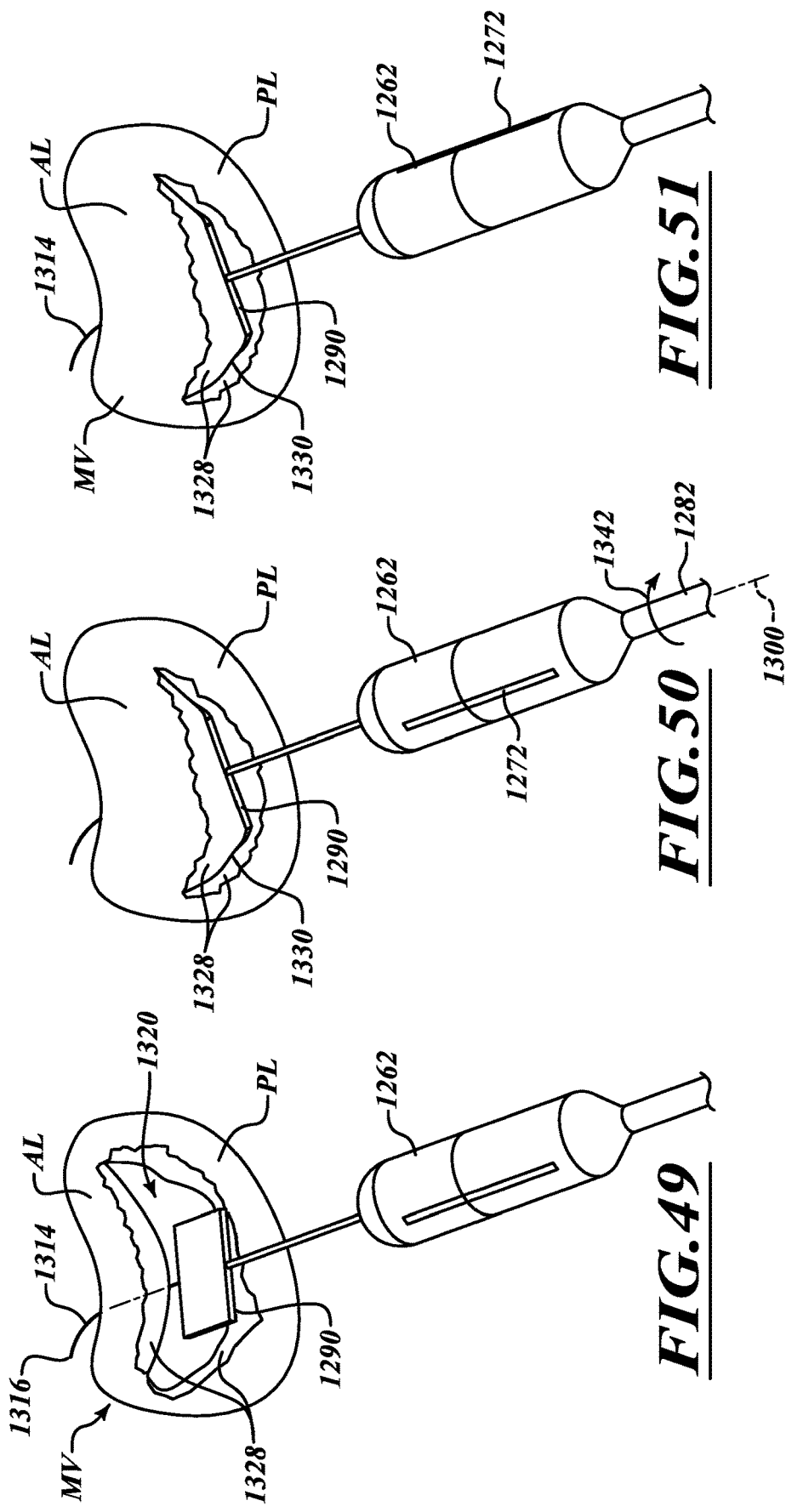

HYDRAULIC DELIVERY SYSTEMS FOR PROSTHETIC HEART VALVE DEVICES AND ASSOCIATED METHODS

CROSS-REFERENCE TO RELATED APPLICATIONS

The present application is a Continuation of and claims priority to U.S. patent application Ser. No. 16/288,679, now allowed, which is a Continuation of and claims priority to U.S. patent application Ser. No. 15/286,623, now U.S. Pat. No. 10,258,468, which is a Division of and claims priority to U.S. patent application Ser. No. 13/781,504, filed Feb. 28, 2013, now U.S. Pat. No. 9,579,198, which claims priority under 35 U.S.C. § 119(e) to U.S. Provisional Patent Application No. 61/605,699, filed Mar. 1, 2012, and entitled "SYSTEM FOR MITRAL VALVE REPLACEMENT," and U.S. Provisional Patent Application No. 61/760,399, filed Feb. 4, 2013, and entitled "HYDRAULIC DELIVERY SYSTEMS FOR PROSTHETIC HEART VALVE DEVICES AND ASSOCIATED METHODS," the disclosures of which are incorporated herein by reference in their entireties.

TECHNICAL FIELD

The present technology relates generally to hydraulic delivery systems and methods for using the same. In particular, several embodiments are directed to hydraulic delivery systems for delivering prosthetic heart valve devices.

BACKGROUND

During a normal cycle of heart contraction (systole), when the left ventricle contracts, the mitral valve acts as a check valve to prevent flow of oxygenated blood back into the left atrium. Oxygenated blood can be pumped into the aorta through the aortic valve. Regurgitation of the mitral valve can significantly decrease the pumping efficiency of the heart, placing the patient at risk of severe, progressive heart failure. Mitral valve regurgitation can be characterized by retrograde flow from the left ventricle of a heart through an incompetent mitral valve into the left atrium. Mitral valve regurgitation can result from a number of mechanical defects. For example, leaflets, chordae tendineae coupled to the leaflets, or the papillary muscles of the mitral valve may be damaged or otherwise dysfunctional. In at least some instances, the mitral valve's annulus supporting the leaflets may be damaged, dilated, or weakened, thereby limiting the ability of the mitral valve to close adequately against the high pressures of the left ventricle.

Mitral valve replacement is often performed to treat mitral valves. Unfortunately, mitral valve replacement poses unique anatomical obstacles, rendering mitral valve replacement procedures risky and more challenging than other types of valve replacements, such as aortic valve replacement. This is because the mitral valve annulus often has a non-circular D shape or kidney like shape, with a non-planar geometry. It may be difficult to properly position a prosthetic mitral valve within the native mitral valve. If the prosthetic mitral valve is at an improper orientation, blood may flow through gaps between the prosthetic mitral valve and the leaflets and/or annulus of the native mitral valve. Percutaneous catheters can be used to deliver prosthetic valves. Unfortunately, self-expanding prosthetic mitral valves can deploy in an uncontrolled manner due to axial jumping or self-ejection. The uncontrolled deployment of prosthetic mitral valves can result in improper positioning of the prosthetic mitral valve resulting in leakage, migration of the prosthetic mitral valve, and other unwanted problems.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components may be shown as transparent in certain views for clarity of illustration only and not to indicate that the illustrated component is necessarily transparent.

FIG. 1A-1 is a schematic cross-sectional side view of a native mitral valve of a mammalian heart.

FIG. 1C-1 is a schematic illustration of a native mitral valve of a heart showing normal closure of native mitral valve leaflets.

FIG. 1C-2 is a schematic illustration of a native mitral valve of a heart showing abnormal closure of native mitral valve leaflets in a dilated heart, and which is suitable for treatment with systems in accordance with embodiments of the present technology.

FIG. 1D illustrates mitral valve regurgitation in the left ventricle of a heart having impaired papillary muscles, and which is suitable for treatment with systems in accordance with embodiments of the present technology.

FIG. 6 is a cross-sectional view of the distal portion taken along line 6-6 of FIG. 4.

FIG. 7 is a cross-sectional view of a control unit of the system of FIG. 3.

FIG. 8 is a detailed cross-sectional view of internal components of the control unit of FIG. 7.

FIG. 9 is a cross-sectional view of the control unit taken along line 9-9 of FIG. 7.

FIG. 10 is a cross-sectional view of a rotational control assembly in accordance with various embodiments of the present technology.

FIGS. 15-17 are a series of views of a method of deploying a prosthetic device from a delivery capsule in accordance with various embodiments of the present technology.

FIGS. 23-25 are a series of views of a method of deploying a prosthetic device from a delivery capsule of FIG. 22 in accordance with various embodiments of the present technology.

FIG. 30 is an isometric view of a distal portion of a catheter in accordance with various embodiments of the present technology.

FIGS. 31 and 32 are isometric cutaway views of the distal portion of FIG. 30.

FIGS. 33-35 are a series of views of a method of deploying a prosthetic device from the catheter of FIG. 30.

FIG. 36 is a cross-sectional view of a distal portion of a catheter in accordance with various embodiments of the present technology.

FIG. 37 is a cross-sectional view of the distal portion of FIG. 36 holding a prosthetic device in a partially expanded configuration.

FIG. 38 is an isometric view of a positioner in accordance with various embodiments of the present technology.

FIG. 39 is an exploded cross-sectional view of the distal portion of FIG. 36 in accordance with various embodiments of the present technology.

FIG. 46 is an isometric view of a distal portion of a catheter in accordance with various embodiments of the present technology.

FIG. 47 is a top view of a positioning assembly in accordance with various embodiments of the present technology.

FIG. 48 is a cross-sectional view of the positioning assembly taken along line 48-48 of FIG. 47.

FIGS. 49-53 are a series of views of a method of aligning a delivery capsule with a native mitral valve in accordance with various embodiments of the present technology.

DETAILED DESCRIPTION

Figure 1:
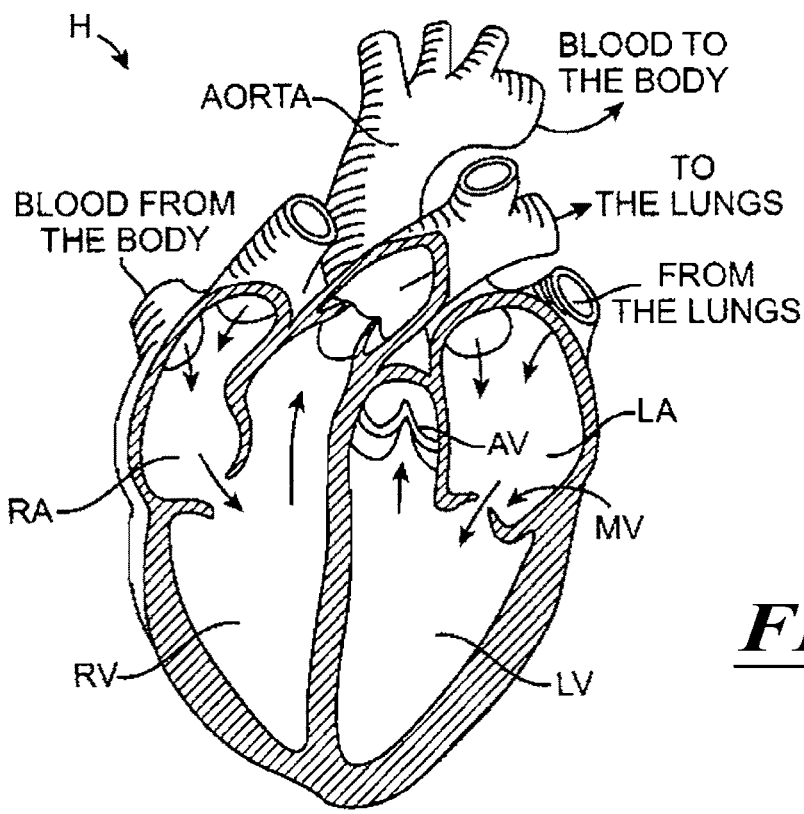
FIGS. 1 and 1A are schematic illustrations of a mammalian heart having native valve structures suitable for replacement with prosthetic devices in accordance with embodiments of the present technology.

The present technology is generally directed to treatment of heart valves and other anatomical structures. Specific details of numerous embodiments of the technology are described below with reference to FIGS. 1-77. Although many of the embodiments are described below with respect to catheter systems, prosthetic devices, and methods for treating a native heart valve using prosthetic devices, other applications and other embodiments in addition to those described herein are within the scope of the technology. A person of ordinary skill in the art will understand that the technology can have other embodiments with additional elements, or the technology can have other embodiments without several of the features shown and described below with reference to FIGS. 1-77.

With regard to the terms "distal" and "proximal" within this description, unless otherwise specified, the terms can reference a relative position of the portions of a system, catheter, and/or associated delivery equipment with reference to an operator and/or a location in the patient. For example, in referring to a catheter suitable to deliver and position various prosthetic devices described herein, "proximal" can refer to a position closer to the operator of the catheter or an incision into vasculature, and "distal" can refer to a position that is more distant from the operator of the catheter or further from the incision along the vasculature (e.g., a position at an end of the catheter). For ease of reference, throughout this disclosure identical reference numbers and/or letters are used to identify similar or analogous components or features, but the use of the same reference number does not imply that the parts should be construed to be identical. Indeed, in many examples described herein, the identically numbered parts are distinct in structure and/or function. The headings provided herein are for convenience only.

Overview

The present technology is directed generally to systems, apparatuses, and methods to treat one or more sites in a subject's body. For example, at least some embodiments of the present technology can be used to treat heart valves (e.g., mitral valves, aortic valves, tricuspid valves, and/or pulmonic valves). The treatment can include, without limitation, valve replacement, valve repair, valve alternation, or other procedures that affect functioning of the valve. The apparatuses and methods can enable a percutaneous approach using a catheter delivered intravascularly through a vein or an artery into the heart. The catheters and methods also enable other less-invasive approaches including, without limitation, trans-apical approaches, trans-atrial approaches, and direct aortic delivery. In more invasive approaches, the catheters and methods enable invasive approaches, including open procedures.

In some embodiments, a catheter includes a delivery device configured to contain a prosthetic device (e.g., a prosthetic heart valve device, a replacement heart valve, etc.). The delivery device can be a capsule reconfigured to deploy the prosthetic device. In some embodiments, the delivery device can be moved from a containment configuration for holding the prosthetic device to a deployment configuration to deploy the prosthetic device. For example, at least a portion of the capsule can be actuated (e.g., hydraulically actuated, mechanically actuated, etc.) to unsheathe or otherwise release at least a portion of the prosthetic device.

The capsule can controllably deploy the prosthetic device to minimize, limit, or substantially eliminate uncontrolled movement of the prosthetic device. In some embodiments, the capsule can limit, minimize, or substantially eliminate axial jumping, self-ejection, and/or movement of the prosthetic device that may cause misalignment with the native valve. In some embodiments, the capsule (e.g., a prosthetic mitral valve) holds the prosthetic device stationary relative to, for example, the native valve, chambers of heart on opposing sides of the native valve, or the like.

The prosthetic device in a delivery configuration can have an outer diameter of about 8 mm to about 12 mm for trans-apical approaches. The prosthetic device can also have a low profile suitable for delivery through small-diameter guide catheters positioned in the heart via the trans-septal, retrograde, or other approaches described herein. For example, the prosthetic device in the delivery configuration can have an outer diameter equal to or less than about 10 mm for trans-septal approaches. In some embodiments, the outer diameter of the trans-septal prosthetic device is about 8 mm to about 10 mm. The prosthetic device in the delivery configuration can have an outer diameter equal to about 8 mm to about 10 mm for retrograde approaches. Other dimensions are also possible.

The prosthetic devices can be configured to expand to a deployed configuration. "Deployed configuration," as used herein with respect to a prosthetic device, generally refers to the prosthetic device once expanded at a delivery site (e.g., a native valve site) and subject to the constraining and distorting forces exerted by the native anatomy. As used herein, "expanded configuration" generally refers to the configuration of a device when allowed to freely expand to an unrestrained size without the presence of constraining or distorting forces.

As used herein, the term "housing" generally refers to a structure capable of covering a prosthetic device. In some embodiments, the housing can include multiple sheaths (e.g., a pair of sheathes). In other embodiments, the housing can include a single sheath and a cover. The cover can be used to close and open an open end of the sheath. In yet further embodiments, the housing can be a clam shell assembly that includes, without limitation, a pair of clam shells that can be moved apart to deploy the prosthetic device. The configuration and components of the housing can be selected based on, for example, the delivery path, treatment site, and/or configuration of the prosthetic device. In still further embodiments, the housing is part of a delivery capsule.

In some embodiments, a catheter for delivering a prosthetic device into a heart of a patient comprises a delivery capsule movable between different configurations (e.g., a containment configuration for holding the prosthetic device, a deployment configuration for deploying the prosthetic device, etc.) and a positioner (e.g., a percutaneous elongate positioner). The positioner is movable from a delivery state to a tissue-contacting state. The positioner in the tissue-contacting state is configured to contact tissue of the heart to position the prosthetic device contained in the delivery capsule relative to a native valve while the delivery capsule is reconfigured to deploy the prosthetic device within the native valve.

In some embodiments, a system may include a catheter with a control device. The control device can be configured to deploy the prosthetic device by hydraulically releasing at least a portion of the prosthetic device. For example, in some embodiments a portion of the prosthetic device can be unsheathed mechanically and another portion of the prosthetic device can be unsheathed hydraulically. In other embodiments, however, the entire prosthetic device may be unsheathed hydraulically. The delivery capsule can be biased to counteract forces produced by the prosthetic device. In some embodiments, for example, a biasing force can counteract the forces produced by a self-expanding prosthetic device.

In some embodiments, for example, the control unit can be used to position the prosthetic device carried by the catheter to the treatment site. The control unit can include, without limitation, a screw-drive mechanism to controllable move at least a portion of housing to unsheathe a first portion of the prosthetic device. Another portion of the prosthetic device can be unsheathed before, during, and/or after unsheathing of the first portion of the prosthetic device. Additionally or alternatively, the control unit can include a slider mechanism used to axially move at least a portion of the housing to unsheathe the prosthetic device. In still further embodiments, the control unit may include other features and/or a different configuration.

In further embodiments, a system for implantation of a prosthetic heart valve device comprises an elongated catheter body and a delivery capsule coupled to the elongated catheter body. The delivery capsule is configured to contain a prosthetic heart valve device. The delivery capsule is configured to be hydraulically driven to deploy the prosthetic device (e.g., a prosthetic heart valve device). In some embodiments, the delivery capsule can include a housing and a hydraulic mechanism (e.g., a piston device) that contacts the housing to inhibit movement of the delivery capsule from a containment configuration to a deployment configuration. The hydraulic mechanism can include one or more piston devices that contact the housing. Additionally or alternatively, the delivery capsule can include a biasing device that urges at least a portion of the delivery capsule towards a containment configuration when the delivery capsule moves from a containment configuration towards a deployment configuration.

In some embodiments, a system for delivering a prosthetic device includes an elongated catheter body, a housing, a plunger or piston, and a prosthetic device. The housing can be coupled to the elongated catheter body and can include a distal nose cone and a proximal capsule. In some embodiments, the housing can include a split sheath. The prosthetic device and the plunger can be positioned in the housing to allow hydraulic actuation of the housing. The prosthetic device can be deployed in a controlled manner to minimize or limit jumping of the prosthetic device.

Cardiac Physiology

Figure 1A:
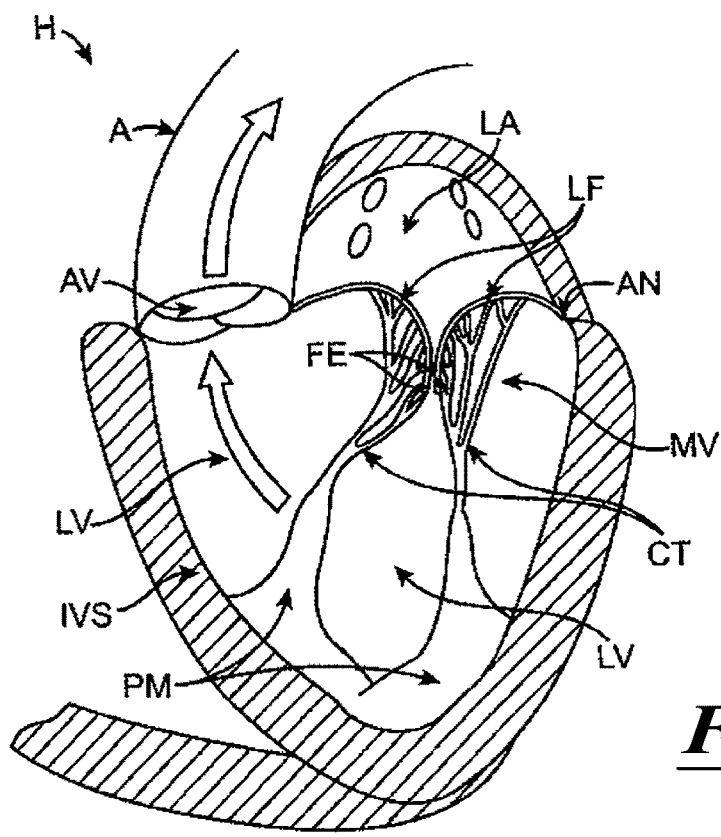
Figures 1, 1A:
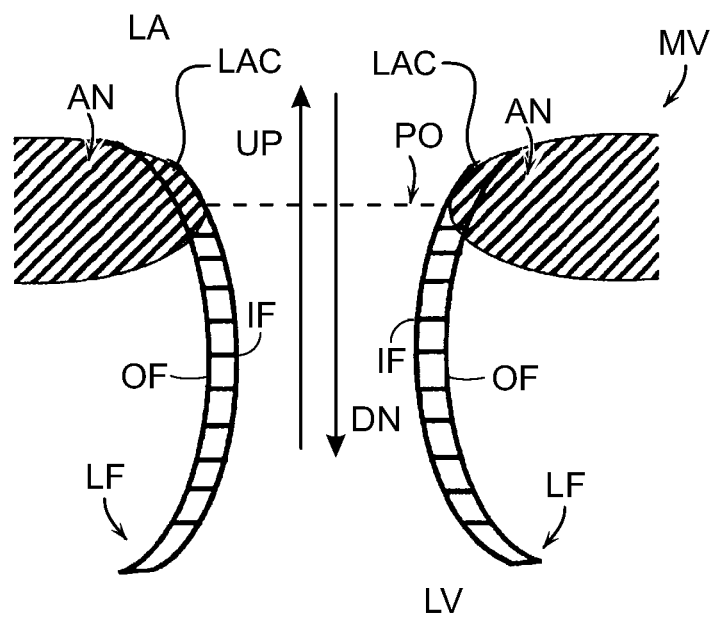

FIGS. 1 and 1A show a heart H that comprises a right atrium RA and a right ventricle RV that receive blood from the body and pump the blood from the body to the lungs. The left atrium receives oxygenated blood from the lungs via the pulmonary veins PV and pumps this oxygenated blood through the mitral MV into the left ventricle LV. The left ventricle LV pumps the blood through the aortic valve AV into the aorta from which it flows throughout the body.

The left ventricle LV of a normal heart H in systole is illustrated in FIG. 1A. In systole, the left ventricle LV contracts and blood flows outwardly through the aortic valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly, or "coapt" to close, as illustrated in FIG. 1A. The opposite ends of the leaflets LF are attached to the surrounding heart structure via an annular region of tissue referred to as the annulus AN. The free edges FE of the leaflets LF are secured to the lower portions of the left ventricle LV through chordae tendineae CT (referred to hereinafter "chordae") which include a plurality of branching tendons secured over the lower surfaces of each of the valve leaflets LF. The chordae CT in turn, are attached to the papillary muscles PM, which extend upwardly from the lower wall of the left ventricle and interventricular septum IVS.

The mitral valve MV comprises a pair of leaflets having free edges FE which meet evenly, or "coapt" to close, as illustrated in FIG. 1A. The opposite ends of the leaflets LF are attached to the surrounding heart structure via an annular region of tissue referred to as an annulus AN.

FIG. 1A-1 is a schematic cross-sectional side view of tissue of the mitral valve MV. The mitral valve MV includes the annulas AN and leaflets LF. Opposite ends of the leaflets LF are attached to the surrounding heart structure via a fibrous ring of dense connective tissue of the annulus AN, which is distinct from both the leaflet tissue LF as well as the adjoining muscular tissue of the heart wall. The leaflets LF and annulus AN are comprised of different types of cardiac tissue having varying strength, toughness, fibrosity, and flexibility. Tissue of the annular annulus AN is typically tougher, more fibrous, and stronger than leaflet tissue LF. Furthermore, the mitral valve MV may also comprise a unique region of tissue interconnecting each leaflet LF to the annulus AN, referred to herein as leaflet/annulus connecting tissue LAC (indicated by overlapping cross-hatching in FIG. 1A-1). A subannular surface of the mitral valve MV is a tissue surface lying on the ventricular side of the plane PO, and preferably one that faces generally downstream, toward the left ventricle LV. The subannular surface may be disposed on the annulus AN itself or the ventricular wall behind the native leaflets LF, or it may comprise a surface of the native leaflets LF, either inward-facing IF or outward-facing OF, which lies below the plane PO. The subannular surface or subannular tissue may thus comprise the annulus AN itself, the native leaflets LF, leaflet/annulus connective tissue, the ventricular wall or combinations thereof.

Figure 1B:
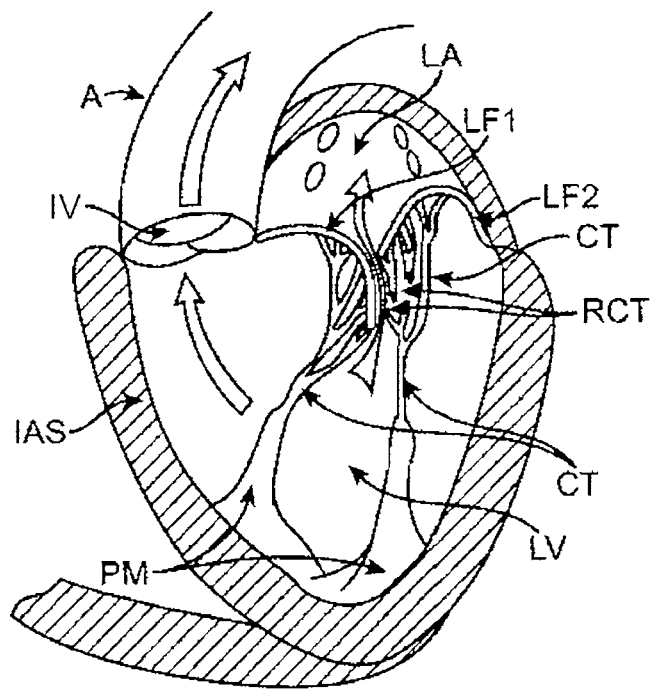
FIG. 1B is a schematic illustration of the left ventricle of a heart having prolapsed leaflets in the native mitral valve, and which is suitable for treatment with systems in accordance with embodiments of the present technology.
Figure 1C:
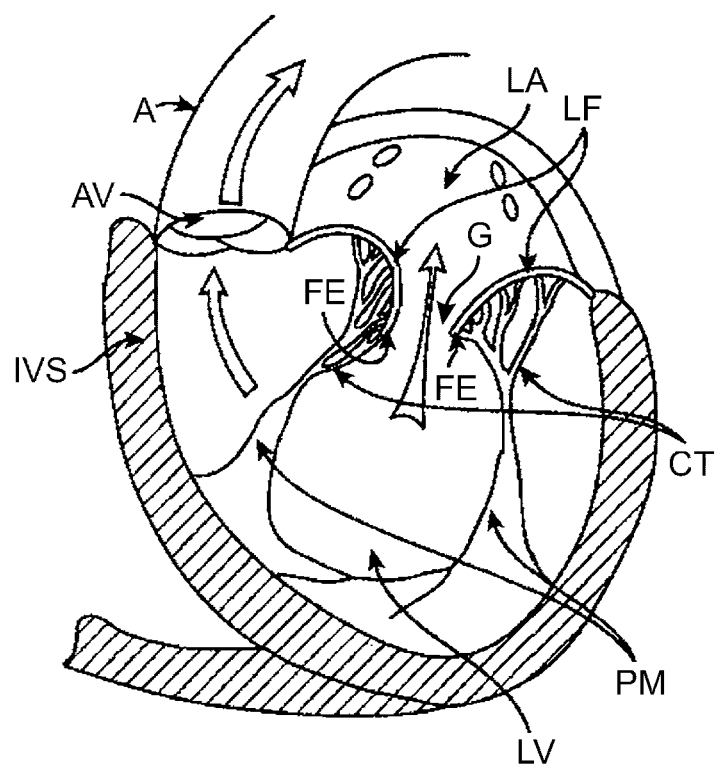
FIG. 1C is a schematic illustration of a heart in a patient suffering from cardiomyopathy, and which is suitable for treatment with systems in accordance with embodiments of the present technology.

FIGS. 1B to 1D show a number of structural defects in the heart can cause mitral valve regurgitation. Ruptured chordae RCT, as shown in FIG. 1B, can cause a valve leaflet LF2 to prolapse since inadequate tension is transmitted to the leaflet via the chordae. While the other leaflet LF 1 maintains a normal profile, the two valve leaflets do not properly meet and leakage from the left ventricle LV into the left atrium LA will occur, as shown by the arrow.

Regurgitation also occurs in patients suffering from cardiomyopathy where the heart is dilated and the increased size prevents the valve leaflets LF from meeting properly, as shown in FIG. 1C. The enlargement of the heart causes the mitral annulus to become enlarged, making it impossible for the free edges FE to meet during systole. The free edges of the anterior and posterior leaflets normally meet along a line of coaptation C as shown in FIG. 1C-1, but a significant gap G can be left in patients suffering from cardiomyopathy, as shown in FIG. 1C-2.

FIG. 1D shows an impaired mitral valve. Mitral valve regurgitation can also occur in patients who have suffered ischemic heart disease where the functioning of the papillary muscles PM is impaired. As the left ventricle LV contracts during systole, the papillary muscles PM do not contract sufficiently to effect proper closure. One or both of the leaflets LF1 and LF2 then prolapse, as illustrated. Leakage again occurs from the left ventricle LV to the left atrium LA, as shown by the arrow.

FIGS. 1C-1, 1C-2, and 1E illustrate the shape and relative sizes of the leaflets L of the mitral valve. It may be seen that the overall valve has a generally kidney-like shape, with a long axis MVA1 and a short axis MVA2. In healthy humans the long axis MVA1 is typically within a range from about 33.3 mm to about 42.5 mm in length (37.9+/−4.6 mm), and the short axis MVA2 is within a range from about 26.9 mm to about 38.1 mm in length (32.5+/−5.6 mm). However, with patients having decreased cardiac function these values can be larger, for example MVA1 can be within a range from about 45 mm to 55 mm and MVA2 can be within a range from about 35 mm to about 40 mm. The line of coaptation C is curved or C-shaped, thereby defining a relatively large anterior leaflet AL and substantially smaller posterior leaflet PL (FIG. 1C-1). Both leaflets can be generally crescent-shaped from the superior or atrial side, with the anterior leaflet AL being substantially wider in the middle of the valve than the posterior leaflet. At the opposing ends of the line of coaptation C the leaflets join together at corners called the anterolateral commissure AC and posteromedial commissure PC, respectively.

Figure 1E:
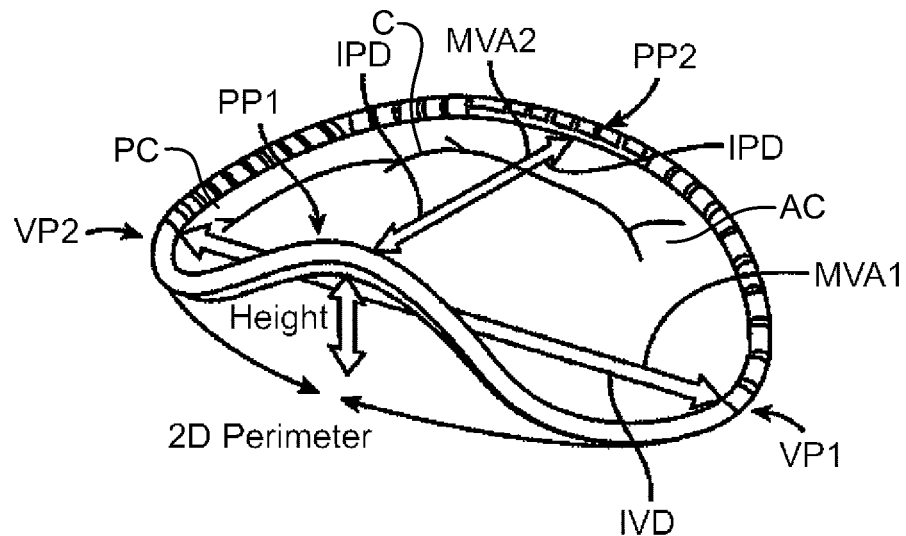
FIG. 1E is a schematic illustration of a native mitral valve of a heart showing dimensions of the annulus, and which is suitable for treatment with systems in accordance with embodiments of the present technology.

FIG. 1E shows the shape and dimensions of the annulus AN. The annulus AN is an annular area around the circumference of the valve and may comprise a saddle-like shape with a first peak portion PP1 and a second peak portion PP2 located along an interpeak axis IPD, and a first valley portion VP1 and a second valley portion VP2 located along an intervalley axis IVD. The first and second peak portions PP1 and PP2 are higher in elevation relative to a plane containing the nadirs of the two valley portions VP1, VP2, typically being about 8 mm to about 19 mm higher in humans, thus giving the valve an overall saddle-like shape. The distance between the first and second peak portions PP1, PP2, referred to as interpeak span IPD, is substantially shorter than the intervalley span IVD, the distance between first and second valley portions VP1, VP2. The dimensions and physiology of the patient may vary among patients, and although some patients may comprise differing physiology, the teachings as described herein can be adapted for use by many patients having various conditions, dimensions and shapes of anatomical structures. For example, some patients may have a long dimension across the annulus and a short dimension across the annulus of the mitral valve without well defined peak and valley portions, and the methods and apparatus as described herein can be configured accordingly.

Access to the Delivery Sites

Access to treatment sites can be provided by various techniques and procedures. For example, minimally invasive surgery techniques, laparoscopic procedures, and/or open surgical procedures can provide access to treatment sites in the heart. In procedures targeting valves, minimally invasive surgery techniques may be percutaneous procedures in which access can be accomplished through the patient's vasculature. Percutaneous procedures refer to procedures in which a location of the vasculature remote from the heart is accessed through the skin, often using a surgical cut down procedure or a minimally invasive procedure, such as using needle access through, for example, the Seldinger technique. The ability to percutaneously access remote vasculature is well-known and described in patent literature and medical literature. For example, the approach to a mitral valve may be antegrade and may rely on entry into the left atrium by crossing the interatrial septum. Alternatively, the approach to the mitral valve can be retrograde where the left ventricle is entered through the aortic valve.

Figure 1F:
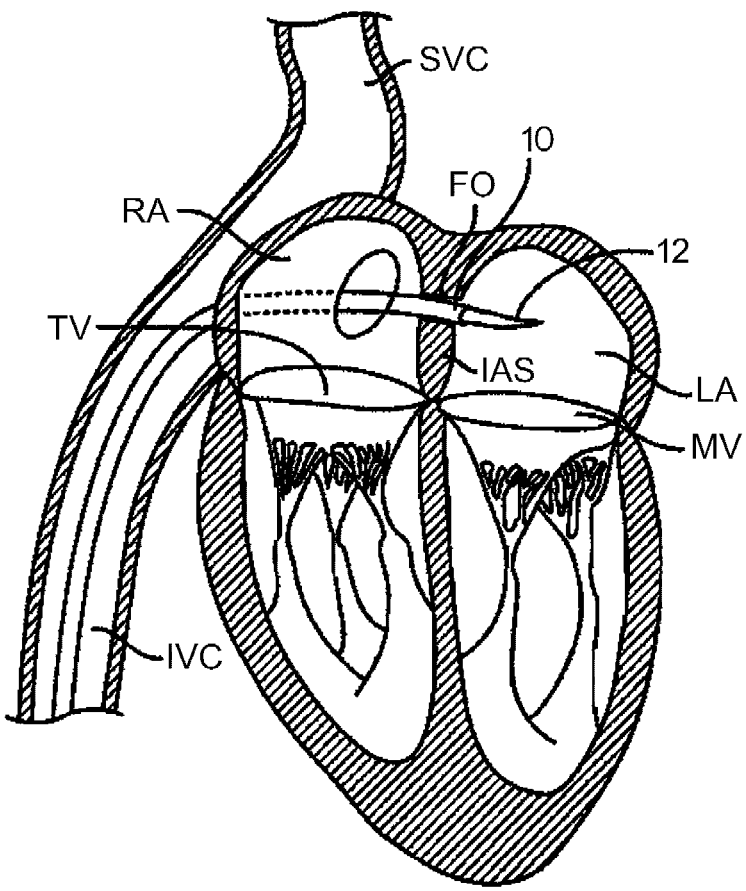
FIG. 1F is a schematic cross-sectional illustration of the heart showing an antegrade approach to the native mitral valve from the venous vasculature in accordance with various embodiments of the present technology.

Using a transseptal approach, access to the mitral valve can be obtained via the inferior vena cava IVC or superior vena cava SVC, through the right atrium RA, across the interatrial septum IAS and into the left atrium LA above the mitral valve MV. As shown in FIG. 1F, a catheter 10 having a needle 12 may be advanced from the inferior vena cava IVC into the right atrium RA. Once the catheter 10 reaches the anterior side of the interatrial septum IAS, the needle 12 may be advanced so that it penetrates through the septum, for example at the fossa ovalis FO or the foramen ovale into the left atrium LA. At this point, a guidewire may be exchanged for the needle 12 and the catheter 10 withdrawn.

Figure 1G:
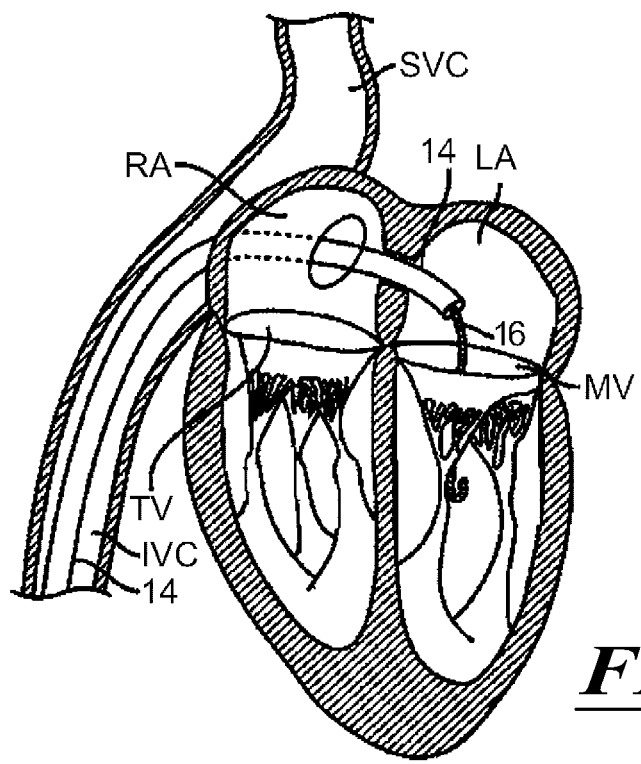
FIG. 1G is a schematic cross-sectional illustration of the heart showing access through the interatrial septum (IAS) maintained by the placement of a guide catheter over a guidewire in accordance with various embodiments of the present technology.

As shown in FIG. 1G, access through the interatrial septum may usually be maintained by the placement of a guide catheter 14 (e.g., a steerable catheter, a guide sheath, etc.), typically over a guidewire 16 which has been placed as described above. The guide catheter 14 affords subsequent access to permit introduction of a catheter to treat the mitral valve, as described in more detail herein below.

The antegrade or transseptal approach to the mitral valve, as described above, can be advantageous in many respects. For example, the use of the antegrade approach may allow for more precise and effective centering and stabilization of the guide catheter and/or prosthetic device (e.g., a prosthetic heart valve). Precise positioning facilitates accuracy in the placement of the prosthetic valve apparatus. The antegrade approach may also reduce the risk of damaging the subvalvular apparatus during catheter and interventional tool introduction and manipulation. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 1H:
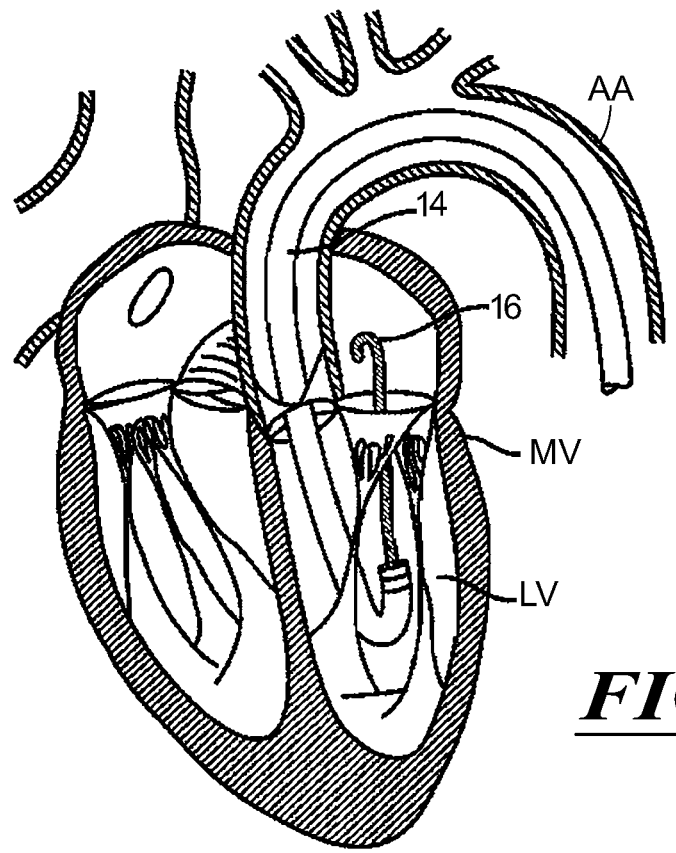
FIGS. 1H and 1I are schematic cross-sectional illustrations of the heart showing retrograde approaches to the native mitral valve through the aortic valve and arterial vasculature in accordance with various embodiments of the present technology.

An example of a retrograde approach to the mitral valve is illustrated in FIGS. 1H and H. The mitral valve MV may be accessed by an approach from the aortic arch AA, across the aortic valve AV, and into the left ventricle below the mitral valve MV. The aortic arch AA may be accessed through a conventional femoral artery access route, as well as through more direct approaches via the brachial artery, axillary artery, or a radial or carotid artery. Such access may be achieved with the use of a guidewire 16. Once in place, a guide catheter 14 may be tracked over the guidewire 16 (FIG. 1H). The guide catheter 14 affords subsequent access to permit placement of the prosthetic device, as described in more detail below. In some instances, a retrograde arterial approach to the mitral valve can be preferred due to its advantages. Use of the retrograde approach can eliminate the need for a trans-septal puncture. The retrograde approach is also commonly used by cardiologists and thus has the advantage of familiarity.

Figure 1I:
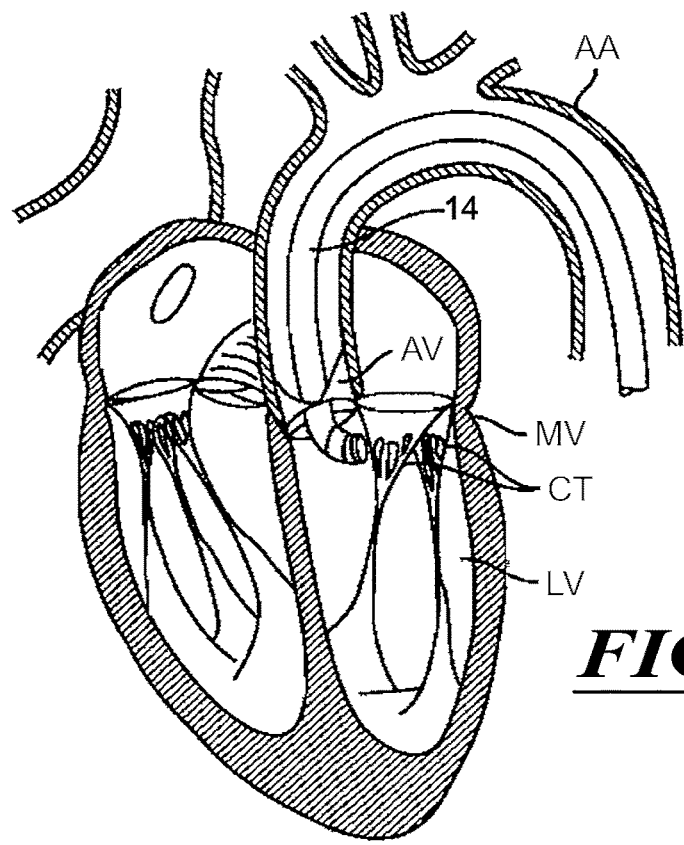
Figure 1J:
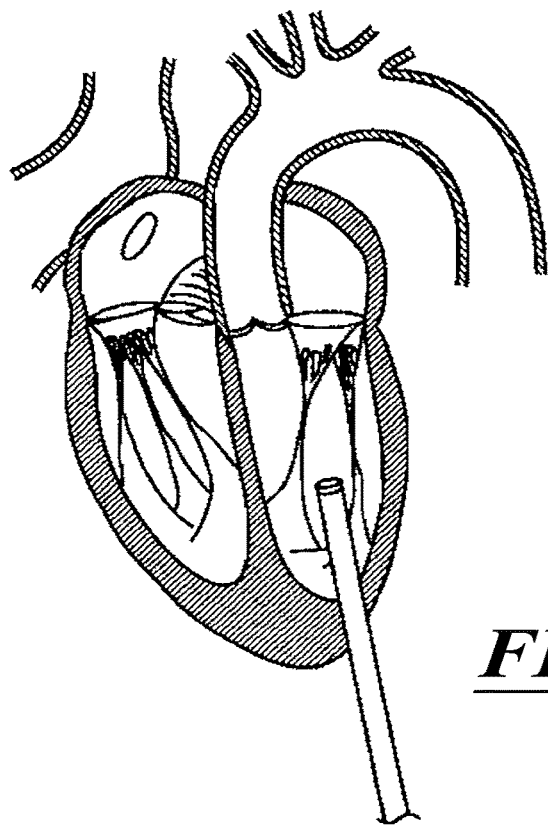
FIG. 1J is a schematic cross-sectional illustration of the heart showing an approach to the native mitral valve using a trans-apical puncture in accordance with various embodiments of the present technology.

An additional approach to the mitral valve is via transapical puncture, as shown in FIG. 1J. In this approach, access to the heart can be gained via thoracic incision, which can be a conventional open thoracotomy or sternotomy, or a smaller intercostal or sub-xyphoid incision or puncture. An access device (e.g., a cannula, a guide catheter, etc.) is then placed through a puncture, sealed by a purse-string suture, in the wall of the left ventricle near the apex of the heart. The catheters and prosthetic devices disclosed herein may then be introduced into the left ventricle through this access cannula. The trans-apical approach can have the advantage of providing a shorter, straighter, and more direct path to the mitral valve or aortic valve. Further, because it does not involve intravascular access, it can be performed by surgeons who may not have the necessary training in interventional cardiology to perform the catheterizations of other percutaneous approaches.

Once access to the valve is achieved, the interventional tools and catheters may be advanced to the heart intravascularly and positioned adjacent the target cardiac valve in a variety of manners. In some embodiments, access to a delivery site can be through the chest of the patient and may be provided by, for example, conventional transthoracic surgical approaches, open and semi-open heart procedures, laparoscopic techniques, and port access techniques. Such surgical access and procedures can utilize conventional surgical instruments, including, for example, retractors, rib spreaders, trocars, laparoscopic instruments, forceps, scissors, shears, rongeurs, fixation devices (e.g., clip appliers, clamps, etc.), staplers, sutures, needle holders, cauterizing instruments, electrosurgical pens, suction apparatuses, approximators, and/or the like.

At least some catheters disclosed herein can deploy prosthetic devices as an adjunct to a surgical heart procedure (e.g., coronary artery bypass surgery, replacing and/or repairing portions of the heart, etc.), such that one or more prosthetic devices can be delivered without performing additional complicated procedures for gaining access to the treatment site. For example, in one surgical procedure, a heart valve repair procedure (e.g., aortic valve repair, mitral valve repair, pulmonary valve repair, etc.) may be performed on one valve and valve replacement may be performed on another heart valve (e.g., a diseased aortic valve, a mitral valve, a pulmonary valve, etc.).

The catheters and/or prosthetic devices disclosed herein may be configured for a particular approach or interchangeable among approaches. A person of ordinary skill in the art can identify an appropriate approach for an individual patient and design the treatment apparatus for the identified approach in accordance with embodiments described herein. For example, an intravascular catheter can be flexible, while a transapical catheter can be generally rigid. The properties, dimensions (e.g., width, length, etc.), and configuration of the catheter can be selected based on the delivery approach. In some embodiments, the catheter can include one or more lumens for aspirating fluid (e.g., air, blood, etc.) from a delivery capsule. In some procedures, the lumens can be used to de-air the catheter prior to introduction to the patient's body.

A wide range of surgical instruments can be used to access the heart, perform surgical procedures on the heart, and assist in operation of a catheter capable of delivering a prosthetic device in the heart. Such surgical instruments include, without limitation, sizing rings, balloons, calipers, gages, and other surgical tools can be selected based on, for example, desired access path, dimensions and configuration of the delivery apparatuses, and an anatomical structure of the heart. Orientation and steering of the treatment apparatuses (e.g., catheters) can be combined with many known catheters, tools, and devices. Such orientation may be accomplished by gross steering of the treatment apparatus to the desired location and then refined steering of the components of the treatment apparatus to achieve a desired result.

Steering may be accomplished by a number of suitable methods. For example, a steerable guidewire may be used to introduce a guide catheter and a catheter for delivering a prosthetic device into the proper position. The guide catheter may be introduced, for example, using a surgical cut down or Seldinger access to the femoral artery in the patient's groin. After placing a guidewire, the guide catheter may be introduced over the guidewire to the desired position. Alternatively, a shorter and differently shaped guide catheter could be introduced through the other routes described above.

A guide catheter may be pre-shaped to provide a desired orientation relative to the treatment site. For access to the native mitral valve via the trans-septal approach, the guide catheter may have a curved shape, an angled configuration, or other suitable shape at its tip to orient the distal end toward the mitral valve from the location of the septal puncture through which the guide catheter extends. For the retrograde approach, as shown in FIGS. 1H and 1I, guide catheter 14 may have a pre-shaped J-tip which is configured so that it turns toward the mitral valve MV after it is placed over the aortic arch AA and through the aortic valve AV. As shown in FIG. 1H, the guide catheter 14 may be configured to extend down into the left ventricle LV and to evert so that the orientation of an interventional tool or catheter is more closely aligned with the axis of the mitral valve MV. In either case, a pre-shaped guide catheter may be configured to be straightened for endovascular delivery by means of a stylet or stiff guidewire which is passed through a lumen of the guide catheter. The guide catheter might also have pull-wires or other features to adjust its shape for more fine steering adjustment.

Treatment of Cardiac Valves

Figure 2A:
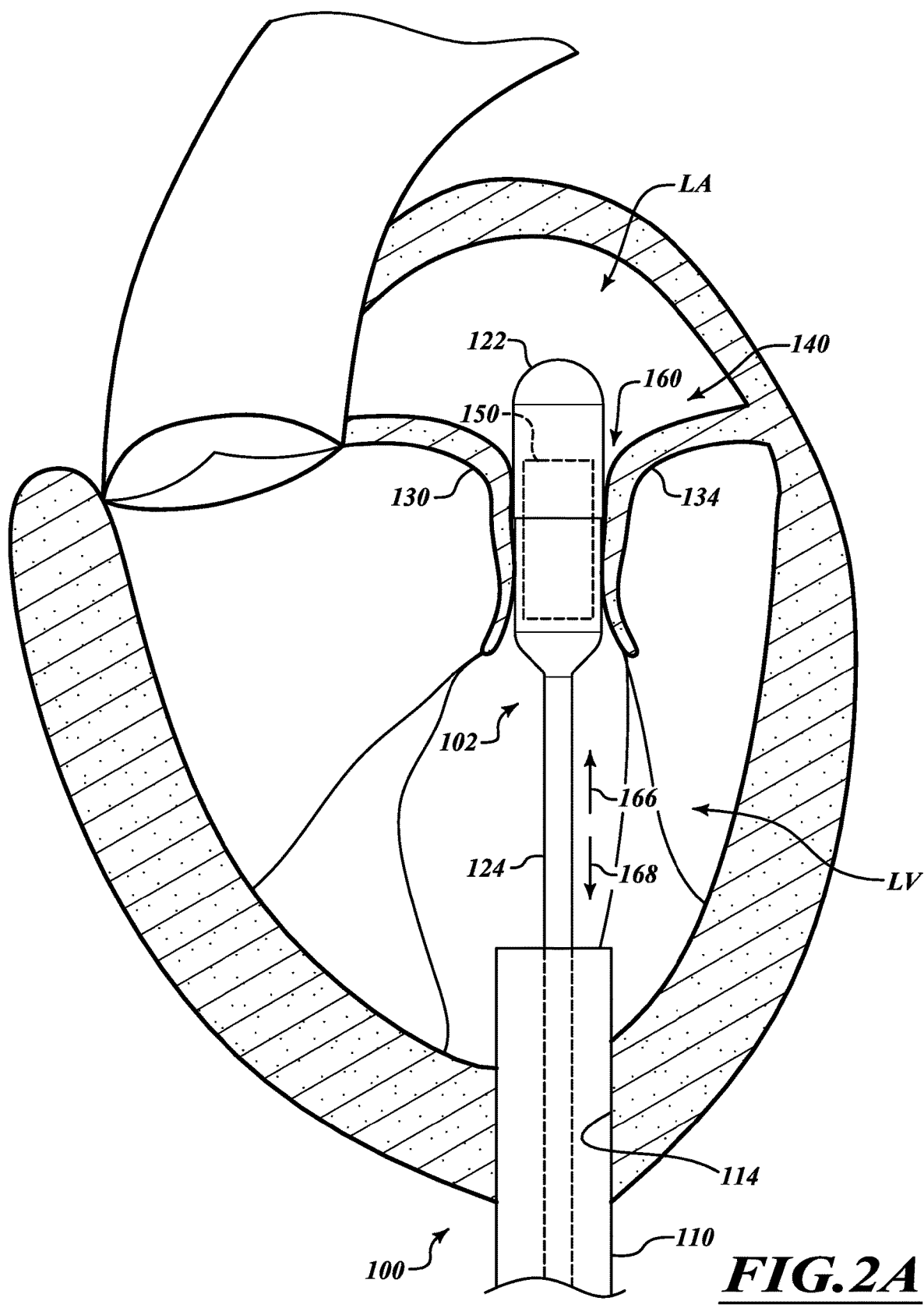
FIG. 2A is a schematic cross-sectional illustration of the heart and a delivery capsule positioned in a native mitral valve of the heart in accordance with various embodiments of the present technology.
Figure 2B:
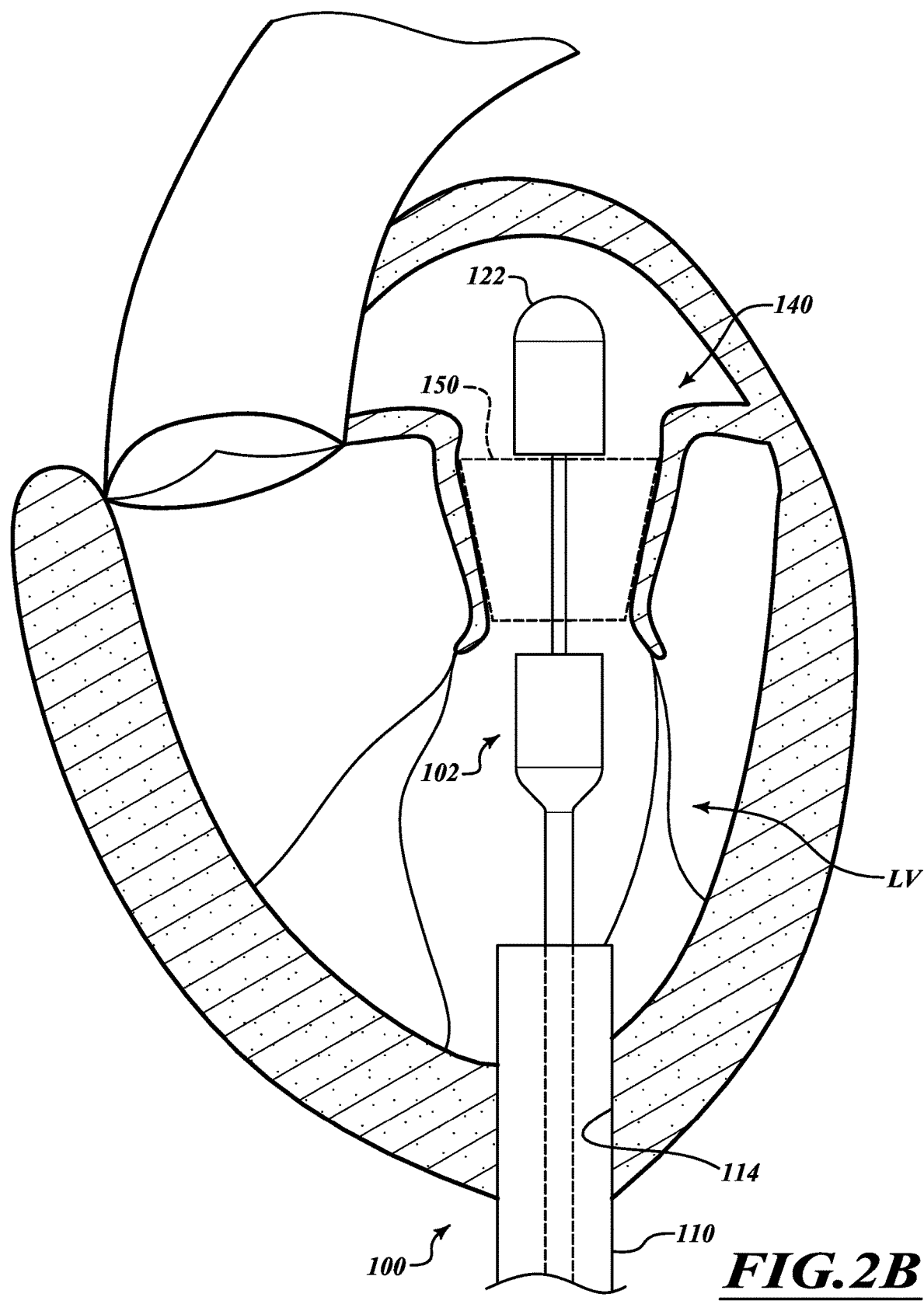
FIG. 2B shows the delivery capsule of FIG. 2A in a deployment configuration and a deployed prosthetic device in accordance with various embodiments of the present technology.

FIG. 2A is a schematic cross-sectional illustration of a heart and a delivery capsule of a catheter delivered via a trans-apical approach to the mitral valve. FIG. 2B shows the delivery capsule in a deployment configuration and a deployed prosthetic device. Referring first to FIG. 2A, a system 100 can include a guide catheter 110 and a catheter 102 extending through the guide catheter 110. The guide catheter 110 is positioned in a trans-apical opening 114 to provide access to the left ventricle LV. The catheter 102 can include a hydraulically actuatable delivery capsule 122 ("delivery capsule 122") and an elongated catheter body 124 ("catheter body 124"). The delivery capsule 122 may be positioned between a posterior leaflet 130 and an anterior leaflet 134 of a mitral valve 140. The catheter body 124 can be conveniently moved in the superior direction (as indicated by arrow 166) and the inferior direction (as indicated by arrow 168) to position the delivery capsule 122 at a desired location within an opening 160 of the mitral valve 140.

The delivery capsule 122 can be hydraulically driven from a containment configuration (FIG. 2A) towards a deployment configuration (FIG. 2B) to deploy a prosthetic device 150, such as a prosthetic heart valve (the prosthetic device 150 is shown schematically in dashed lines). The delivery capsule 122 is expected to reduce, limit, or substantially eliminate uncontrolled movement of the prosthetic device 150 caused by forces associated with expansion of the prosthetic device 150. Such uncontrolled movement can include, for example, axial jumping, self-ejection, or other types of uncontrolled movement. For example, the delivery capsule 122 is expected to inhibit or prevent translation of the prosthetic device 150 while at least a portion of the prosthetic device 150 expands to contact the treatment site.

A biasing force provided by a biasing device can limit or substantially prevent opening of the delivery capsule 122 attributable to the forces produced by the prosthetic device 150. For example, an unsheathed portion of the prosthetic device 150 can expand outwardly from the partially opened delivery capsule 122 while the biasing device inhibits further opening of the delivery capsule 122. In some embodiments, for example, the delivery capsule 122 can be hydraulically driven towards the deployment configuration in a controlled manner to deploy the prosthetic device 150 at the treatment site. Further details regarding the delivery capsule 122 are provided below.

Referring to FIG. 2B, the prosthetic device 150 is in a deployed configuration. The opened delivery capsule 122 can now be moved back to the containment configuration and moved proximally through the deployed prosthetic device 150. The catheter 102 can be pulled proximally through the guide catheter 110 and removed from the patient. The catheter 102 can then be used to deliver additional prosthetic devices or it can be discarded.

Figure 3:
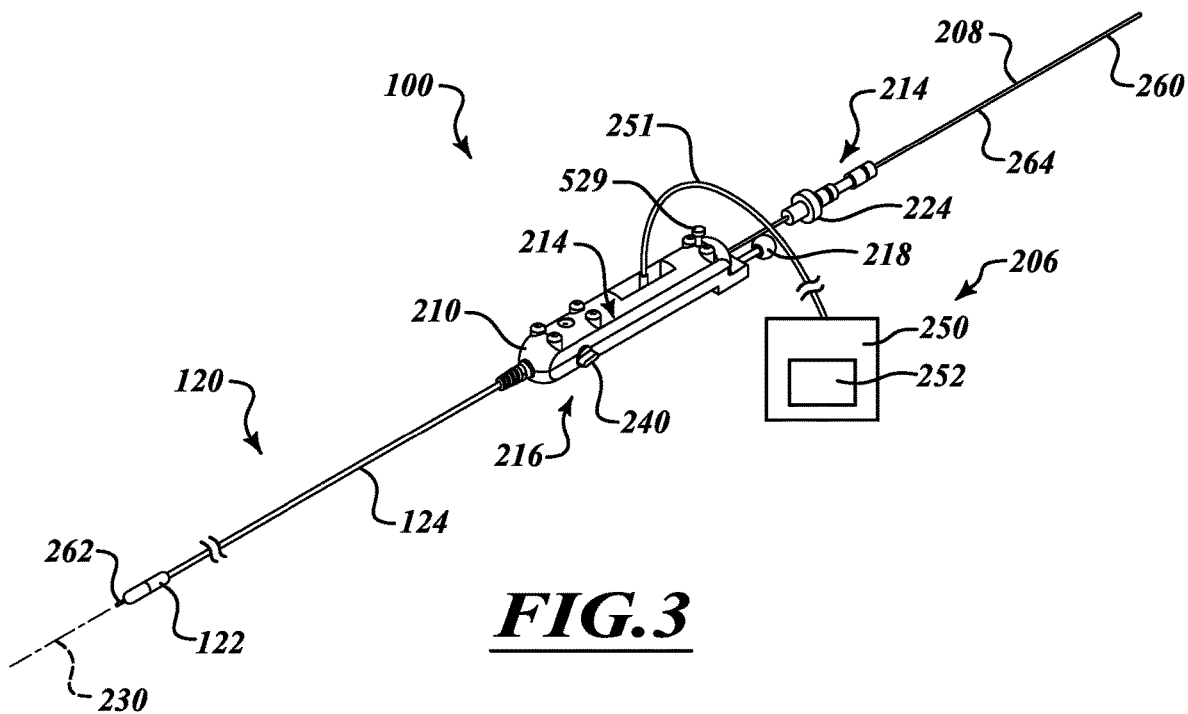
FIG. 3 is an isometric view of a system for delivering prosthetic devices configured in accordance with various embodiments of the present technology.

FIG. 3 is an isometric view of the system 100 including the catheter 102, a guidewire 208, and a fluid system 206. The fluid system 206 is configured to deliver fluid to the catheter 102 to hydraulically operate the delivery capsule 122. The catheter 102 can include a handheld control unit 210 ("control unit 210") configured to provide steering capability (e.g., 360 degree rotation of the delivery capsule 122, 180 degree rotation of the delivery capsule 122, 3-axis steering, 2-axis steering, etc.). In some embodiments, for example, the control unit 210 can include a rotational control assembly 214 ("control assembly 214") and a steering mechanism 216. A knob 224 of the control assembly 214 can be rotated to rotate the delivery capsule 122 about its longitudinal axis 230. A knob assembly 240 of the steering mechanism 216 can be used to steer the catheter 102 by bending a distal portion thereof about a transverse axis. In other embodiments, the control unit 210 may include different features and/or have a different arrangement.

The fluid system 206 can include a fluid source 250 and a line 251 coupling the fluid source 250 to the catheter 102. The fluid source 250 may contain a flowable substance (e.g., water, saline, etc.) and can include, without limitation, one or more pressurization devices, fluid connectors, fittings, valves, or other fluidic components. The pressurization devices, for example, can include a pump (e.g., a positive displacement pump, a plunger pump, etc.), a syringe pump (e.g., a manually operated syringe pump), or other devices capable of pressurizing the flowable substance. The line 251 can include, without limitation, one or more hoses, tubes, or other components (e.g., connectors, valves, etc.) through which the flowable substance can pass.

In some embodiments, the fluid source 250 may comprise a controller 252 including, without limitation, one or more computers, central processing units, processing devices, microprocessors, digital signal processors (DSPs), and/or application-specific integrated circuits (ASICs). To store information, for example, the controller 252 can include, without limitation, one or more storage elements, such as volatile memory, non-volatile memory, read-only memory (ROM), and/or random access memory (RAM). The stored information can include, pumping programs, patient information, and/or executable programs. The controller 252 can further include a manual input device (e.g., a keyboard, a touch screen, etc.) or an automated input device (e.g., a computer, a data storage device, servers, network, etc.). In still other embodiments, the controller 252 may include different features and/or have a different arrangement.

FIG. 3 shows the catheter 102 traveling over the guidewire 208. The guidewire 208 includes a proximal portion 260, a distal portion 262, and a main body 264. The proximal portion 260 extends proximally from the control assembly 214, and the distal portion 262 extends distally past the delivery capsule 122. As discussed in greater detail below with reference to FIG. 11, the guidewire 208 can be used to guide the delivery capsule 122 into the native heart valve.

Figure 4:
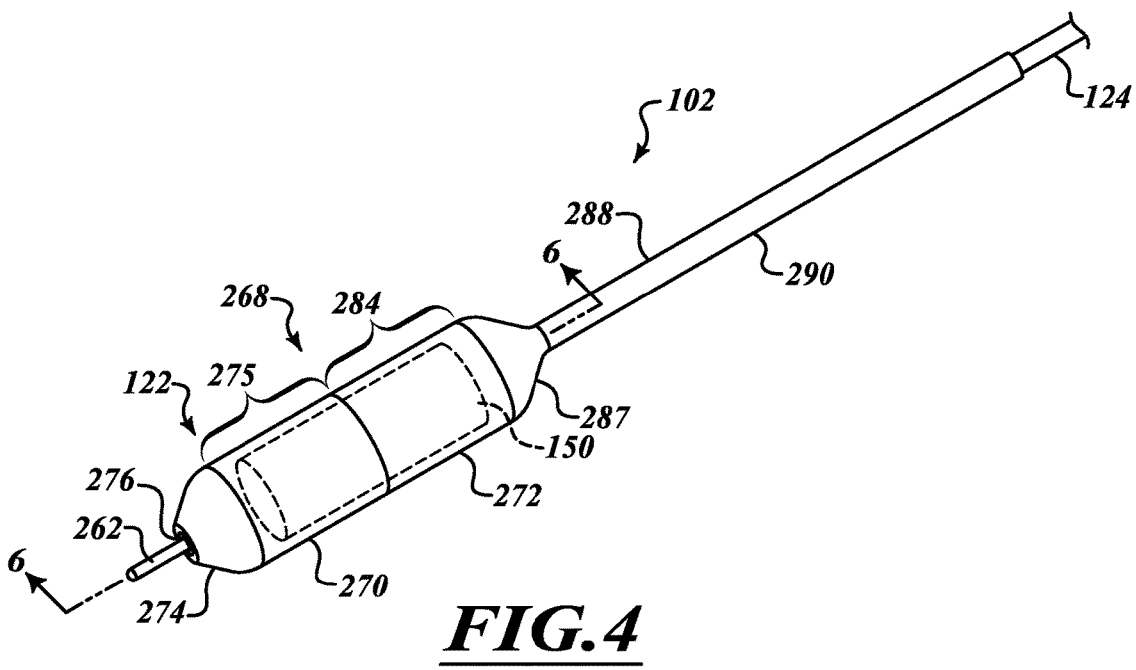
FIG. 4 is an isometric view of a distal portion of the system of FIG. 3.

FIG. 4 is an isometric view of a distal portion of the catheter 102 configured in accordance with various embodiments of the present technology. The delivery capsule 122, for example, can include a housing 268 configured to hold the prosthetic device 150 (shown schematically in broken lines). The housing 268 can include a distal sheath 270 and a proximal sheath 272. The distal sheath 270 can include a closed distal end 274 and a distal containment portion 275. The distal end 274 can have a guidewire-receiving opening 276 and can have an atraumatic configuration (e.g., a substantially partially spherical shape, blunt configuration, rounded configuration, etc.) to limit or prevent injury or trauma to tissue. The distal containment portion 275 can contain a distal portion of the prosthetic device 150.

The proximal sheath 272 can include a proximal containment portion 284, a tapered portion 287, and a guide portion 290. The proximal containment portion 284 can contain a proximal portion of the prosthetic device 150 and can mate with the distal containment portion 275. The tapered portion 287 can have a frusto-conical shape, a partially spherical shape, or other suitable configuration for substantially preventing or limiting injury or trauma to tissue when the delivery capsule 122 is pulled proximally through the subject. The guide portion 290 can closely surround the catheter body 124.

The distal sheath 270 and/or proximal sheath 272 can be made, in whole or in part, of metal, polymers, plastic, composites, combinations thereof, or other materials capable of holding the prosthetic device 150. In some embodiments, the distal containment portion 275 can be a tubular member (e.g., a tubular portion with a generally circular cross section, a generally elliptical cross section, etc.) made of metal or other rigid materials. In some embodiments, the distal sheath 270 or proximal sheath 272 can be configured to contain the entire valve prosthetic device 150.

Figure 5:
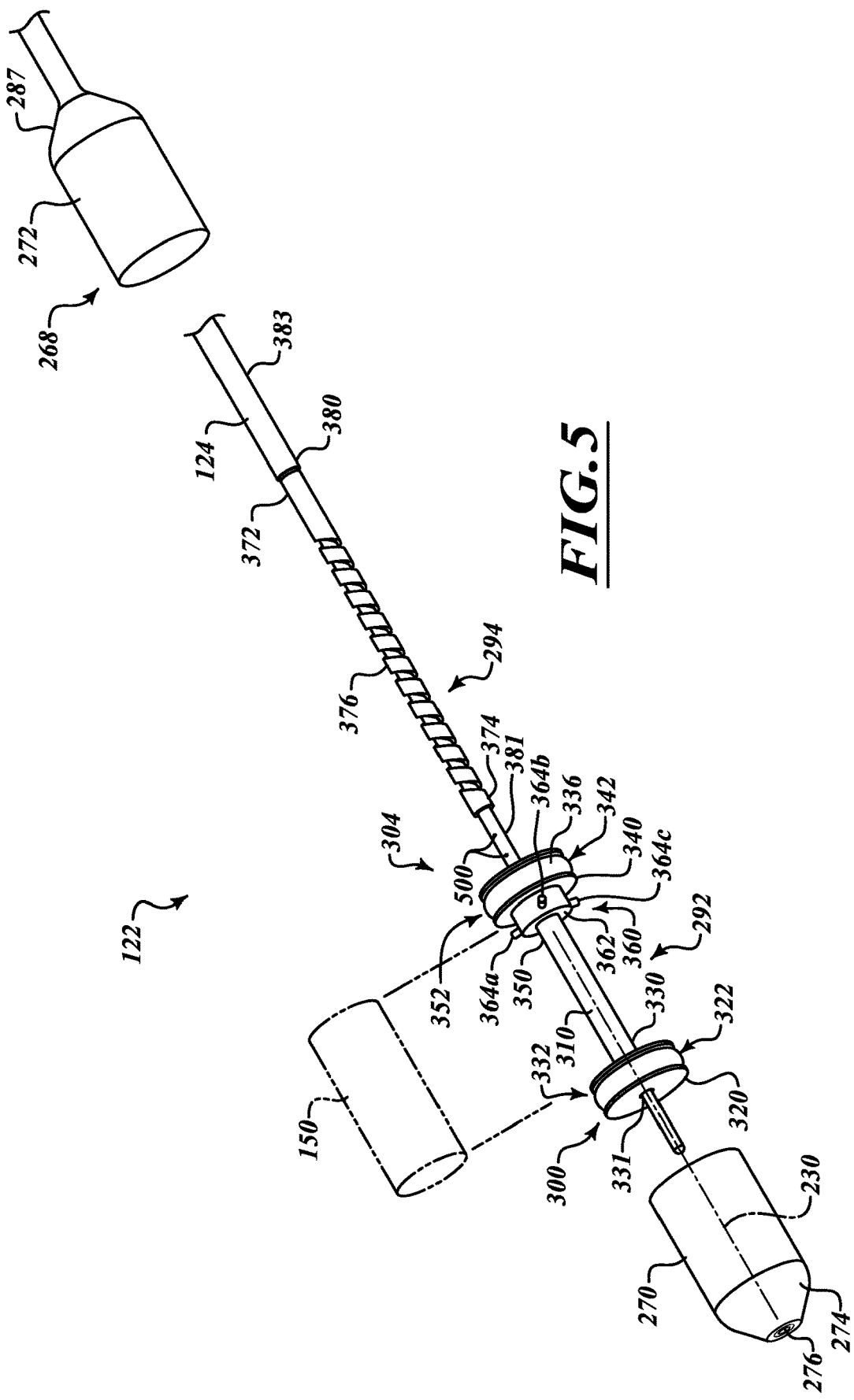
FIG. 5 is an exploded isometric view of the distal portion of FIG. 4 in accordance with various embodiments of the present technology.

FIG. 5 is an exploded isometric view of the distal portion of the catheter 102. As best seen in FIG. 5, the delivery capsule 122 can include a piston device 292 and a biasing device 294. The piston device 292 can include a distal head assembly 300, a proximal head assembly 304, and a connector 310. The connector 310 can include ends 330, 350 connected to the distal and proximal head assemblies 300, 304, respectively.

The distal head assembly 300 can include a head 320 and a sealing member 322. The head 320 can include a through-hole 331 and a channel 332 for receiving the sealing member 322. The proximal head assembly 304 can include a head 340 and a sealing member 342. The head 340 can include a channel 352 for receiving the sealing member 342 and a holder 360.

The holder 360 is configured to retain the prosthetic device 150 and can include a hub 362 and retaining features in the form of posts 364a, 364b, 364c (collectively "posts 364"). The posts 364 are circumferentially spaced apart about the hub 362. In the illustrated embodiment, the three posts 364 extend radially outward. In other embodiments, however, the number of posts 364 can be increased or decreased and the posts 364 may be arranged evenly or unevenly about the hub 362. When the prosthetic device 150 is in a delivery configuration (e.g., a collapsed state, an undeployed state, etc.), the posts 364 can pass through receiving features (e.g., openings, holes, eyelets, etc.) of the prosthetic device 150 to inhibit, prevent, or substantially eliminate movement of the prosthetic device 150 along the longitudinal axis 230 of the delivery capsule 122.

When being deployed, prosthetic device 150 can radially expand along the posts 364 to move towards a deployed configuration (e.g., an expanded configuration). For example, in some embodiments the prosthetic device 150 can move past the ends of the posts 364 to disengage the delivery capsule 122 under its own spring load. In other embodiments, the posts 364 can be moved inwardly into the hub 362 to release the prosthetic device 150. The holder 360 can also include one or more retaining features in the form of hooks, clamps, or other types of features capable of holding and releasing a prosthetic device. In other embodiments, the posts 364 may have a different arrangement relative to the prosthetic device 150.

The sealing members 322 and 342 are positioned to engage the distal and proximal sheaths 270 and 272, respectively, and can be made, in whole or in part, of silicon, rubber, polymers, elastomers, combinations thereof, or other compliant materials suitable for forming seals. In some embodiments, one or both sealing members 322, 342 are gaskets or O-rings made, in whole or in part, of rubber. In yet other embodiments, the sealing members 322, 342 can be bladder seals. Other types of sealing members 322, 342 can be used, if needed or desired.

FIG. 5 shows the biasing device 294 carried by the catheter body 124. As used herein, the term "biasing device" refers generally to one or more biasing members, such as linear springs, non-linear springs, or other devices capable of providing a biasing force. In some embodiments, for example, the biasing device 294 may comprise a linear spring for deploying a prosthetic device 150 that produces a substantially constant deployment forces. In other embodiments, the biasing device 294 may comprise a non-linear spring for deploying a prosthetic device 150 that produces varying deployment forces. The biasing device 294 can be made of metal, polymers, or combinations thereof. In metal embodiments, the biasing device 294 can be made, in whole or in part, of steel (e.g., spring steel), nickel titanium (e.g., nitinol), or other alloys. In one particular embodiment, for example, the biasing device 294 is a helical spring made of nitinol. In yet another embodiment, the biasing device 294 is a metal hypotube that has been cut (e.g., laser cut) in a spiral pattern. The biasing device 294 can have a proximal end 372, a distal end 374, and a main body 376. The proximal end 372 can be adjacent a shoulder 380 of the catheter body 124. The catheter body 124 can include a narrowed portion 381 extending through the biasing device 294 and a widened portion 383. The widened portion 383 defines the shoulder 380. The catheter body 124 can be made, in whole or in part, of plastic, thermoplastic elastomers (e.g., resins such as Pebax®), or other flexible materials. In some embodiments, the catheter body 124 can be generally rigid for delivery using, for example, a transapical approach.

FIG. 6 is a partially schematic cross-sectional view of the distal position of the catheter 102 configured in accordance with various embodiments of the present technology. The distal sheath 270, the proximal sheath 272, and the head assemblies 300, 304 cooperate to define a containment or main chamber 400. The containment chamber 400 is configured to contain the prosthetic device 150. Equal parts of the containment chamber 400 may be disposed in the distal sheath 270 and proximal sheath 272, or the containment chamber 400 may have a larger portion or even its entirety contained in either the distal or proximal sheath. The sealing member 322 is positioned to sealingly engage the distal sheath 270 to form a fluid chamber 410 (e.g., a fluidically sealed chamber or an isolated fluid chamber). The sealing member 342 is positioned to sealingly engage the proximal sheath 272 to form a fluid chamber 412. The fluid chambers 410, 412 can be fluidically sealed from the containment chamber 400. A flowable substance can be delivered into the fluid chamber 410 to move the distal sheath 270 in the distal direction (indicated by arrow 416) to unsheathe an upstream or atrial portion 424 of the prosthetic device 150. Fluid can be delivered into the fluid chamber 412 to move the proximal sheath 272 in the proximal direction (indicated by arrow 418) to unsheathe a downstream or ventricular end or portion 426 of the prosthetic device 150.

The distal end 274 of the distal sheath 270 can include a wall 440 and a passageway 444. A rod 450 can be positioned in at least a portion of the passageway 444. The rod 450 can include, for example, a distal end 451 coupled to the distal sheath 270 and a retaining head 530 positioned in a lumen 454 of the piston device 294. Although not illustrated, the rod 450 can be hollow to receive a guidewire. The distal containment portion 275 includes a proximal open end 432 and a cylindrical sidewall 460. The cylindrical sidewall 460 can include an inner surface 462 and an outer surface 464. The sealing member 322 can physically contact the inner surface 462 to form a seal (e.g., an airtight seal, a fluid-tight seal, etc.).

As best seen in FIG. 6, the proximal containment portion 284 of the proximal sheath 272 can include a distal open end 470 and a closed proximal end 472. The distal open end 470 is received by the proximal open end 432 of the distal sheath 270. In some embodiments, a seal may be formed by the distal open end 470 and the proximal open end 432. The guide portion 290 of the proximal sheath 272 has a sidewall 488 that defines a lumen 490. The proximal sheath 272 can further include a stop 496 extending inwardly into the lumen 490. When the proximal sheath 272 is moved proximally (as indicated by arrow 418), the stop 496 can contact the biasing device 294.

The narrowed portion 381 of the catheter body 124 extends through the biasing device 294 and can include one or more ports 500 (one port 500 is identified in FIG. 6). Fluid can flow along a fluid lumen 388, through the port(s) 500, and into the fluid chamber 412. The number, sizes, and positions of the ports 500 can be selected to achieve the desired flow of fluid into the fluid chamber 412. A seal between the stop 496 and the narrowed portion 381 and/or a seal 509 between the guide portion 290 and the widened portion 383 can help achieve the desired fluid pressure in the chamber 412.

Although not illustrated, the catheter body 124 can include multiple lumens. One fluid lumen, for example, can provide fluid communication with fluid chamber 410, and another fluid lumen can provide fluid communication with the fluid chamber 412. Fluid can be independently delivered into and removed from the respective fluid chambers 410, 412. In some embodiments, fluid at a first pressure can be delivered into the fluid chamber 410 to move the distal sheath 270. At the same or a different time, fluid at a second pressure can be delivered into the fluid chamber 412 to move the proximal sheath 272. The second pressure can be equal to or different from the first pressure.

FIG. 7 is a partially schematic cross-sectional view of the control unit 210 of FIG. 3. The control unit 210 can further include an articulation mechanism 218. The articulation mechanism 218 includes a slider assembly 519 and a coupler 520. The slider assembly 519 can include a rod 518 and a knob 521. The rod 518 can have external threads that threadably engage internal threads of a threaded retainer 527. A pull wire 523 can couple the coupler 520 to the catheter body 124 such that rotation of the knob 521 about an axis of rotation 525 causes axial movement of the rod 518. The rod 518 can be moved distally or proximally to decrease or increase, respectively, the tension in the pull wire 523 to articulate the catheter 102. In some embodiments, the pull wire 523 can be tensioned to, for example, bend the catheter body 124 up or down. Alternatively, the pull wire 523 can be tensioned to bend or articulate the catheter body 124 in other directions.

A tubular member 531 can be coupled to the catheter body 124 and the knob 224 (FIG. 3). A locking feature 529 (e.g. a screw, a fastener, or the like) is configured to releasably engage the tubular member 531. For example, the locking feature 529 can be in a locked position to securely hold the tubular member 531 to prevent rotation of the catheter body 124. The locking feature 529 can be moved to an unlocked position to allow rotation of the tubular member 531 and the catheter body 124. In other embodiments, the locking feature 529 can have a different arrangement and/or different features.

FIG. 8 is a detailed cross-sectional view of a connector assembly 533 configured for use with the control unit of FIG. 7. The connector assembly 533, for example, can include a junction 534 and a swiveling member 538. The junction 534 is configured to fluidically couple the line 251 to the catheter body 124. The line 251 is coupled to an inlet 537 of the junction 534. The swiveling member 538 can rotatably couples the catheter body 124 to a housing 517.

FIG. 9 is a cross-sectional view of the control unit 210 with knob assemblies 240a, 240b (collectively "knob assemblies 240") taken along line 9-9 of FIG. 7. The knob assemblies 240 can be operated to move the delivery capsule 122. For example, the knob assembly 240a can be rotated to move the delivery capsule 122 to the right, and the knob assembly 240b can be rotated to move the delivery capsule 122 to the left. The knob assemblies 240 can be used to bend the catheter body 124 to the left or right, while the articulation mechanism 218 can be used to move bend the catheter body 124 up or down. The knob assemblies 240 can be generally similar to each other and, accordingly, the description of one knob assembly applies equal to the other knob assembly, unless indicated otherwise. In other embodiments, the knob assemblies 240 may include different features and/or have a different arrangement to, for example, controllably move the catheter body 124 in opposite directions.

The knob assemblies 240a, 240b may be coupled to the catheter body 124 via pull wires 542a, 542b, respectively. The knob assembly 240a includes a knob 543a coupled to a pulley 545a. The wire 542a is wrapped around the pulley 545a such that rotation of the knob 543a can increase or decrease the length of the pull wire 542a extending from the pulley 545a. For example, the knob 543a can be rotated to wrap the wire 542a around the pulley 545a to increase the tension in the wire 542a. The knob 543a can be rotated in the opposite direction to unwind the wire 542a from the pulley 545a to decrease the tension in the wire 542a. The control unit 210 can further include a stress-relief feature 516 coupled to the housing 517. The stress-relief feature 516, for example, may be configured to surround the catheter body 124 and can be made of a flexible material. In other embodiments, however, the control unit 210 may not include the stress-relief feature 516 or the stress-relief feature 516 may include different features.

FIG. 10 is a cross-sectional view of the control assembly 214 of FIG. 3. The control assembly 214 can include a sealing assembly 548 and the knob 224. The knob 224 can be fixedly coupled to the tubular member 531. The knob 224, for example, can be rotated about an axis of rotation 546 to cause corresponding rotation of the tubular member 531. In other embodiments, the control assembly 214 may include different features and/or have different features.

FIGS. 11-14 are a series of views of a method of deploying the prosthetic device 150. As described in greater detail below, the delivery capsule 122 is configured to be positioned within the patient's mitral valve 140. The distal sheath 270 can be hydraulically driven to unsheathe the atrial end 424 of the prosthetic device 150. The unsheathed atrial end 424 can move outwardly to engage the tissue of the mitral valve 140 while the delivery capsule 122 holds the ventricular end 426 of the prosthetic device 150. The proximal sheath 272 can be hydraulically driven to unsheathe the ventricular end 426 of the prosthetic device 150. The unsheathed ventricular end 426 can move outwardly to engage the tissue of the mitral valve 140.

Figure 11:
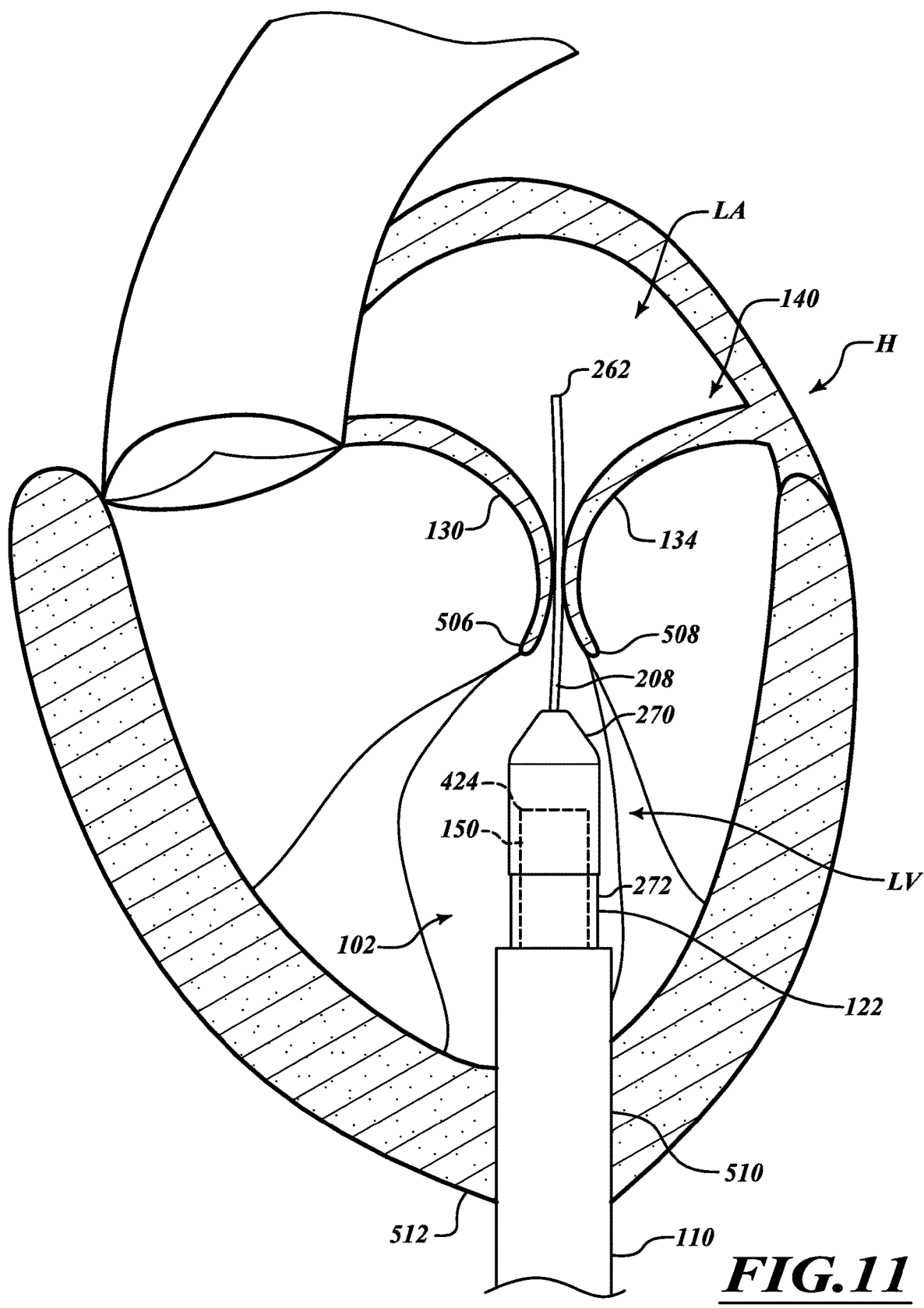
FIGS. 11-14 are a series of views of a method of deploying a prosthetic device from a delivery capsule in accordance with various embodiments of the present technology.

FIG. 11, for example, shows an opening 510 formed at the apex 512 of the heart H to access the left ventricle LV. The opening 510 can be an incision formed by, for example, a needle, a cutting tool, or a catheter (e.g., a needle catheter). The guide catheter 110 can be moved distally through the opening 510 and into the left ventricle LV. After the guide catheter 110 is positioned in the opening 510, the guidewire 208 can be moved through the guide catheter 110 and positioned between the posterior and anterior leaflets 130, 134. The distal portion 262 of the guidewire 208 can be moved into the left atrium LA. In some embodiments, the distal portion 262 can be an atraumatic tip (e.g., a flexible tip, a curved tip, a rounded tip, etc.) to prevent, inhibit, or substantially prevent injury to the heart tissue.

In the arrangement illustrated in FIG. 11, the delivery capsule 122 is ready to be moved between the posterior and anterior leaflets 130, 134. The delivery capsule 122 can be advanced over the guidewire 208 while the mitral valve 140 opens and closes. When the mitral valve 140 is closed (as shown in FIG. 11), the posterior and anterior leaflets 130, 134 can seal around the guidewire 208. Further, when the mitral valve 140 opens, the guidewire 208 can be conveniently advanced through the mitral valve 140.

Figure 12:
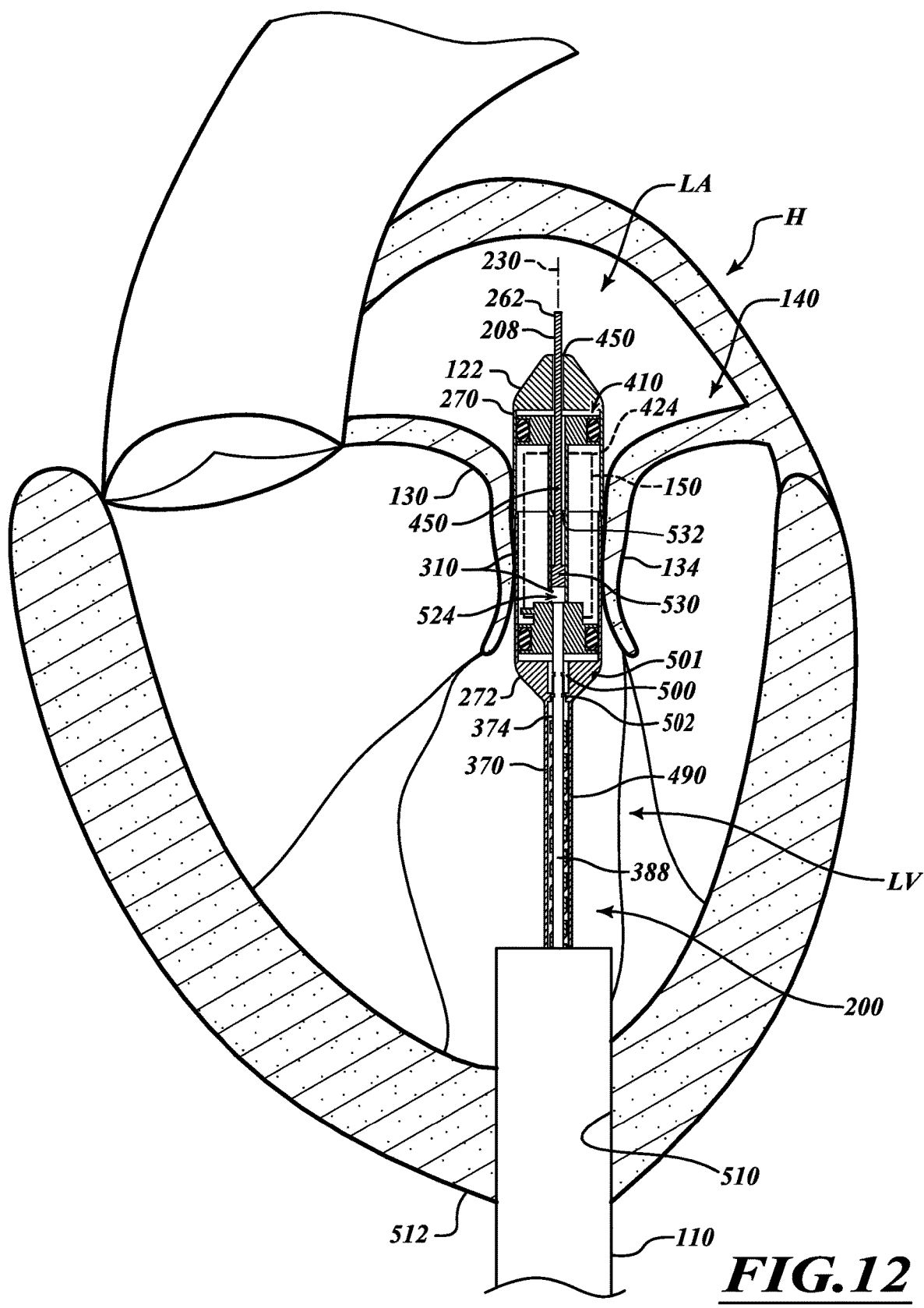

FIG. 12 shows the delivery capsule 122 positioned between the posterior and anterior leaflets 130, 134. A position indicator (e.g., in the form of a marker 501) may be carried on the proximal sheath 272. For example, the delivery capsule 122 can be rotated about its longitudinal axis 230 to align the marker 501 with the mitral valve 140. Markers can be located on an exterior surface of the distal sheath 270, on an exterior surface of the proximal sheath 272, within internal components of the delivery capsule 122, or at other suitable locations. In some embodiments, markers can be resonant markers for MR imaging-guided delivery. In yet further embodiments, markers can be echocardiographic markers viewable under echocardiography. Other types of markers can be used. In some procedures, a posterior side of the prosthetic device 150 can be aligned with the posterior leaflet 130 using a marker on a posterior side of the delivery capsule 122. Additionally or alternatively, a marker on an anterior side of the delivery capsule 122 can be used to align the anterior side of the delivery capsule 122 with the anterior leaflet 134.

FIG. 12 further illustrates the prosthetic device 150 ready to be deployed. For example, the fluid system 206 (FIG. 3) is configured to deliver fluid into the catheter 102, and the fluid can flow distally along the fluid lumens 388, 524 and into the chamber 410. The fluid fills the chamber 410 and causes movement of the distal sheath 270 in the distal direction. Friction, if any, between the prosthetic device 150 and the distal sheath 270 may cause pulling on the prosthetic device 150. However, the delivery capsule 122 is configured to hold the prosthetic device 150 to prevent, for example, inadvertent distal movement of the prosthetic device 150. The distal sheath 270 can be advanced distally until the head 530 contacts stops 532.

Figure 13:
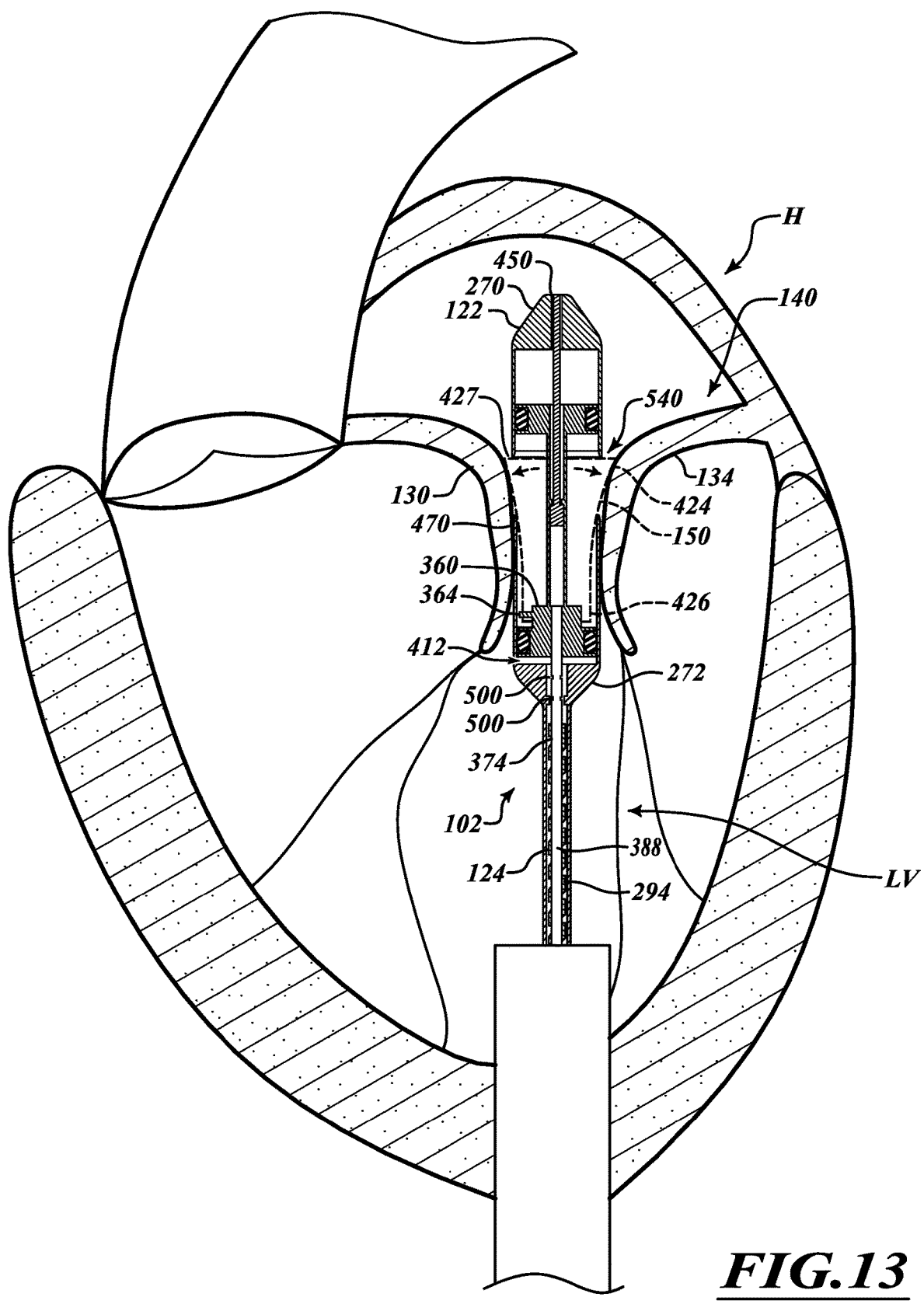

FIG. 13 shows the distal sheath 270 after it has been moved to an open or deployed position. The unsheathed atrial end 424 of the prosthetic device 150 has moved (as indicated by arrows) through an opening 540 to allow the atrial end 424 to radially expand. An atrial rim 427 of the atrial end 424 can expand to its fully deployed configuration (shown) to engage native heart tissue around the circumference (e.g., most of or the entire circumference) of the mitral valve 140. In some procedures, the atrial rim 427 can contact the native annulus AN, tissue proximate to the native annulus AN either in the atrium or ventricle, the native valve leaflets, and/or other tissue suitable for contacting the prosthetic device 150. For example, the atrial rim 427 can contact the leaflet/annulus connecting tissue and tissue of the leaflets proximate to the native annulus AN. In self-expanding embodiments, the radially unrestrained atrial end 424 expands upon unsheathing. In other embodiments, expanders can be used to expand the unsheathed atrial end 424. For example, an expander in the form of a balloon can be positioned within the prosthetic device 150 and can be inflated to deploy the atrial end 424.

The delivery capsule 122 is expected to substantially prevent axial movement of the prosthetic device 150. For example, the holder 360 can prevent translation of the sheathed portion of the prosthetic device 150 while the atrial end 424 expands. In some embodiments, the expanded portion of the prosthetic device 150 may pull on the sheathed portion of the prosthetic device 150. The prosthetic device 150 would deploy in an uncontrolled manner but for the holder 360 restraining axial translation of the prosthetic device 150. In some embodiments, the holder 360 can hold the proximal sheath 272 substantially stationary relative to the mitral valve 140. As shown in FIGS. 12 and 13, the axial position of the prosthetic device 150 can be maintained throughout expansion of the atrial end 424.

Additionally, the force exerted by the biasing device 294 can be sufficient to prevent uncontrolled movement of the proximal sheath 272 in the proximal direction. For example, the partially expanded prosthetic device 150 of FIG. 13 may contact and apply a force component (e.g., an axially directed force component, a proximally-directed force component, etc.) to the distal end 470 of the proximal sheath 272. The compressed biasing device 294 can urge the proximal sheath 272 in the distal direction to counteract the force component. The biasing device 294 can thus inhibit, limit, or substantially prevent movement of the proximal sheath 272 in the proximal direction caused by the prosthetic device 150. The characteristics (e.g., spring constant, applied force versus deflection curve, etc.) of the biasing device 294 can be selected based on the forces that will be produced by the prosthetic device 150. Linear springs can be used with, for example, prosthetic devices that produce substantially constant deployment forces (e.g., substantially constant proximally-directed force component). Non-linear springs can be used with, for example, prosthetic devices that produce varying deployment forces.

In some embodiments, the biasing device 294 can provide a variable force. The variable force can be generally maximum when the forces from the prosthetic device 150 pushing on the delivery capsule 122 are highest and resistance between the delivery capsule and the prosthetic device is lowest. As the prosthetic device 150 is unsheathed from the delivery capsule 122, a greater and greater portion of the prosthetic device is exposed outside the delivery capsule and the forces exerted by the exposed portion of the prosthetic device urging the delivery capsule to the open configuration are increasing. At the same time, the surface area of the prosthetic device 150 remaining in the delivery capsule 122 is decreasing, thus reducing the frictional resistance between the prosthetic device 150 and the delivery capsule 122. Thus, in some embodiments, the force exerted by the biasing device 294 increases as the prosthetic device 150 is unsheathed. In some embodiments, biasing device 294 can be a spring which applies a force that increases with spring displacement. In some embodiments, the biasing device 294 can include plurality of springs. For example, one spring can have a low spring constant to counteract low forces applied by the prosthetic device 150 to the delivery capsule 122. Another spring can have a relative large spring constant to counteract high forces applied by the prosthetic device 150 to the delivery capsule 122. In some embodiments, the biasing device 294 can be offset such that the distal sheath 270 and/or proximal sheath 272 can be moved a predetermined distance before the biasing device begins to apply a force. One of the distal sheath 270 and the proximal sheath 272 can be moved a short distance (e.g., 1 mm-5 mm) before a first spring (e.g., a spring with a low spring constant) begins to deform. A second spring (e.g., a spring with a high spring constant) of the biasing device 294 can begin to deform as the delivery capsule 122 approaches the deployed configuration. The number and properties of the springs can be selected to achieve the desired deployment of the prosthetic device 150.

FIG. 13 shows the proximal sheath 272 in a closed position. During operation, fluid can flow along the lumen 388, through the ports 500, and into the chamber 412. The fluid pressure in the chamber 412 can increase until the fluid pressure causes proximal movement of the proximal sheath 272. When the pressure in the fluid chamber 412 overcomes the biasing force of the biasing device 294, the proximal sheath 272 can move proximally, thereby compressing the biasing device 294. In some embodiments, the distance of travel of the proximal sheath 272 can be generally proportional to the fluid pressure in the chamber 412 such that the fluid pressure in the chamber 412 can be increased to controllably move the proximal sheath 272.

In some embodiments, the prosthetic device 150 (in an expanded configuration) comprises a generally frusto-conical, bell, or other flared shape. In particular, the atrial end 424 can have a diameter that is greater than the diameter of the downstream or ventricular end 426 in an unrestrained deployed configuration. For example, the atrial end 424 may produce a first force generally in the proximal direction when the atrial end 424 exits the opening 540. When the ventricular end 426 exits the proximal sheath 272, it may produce a second force generally in the proximal direction. In this embodiment, the prosthetic device 150 interacts with the distal and proximal sheaths such that the first force is greater than the second force. In other embodiments, the prosthetic device 150 can have generally tubular shape and a uniform diameter along its length when in its delivery configuration and when in its expanded configuration. In still other embodiments, the prosthetic device 150 may have other arrangements.

Figure 14:
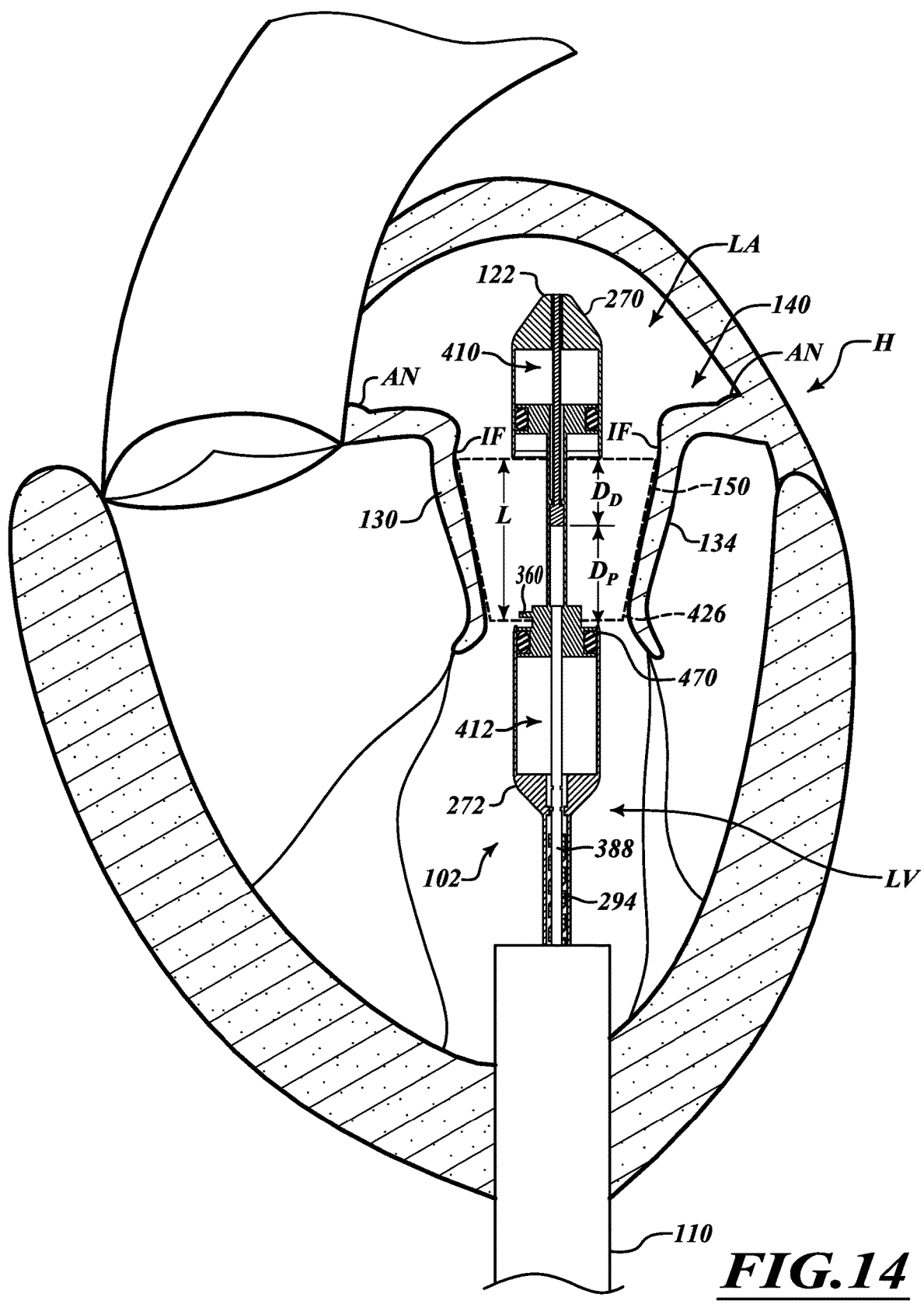

After the distal end 470 of the proximal sheath 272 moves proximally past the ventricular end 426 of the prosthetic device 150, the ventricular end 426 can move radially outward from the posts 364 to contact the posterior and anterior leaflets 130, 134. FIG. 14, for example, shows the prosthetic device 150 after its entire axial length has been unsheathed. The prosthetic device 150 can include, without limitation, one or more anchoring members that engage the native valve 140 so as to, for example, resist systolic forces, prevent upstream migration of the prosthetic device 150, etc. In some embodiments, the prosthetic device is configured to engage subannular tissue of the native valve 140. Referring to FIG. 1A-1 and FIG. 14 together, "subannular," as used herein, refers to a portion of the mitral valve 140 that lies on or downstream DN (FIG. 1A-1) of the plane PO of the native orifice. The plane PO (FIG. 1A-1) of the native valve orifice is a plane generally perpendicular to the direction of blood flow through the valve and which contains either or both the major axis MVA1 or the minor axis MVA2 (FIG. 1E).

The prosthetic device 150 can include upstream anchors configured to engage the inward-facing surfaces IF of the native leaflets 130, 134, which may be pushed outwardly and folded under the native annulus AN. The leaflets 130, 134, for example, can engage a ventricular side of the annulus AN and may be prevented from being pushed further in the upstream direction, thus maintaining the anchoring member below the plane of the native valve annulus. The tissue engaging elements can penetrate the tissue of the leaflets 130, 134, the annulus AN, and/or other tissue to stabilize and firmly anchor the prosthetic device 150. In some embodiments, some portions of the anchoring members may extend above the annulus AN, with at least some portions of the anchoring member engaging tissue in a subannular location to prevent migration of the prosthetic device 150 toward the left atrium LA. The prosthetic device 150 is configured to conform to the irregularly-shaped mitral annulus AN, effectively sealing the prosthetic device 150 against the native annulus AN to anchor the prosthetic device 150 and to prevent paravalvular leaks. The prosthetic device 150, for example, can be a prosthetic device (e.g., a prosthetic heart valve device) such as one or more of the prosthetic devices disclosed in (1) International PCT Patent Application No. PCT/US2012/043636, entitled "PROSTHETIC HEART VALVE DEVICES AND ASSOCIATED SYSTEMS AND METHODS," filed on Jun. 21, 2012; (2) U.S. Provisional Patent Application No. 61/549,037, entitled "SYSTEM FOR MITRAL VALVE REPLACEMENT," filed on Oct. 19, 2011; (3) U.S. Provisional Patent Application No. 61/605,699, entitled "SYSTEM FOR MITRAL VALVE REPLACEMENT," filed on Mar. 1, 2012; and (4) International PCT Patent Application No. PCT/US2012/061215, entitled "DEVICES, SYSTEMS AND METHODS FOR HEART VALVE REPLACEMENT," filed on Oct. 19, 2012. Each of these references is incorporated by reference in its entirety. For example, the delivery catheters disclosed herein can include a sheath containing a prosthetic device. The sheath can be a split-sheath including, without limitation, a distal nose cone and a proximal capsule, as disclosed in U.S. Provisional Patent Application No. 61/605,699, entitled "SYSTEM FOR MITRAL VALVE REPLACEMENT," filed on Mar. 1, 2012. The delivery catheter can also include other features (e.g., sheaths, tethers, pistons, stops, cables, etc.) disclosed in U.S. Provisional Patent Application No. 61/605,699, entitled "SYSTEM FOR MITRAL VALVE REPLACEMENT," filed on Mar. 1, 2012 or other references incorporated by reference in their entirety. It will also be appreciated, however, that other types of prosthetic devices can also be deployed by the delivery capsule.

In the illustrated embodiment, a distance of travel DD of the distal sheath 270 can be substantially less than an axial length L of the prosthetic device 150. For example, the distance of travel DD can be less than about 70%, 60%, or 50% of the length L of the prosthetic device 150. In other embodiments, however, the distance of travel DD may have different values relative to the length L of the prosthetic device 150. In some embodiments, each sheath 270, 272 can contain about half of the prosthetic device 150. Distances of travel DD, DP of the sheaths 270, 272 can be generally equal, such that the sheaths 270, 272 can move into the left atrium LA and left ventricle LV, respectively, without contacting the wall of the heart. In particular embodiments, the distal sheath 270 can unsheathe about 8 mm to about 16 mm of the prosthetic device 150, and the proximal sheath 272 can unsheathe about 8 mm to about 16 mm of the prosthetic device 150. The length L, for example, can be about 16 mm to about 32 mm. In other embodiments, however, the sheaths 270, 272 may be configured to unsheathe more or less of the prosthetic device 150 and/or the length L can vary.

With continued reference to FIG. 14, the delivery capsule 122 can be returned to the containment configuration. In particular, fluid can flow out of the chamber 412 and proximally through the lumen 388, and the biasing device 294 can urge the proximal sheath 272 back to the closed position. Additionally, fluid can flow out of the chamber 410 to move the distal sheath 270 back to the closed position. In some embodiments, a vacuum is drawn to draw fluid from one or both chambers 410, 412. Additionally or alternatively, one or more biasing devices can move the distal sheath 270.

After the delivery capsule 122 is moved to the containment configuration, it can be pulled proximally through the deployed prosthetic device 150 and into the left ventricle LV. The delivery capsule 122 can be pulled into the guide catheter 110 and removed from the subject. Other techniques can be used to remove the catheter 102 from the heart.

The method discussed above in connection with FIGS. 11-14 can be modified to deliver the prosthetic device 150 via trans-septal or retrograde approaches. For example, the length of the catheter body 124, dimensions of the delivery capsule 122, and steerability of the catheter 102 can be selected based on a selected delivery path (e.g., via the aortic valve, via the venous vasculature, etc.). Additionally, various types of visualization techniques can be used with the method discussed in connection with FIGS. 11-14. For example, visualization can be used to help deliver, position, operate, and/or remove the catheter 102. For example, fluoroscopy, computer tomography (CT), magnetic resonance imaging (MRI), ultrasound, or other imaging techniques can help evaluate an access path, delivery path, treatment site, and position of the catheter 102 and/or prosthetic device 150 before, during, and/or after delivery of the prosthetic device 150.

FIGS. 15-17 are a series of views of a method of deploying a prosthetic device from a delivery capsule 600 in accordance with various embodiments of the present technology. The delivery capsule 600 can include features and functionality generally similar to the features and functionality of delivery capsule 122 discussed in connection with FIGS. 2A-14, except as detailed below.

FIG. 15, for example, is a partially schematic cross-sectional view illustrating the delivery capsule 600 including a mechanically actuatable distal sheath 604, a hydraulically actuatable proximal sheath 606, and a piston device 610. A prosthetic device 620 (shown in broken lines) is positioned within a containment chamber 622 that can be isolated from a fluid chamber 684.

The distal sheath 604 can include a main sheath body 640 and a rod 642 (e.g., a solid shaft, a hollow shaft, etc.). The main sheath body 640 includes a tubular portion 643 and a closed distal end 645. The rod 642 can be fixedly coupled to the closed distal end 645 and extends through a lumen 646 of an elongated catheter body 648 ("catheter body 648"). The rod 642 can be moved distally to move the distal sheath 604 from a closed position (FIG. 15) to an open position (FIG. 16). In some embodiments, the rod 642 can be manually moved. In other embodiments, however, a drive mechanism can move the rod 642. The drive mechanism can include, without limitation, a screw drive mechanism, a pneumatic drive mechanism, or other type of mechanism capable of providing linear motion.

FIG. 16 shows a distal end 650 of the prosthetic device 620 being unsheathed. For example, the distal end 650 can expand outwardly, as indicated by arrows 670, 672, while the piston device 610 can restrain a proximal end 698 of the prosthetic device 620. After the unsheathed portion of the prosthetic device 620 has expanded, fluid can be delivered along the lumen 646 and into the chamber 684 to hydraulically move the proximal sheath 606 from a closed position (FIG. 16) to an open position (FIG. 17). In some embodiments, the outer diameter of the rod 642 can be slightly smaller than the diameter of the lumen 646 to allow fluid to flow distally along the elongated catheter body 648. Additionally or alternatively, the rod 642 can have one or more flow features, such as channels, recesses, lumens, etc. A biasing device 690 can be compressed between a stop 692 and the catheter body 648. After an open end 699 of the proximal sheath 606 moves proximally past the proximal end 698 of the prosthetic device 620, the proximal end 698 is allowed to move outwardly to a deployed configuration.

Figure 18:
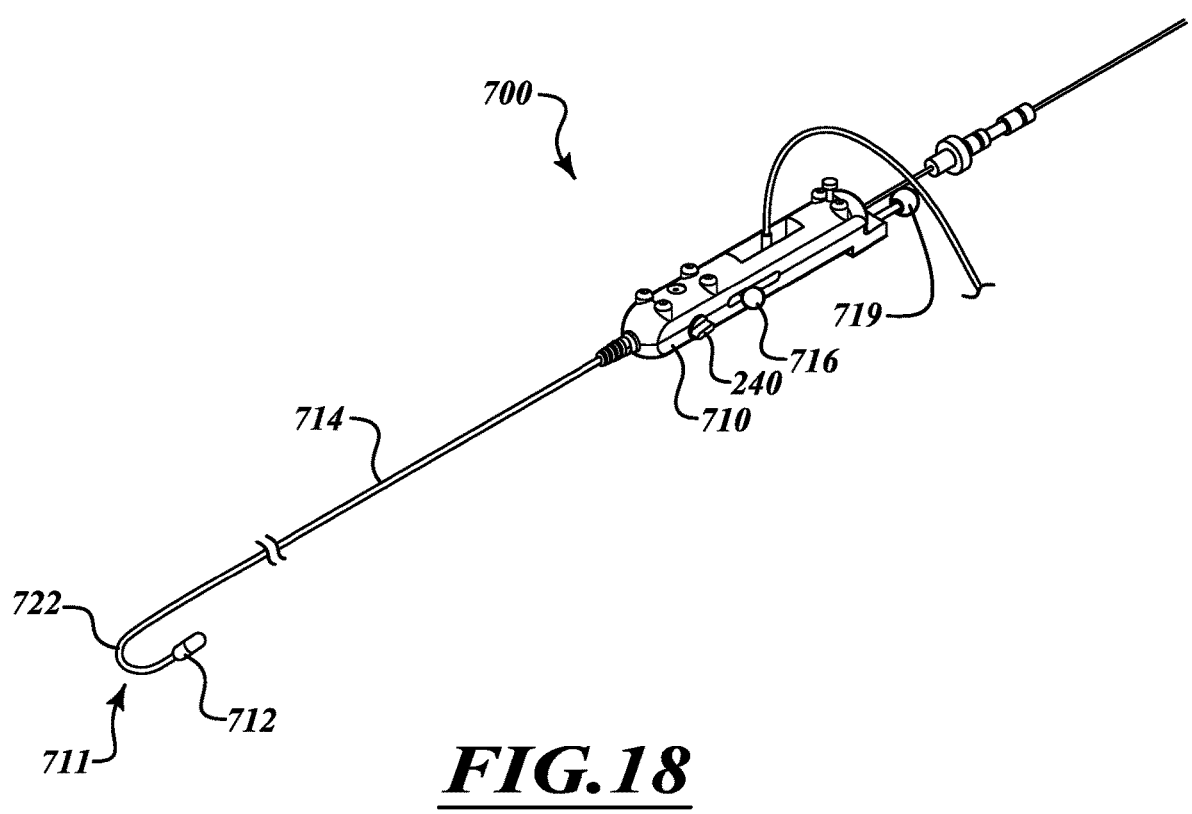
FIG. 18 is an isometric view of a catheter for delivering a prosthetic device in accordance with various embodiments of the present technology.

FIG. 18 is an isometric view of a catheter 700 for delivering a prosthetic device configured in accordance with another embodiment of the present technology. The catheter 700 can include, for example, a control unit 710, a delivery capsule 712, and an elongated catheter body 714 ("catheter body 714"). The control unit 710 can include an actuation mechanism 716 and an articulation mechanism 719. The actuation mechanism 716 can be used to operate the delivery capsule 712. The articulation mechanism 719 can be used to adjust the configuration of an articulatable region 722 of the catheter body 714.

Figure 19:
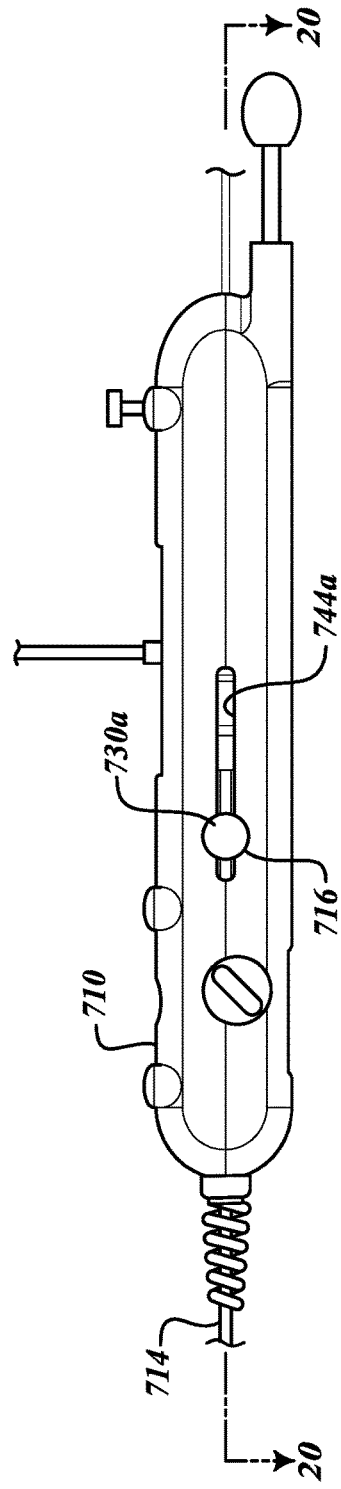
FIG. 19 is a side view of a control unit of the catheter of FIG. 18 in accordance with various embodiments of the present technology.
Figure 20:
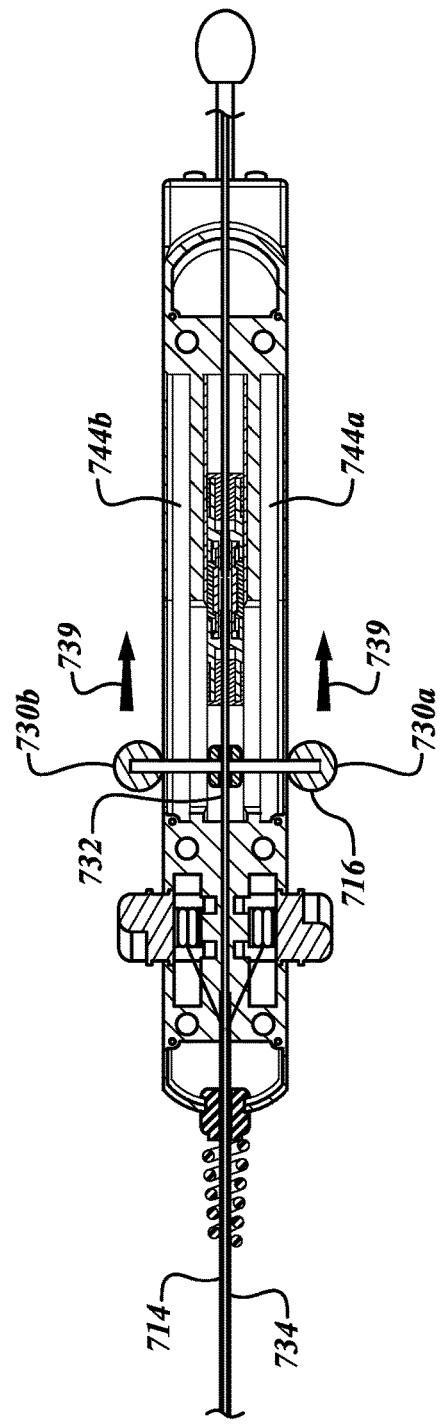
FIG. 20 is a cross-sectional view of the control unit taken along line 20-20 of FIG. 19.

FIG. 19 is a side view of the control unit 710, and FIG. 20 is a cross-sectional view of the control unit 710 taken along line 20-20 of FIG. 19. Referring to FIGS. 19 and 20 together, the actuation mechanism 716 can include slider elements 730a, 730b (collectively "730") coupled to a tubular member 732 (FIG. 20). The tubular member 732 can extend through an outer tubular member 734 of the elongated catheter body 714 and can be coupled to a sheath of the delivery capsule 712. The slider elements 730 can be moved proximally (as indicated by arrows 739 of FIG. 20) along elongated slots 744a, 744b to move the tubular member 732 in the proximal direction. Other types of actuation mechanisms can be used and can include, without limitation, one or more knobs, slots, pull wires, or the like.

Figure 21:
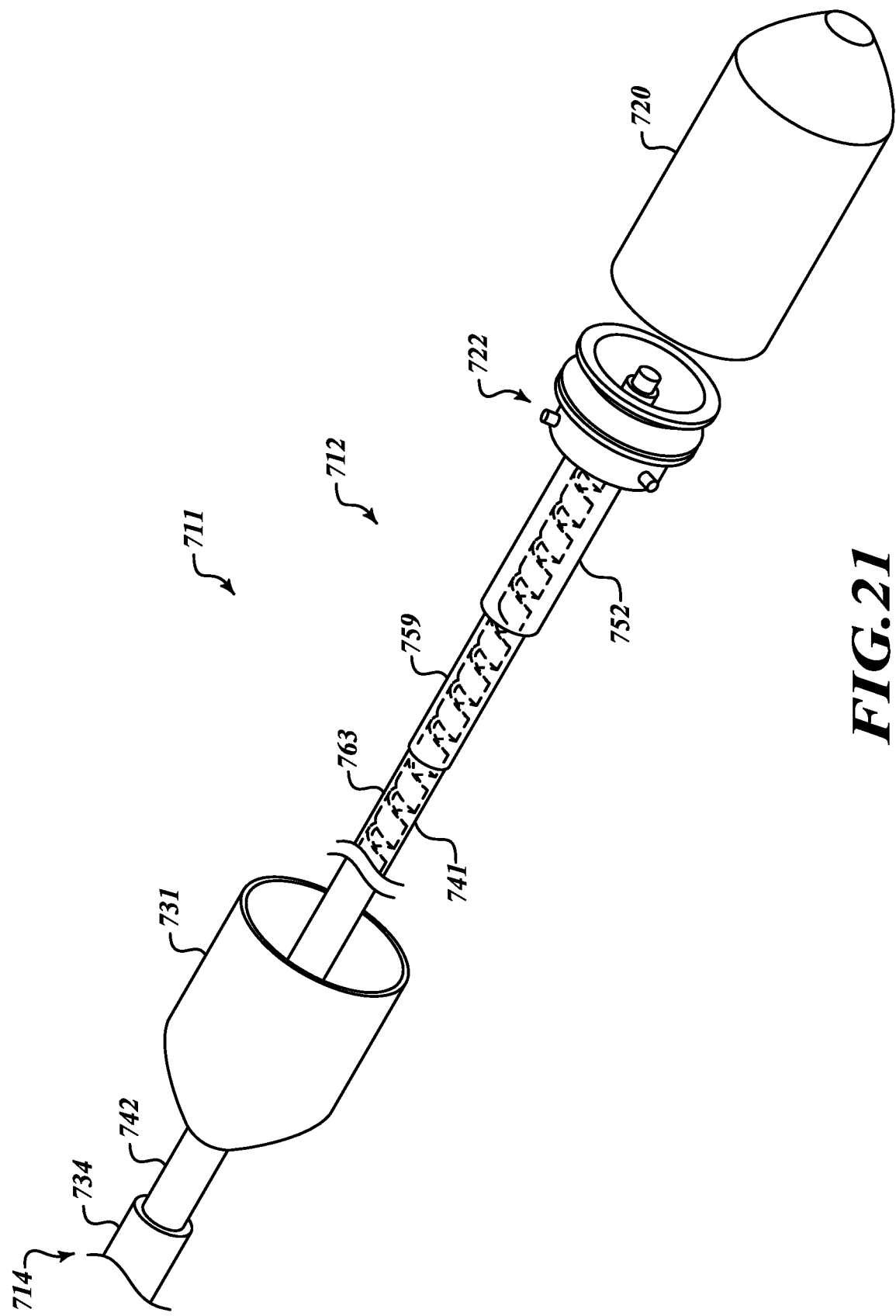
FIG. 21 is an exploded isometric view of a distal portion of the catheter of FIG. 18.

FIG. 21 is an exploded isometric view of a distal portion 711 of the catheter 700 of FIG. 18. The delivery capsule 712, for example, can include a distal sheath 720, a piston device 722, and a proximal sheath 731. The catheter body 714 can include an inner assembly 741 coupled to the piston device 722, an intermediate member 742 (e.g., a hollow shaft) coupled to the proximal sheath 731, and the outer member 734. The inner assembly 741 can extend through at least a portion of the intermediate member 742. In other embodiments, however, the delivery capsule 712 may include different features and/or have a different arrangement.

Figure 22:
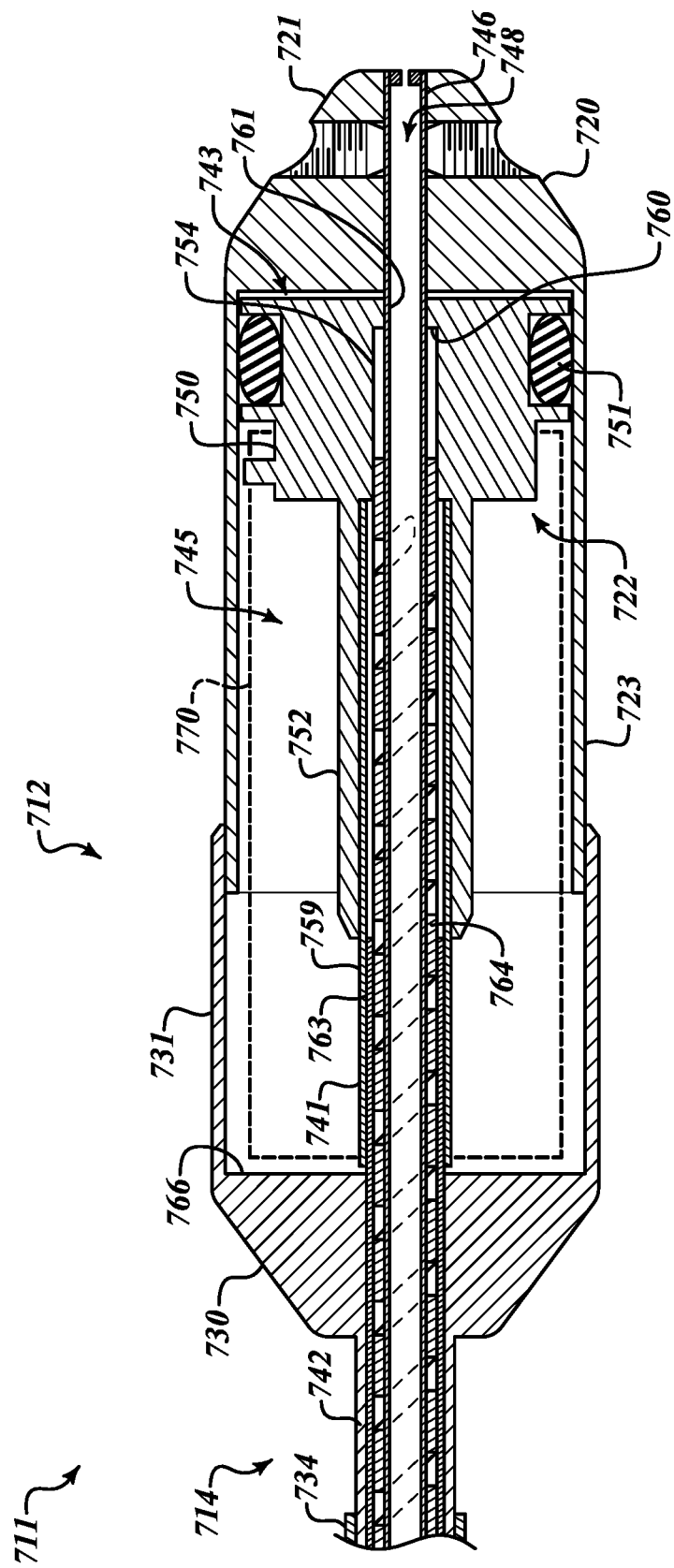
FIG. 22 is a cross-sectional view of the distal portion of the catheter of FIG. 18.

FIG. 22 is a cross-sectional view of the distal portion 711 of the delivery capsule 712 of FIG. 21 in a containment configuration. As best seen in FIG. 22, the distal sheath 720 and the piston device 722 can cooperate to define a fluid chamber 743. The fluid chamber 743 can be fluidically sealed from a containment chamber 745. The distal sheath 720 can include a rod 764 defining a guidewire lumen 748. A biasing device 746 can be coupled to the rod 764 such that displacement of the distal sheath 720 in the distal direction causes compression of the biasing device 746.

The distal sheath 720 can include a distal end portion 721, a containment portion 723, and the rod 764. In multi-piece embodiments, the rod 764 can be a tubular member fixedly coupled to the distal sheath 720 by one or more fasteners, adhesive, welding, or the like. In one-piece embodiments, the distal sheath 720 can be formed by a molding process (e.g., injection molding process, compression molding process, etc.), machining process, or another suitable manufacturing technique.

The piston device 722 can include a head 750, a sealing member 751, and a tubular body 752. The head 750 includes a flange 760 defining an opening 761. The body 752 couples the head 750 to the inner assembly 741, which in turn is coupled to the intermediate member 742. The rod 764 of the distal sheath 720 extends thought the opening 761 and a receiving slot 754 in the head 750. A biasing device 746 (e.g., a spring) surrounds the rod 764. A mounting region 749 (FIG. 23) of the biasing device 746 can be fixedly coupled to the rod 764. In other embodiments, the biasing device 746 may have a different arrangement and/or include different features.

FIGS. 23-25 are a series of views of a method of deploying a prosthetic device 770. FIG. 23, for example, is a cross-sectional view of the delivery capsule 712 with the proximal sheath 731 in an open position. FIG. 24 is a cross-sectional view of the delivery capsule 712 with the distal sheath 720 in an intermediate position, and FIG. 25 is a cross-sectional view of the delivery capsule 712 in a deployment configuration. Generally, the proximal sheath 731 can be mechanically driven to unsheathe a proximal end 772 of a prosthetic device 770, and the distal sheath 720 can be hydraulically driven to unsheathe a distal end 774 of the prosthetic device 770. Various details of a method of deploying the prosthetic device 770 are discussed below.

As described above with reference to FIG. 22, the piston device 722 can hold the prosthetic device 770, and the slider element 730a (FIG. 20) can be moved to mechanically drive the proximal sheath 731 from a closed position (FIG. 22) to an open position (FIG. 23). More specifically, FIG. 23 shows the unsheathed proximal end 772 of the prosthetic device 770 ready to expand outwardly through a gap 781, as indicated by arrows 782. The distal end 774 of the prosthetic device 770 can be unsheathed by delivering fluid distally along a lumen 784 and into the fluid chamber 743 via ports 790. In some embodiments, a guidewire may be positioned in the lumen 748. The fluid can flow distally along the lumen 748 in the space between the guidewire (not shown) and the rod 764. In other embodiments, the guidewire can be removed from the lumen 748 prior to delivering the fluid.

FIG. 24 shows an end 796 of the biasing device 746 contacting the flange 760. The compressed biasing device 746 can exert a force in the proximal direction to prevent uncontrolled movement of the distal sheath 720 and/or prosthetic device 770. The fluid pressure in the chamber 743 can be increased to controllably move the distal sheath 720 in the distal direction. After an open end 800 of the distal sheath 720 moves distally past the distal end 774 of the prosthetic device 770, the distal end 774 can be allowed to expand outwardly. Referring to FIG. 25, the proximal sheath 731 can be moved from the open position (FIG. 25) back to the closed position (FIG. 22) using the actuation mechanism 716 (FIG. 18). The biasing device 746 can urge the distal sheath 720 from the open position (FIG. 25) back to the closed position (FIG. 22).

Figure 26:
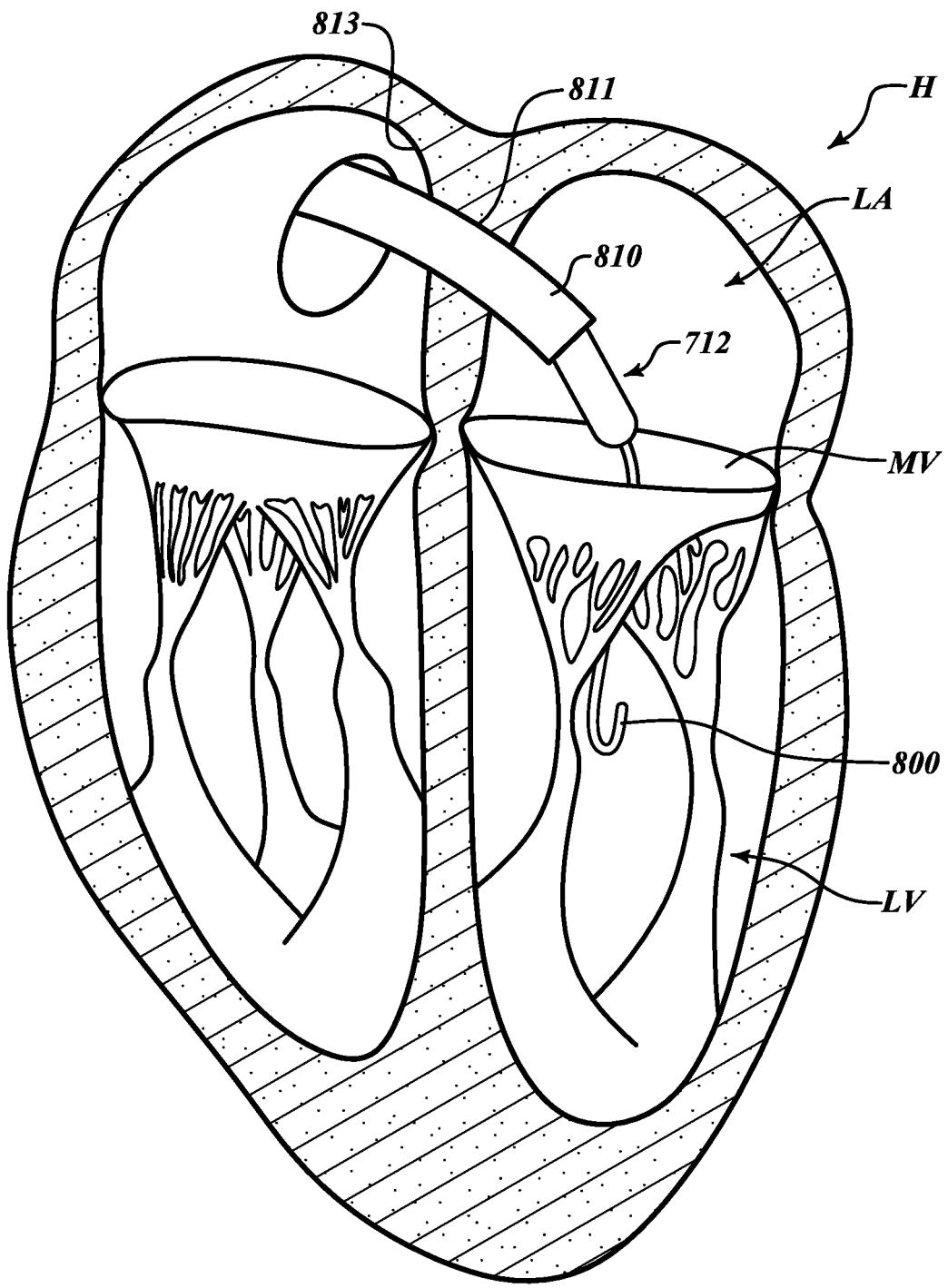
FIGS. 26-29 are a series of views of a method of deploying a prosthetic device within a native mitral valve in accordance with various embodiments of the present technology.
Figure 27:
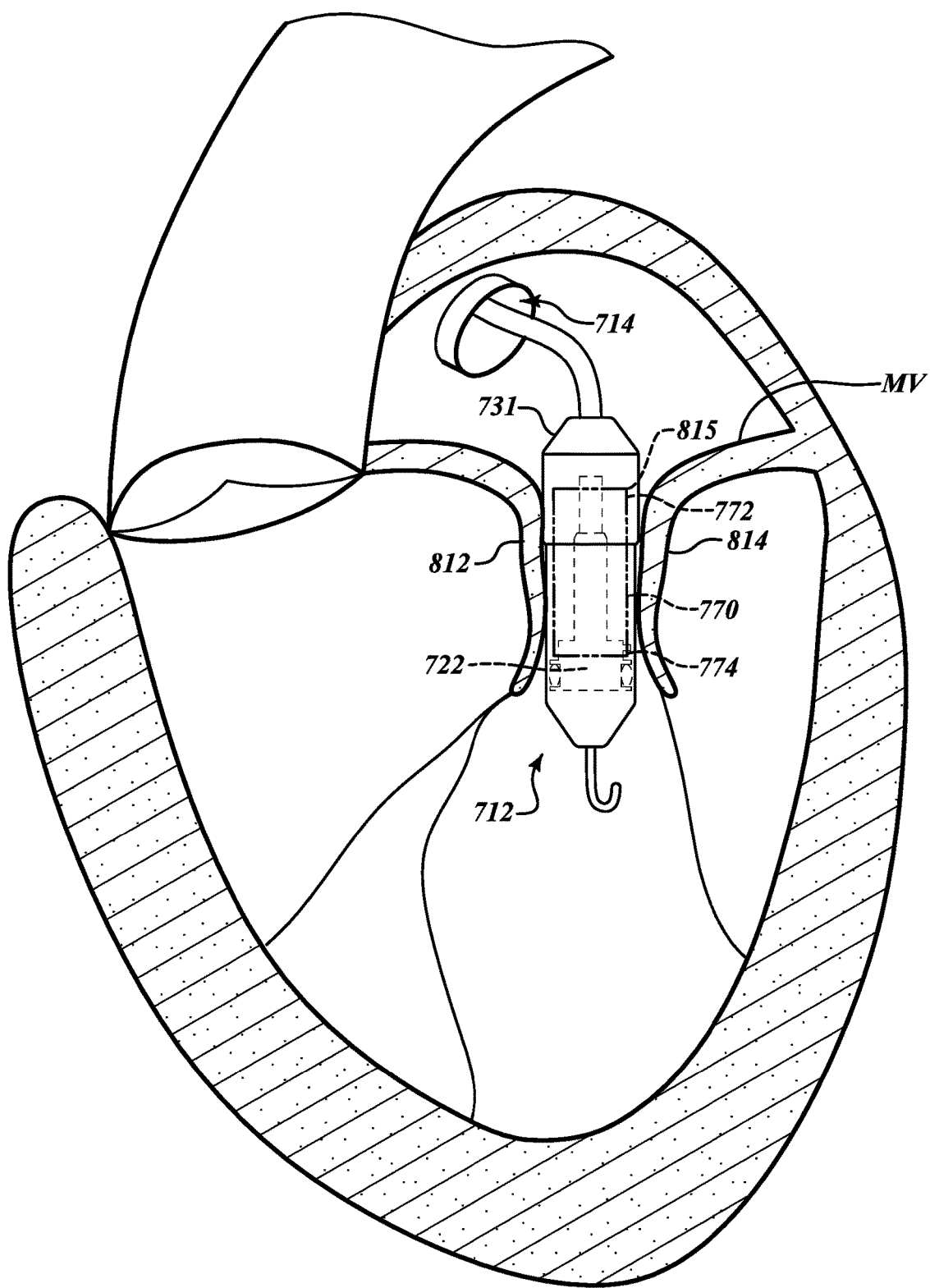
Figure 28:
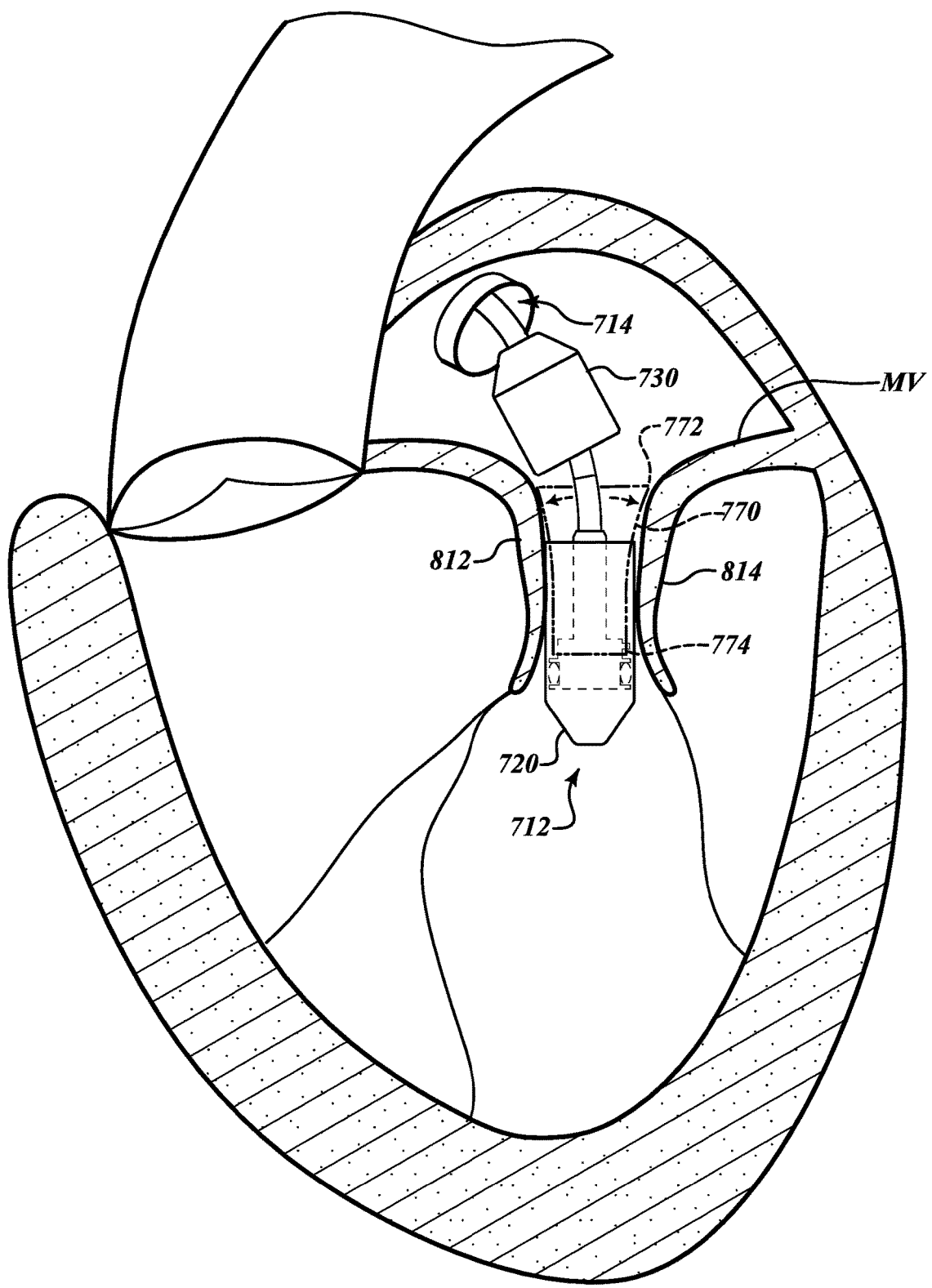
Figure 29:
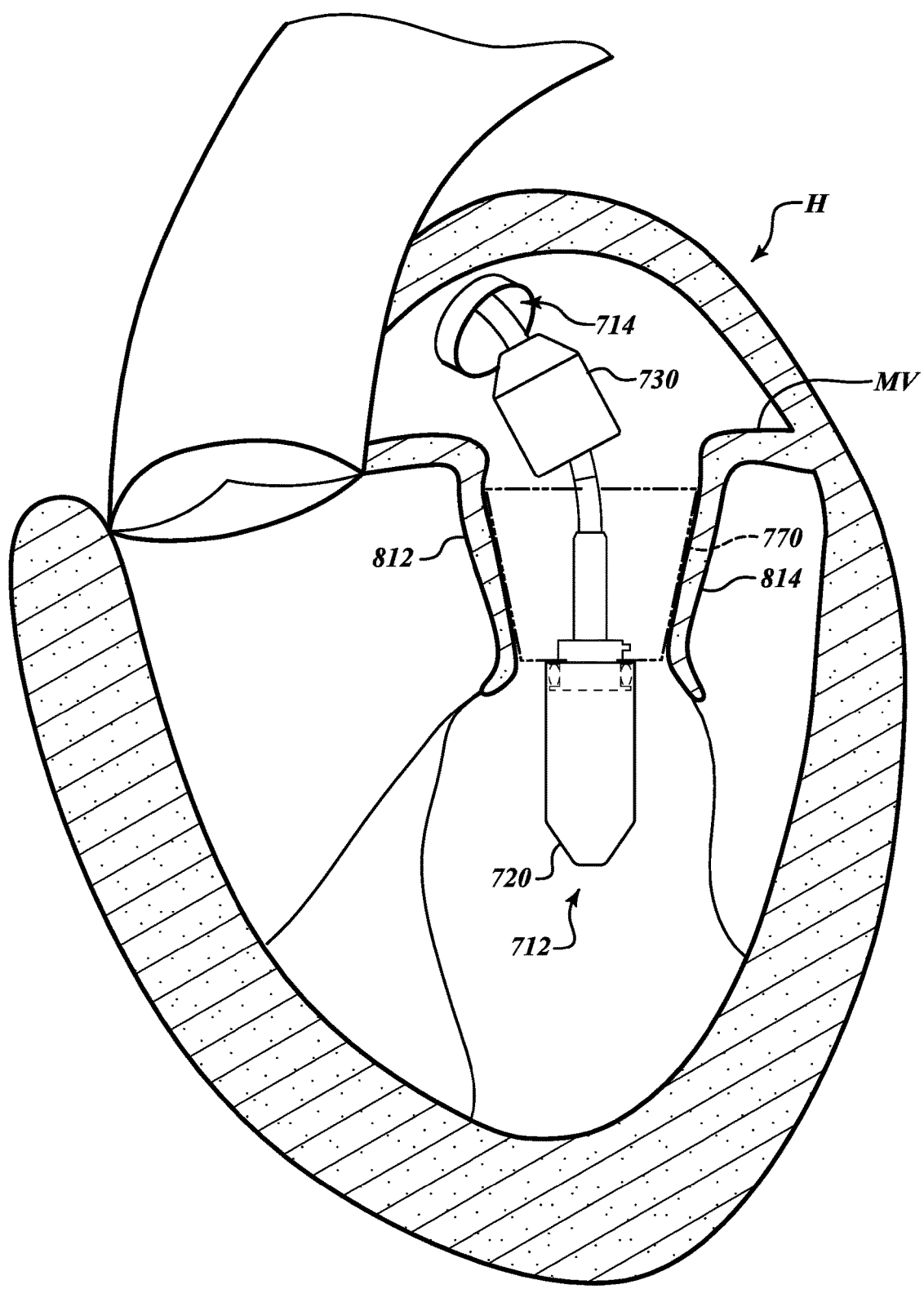

FIGS. 26-29 are a series of views of a method of deploying the prosthetic device 770 within the heart H using a trans-septal approach. FIG. 26, for example, shows a guidewire 800 positioned in the mitral valve MV, and FIG. 27 shows the delivery capsule 712 positioned in the mitral valve MV. FIG. 28 shows the delivery capsule 712 in a partially open configuration, and FIG. 29 shows the delivery capsule 712 in a deployment configuration and the deployed prosthetic device 770.

Referring first to FIG. 26, the guidewire 800 is positioned to extend through the mitral valve MV and into the left ventricle LV. A guide catheter 810 can be positioned through a puncture or opening 811 in a septum 813, and the delivery capsule 712 can be delivered out of the guide catheter 810 and advanced along the guidewire 800.

FIG. 27 shows the delivery capsule 712 positioned between the posterior and anterior leaflets 812, 814. An upstream or atrial rim 815 of the prosthetic device 770 can be positioned relative to the mitral valve MV. The proximal sheath 731 can be moved proximally to unsheathe the upstream or atrial end 772 of the prosthetic device 770 while the downstream or ventricular end 774 of the prosthetic device 770 is retained by the piston device 722.

Referring next to FIG. 28, the unsheathed atrial end 772 is expanded outward to contact the mitral valve MV. Until the atrial end 772 engages the native tissue, the ventricular end 774 of prosthetic device 770 is retained by piston device 722 within distal sheath 720 to prevent axial movement of prosthetic device 770 relative to catheter body 714. After the deployed portion of the prosthetic device 770 is seated in the mitral valve MV, fluid is delivered through the elongated catheter body 714 to hydraulically move the distal sheath 720 from the closed position (FIG. 28) to the open position (FIG. 29). More specifically, FIG. 29 shows the prosthetic device 770 in a fully deployed configuration. The delivery capsule 712 can then be returned to the closed configuration, pulled through the left atrium, and removed from the heart H.

FIG. 30 is an isometric view of a distal portion of a catheter configured in accordance with yet another embodiment of the present technology. In this embodiment, a distal portion 837 of the catheter can include a delivery capsule 842 and an elongated catheter body 844 ("catheter body 844"). The delivery capsule 842 can include a hydraulically actuatable sheath 850 and a cover assembly 852. In this embodiment, sheath 850 is configured to contain substantially the entire length of prosthetic device 880, while cover assembly 852 serves to cover the open proximal end 871 of sheath 850.

Figure 32:
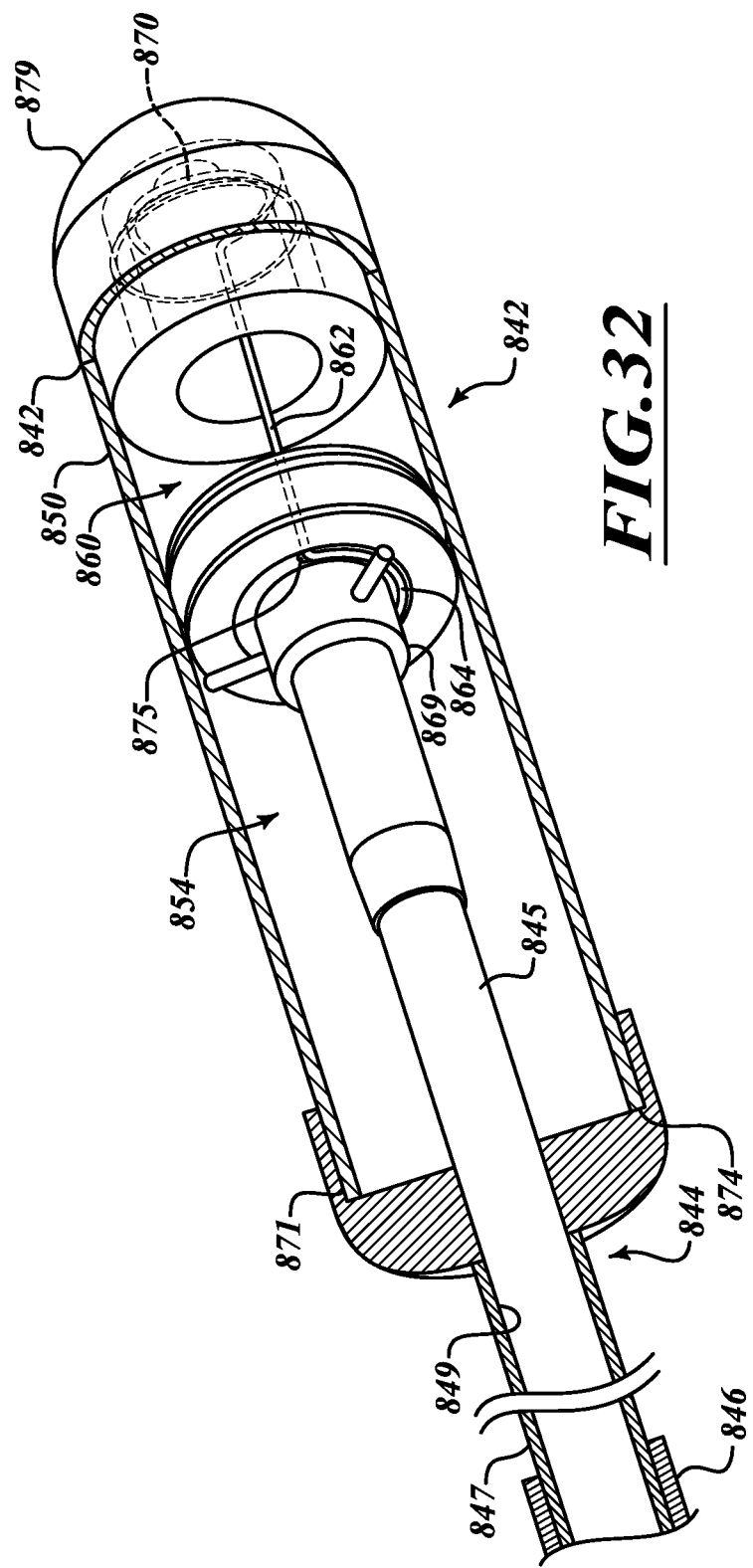

FIGS. 31 and 32 are isometric cutaway views of the distal portion 837 of FIG. 30. Referring to FIGS. 31 and 32 together, the catheter body 844 can include an inner shaft 845 and an outer member or shaft 846. The inner shaft 845, for example, extends through a lumen 849 of the cover assembly 852 and is connected to a piston device 854. The outer member 846 can be a tubular member that surrounds a guide portion 847 of the cover assembly 852. A control unit can be coupled to the guide portion 847.

The delivery capsule 842 can further include a sheath restraining mechanism 860 ("restraining mechanism 860") with a tether 862 configured to provide a resisting force that opposes a direction of movement of the sheath 850 relative to the piston device 854. In some embodiments, for example, the tether 862 provides a resistive force to resist distal movement of the sheath 850 relative to the piston device 854. The resistive force can be overcome to move the sheath 850 and to compensate for forces, if any, produced by the prosthetic device. In some embodiments, for example, the tether 862 can minimize, limit, or substantially eliminate the effect of forces, if any, produced by the prosthetic device to prevent or limit uncontrolled movement (e.g., axial jumping and self-ejection) of the prosthetic device and/or uncontrolled movement of the sheath 850.

FIG. 32 shows the tether 862 with a proximal portion 864 at least partially wrapped around a hub 869 of a head 866 of the piston device 854. A distal portion 870 (FIG. 31) of the tether 862 can be fixedly coupled to the sheath 850. For example, one or more fasteners (e.g., set screws, pins, etc.) or other features (e.g., a clamp, welds, etc.) can fixedly couple the distal portion 870 to the sheath 850. In one embodiment, the tether 862 is locked in place by one or more screws (e.g., flat-bottom set screws). In other embodiments, however, the tether 862 may be secured in place using other suitable techniques. A torque (e.g., a torque of about 11 oz-in) can be applied to the screws, which in turn frictionally hold the tether 862. The distal portion 870 of the tether 862 may then cut to a desired minimum length and housed in a cap 879 (e.g., a hollow cap) of the sheath 850. Additionally or alternatively, the distal portion 870 can wrap about an internal component (e.g., a spool, a pin, etc.) of the sheath 850. The internal component can be removed to adjust the length of the tether 862 connecting the piston device 854 to the sheath 850. In some embodiments, the tether 862 can be a wire made of nitinol, spring steel, plastic, or combinations thereof. In one particular embodiment, the tether 862 is a metal wire (e.g., a wire comprising nitinol, spring steel, etc.) with a diameter of about 0.012 inch (0.35 mm). Other diameters can be selected based on the desired forces for deploying the prosthetic device. The illustrated restraining mechanism 860 has the single tether 862. In other embodiments, however, any number of tethers can be used. Additionally, the restraining mechanism 860 can include, without limitation, one or more biasing devices, such as springs. The biasing device(s) can urge the delivery capsule 842 towards the containment configuration.

FIGS. 33-35 illustrate a method of deploying a prosthetic device 880. More specifically, FIG. 33 shows the delivery capsule 842 in the containment configuration, FIG. 34 shows the delivery capsule 842 in a partially open configuration, and FIG. 35 shows the delivery capsule 842 in a deployment configuration. Referring to FIG. 33, the open proximal end 871 of the sheath 850 is received in an open distal end 895 of the cover assembly 852. Fluid can flow along a lumen 881 and into a fluid chamber 892. A sufficient volume of fluid can be delivered into the fluid chamber 892 to push the sheath 850. When the hydraulic force (e.g., the force component in the distal direction) overcomes the resistive force provided by the restraining mechanism 860, the sheath 850 moves in the distal direction relative to the piston device 854. In some embodiments, the tether 862 can slip along a screw (e.g., a set screw) to allow distal movement of the sheath 850. For example, the tether 862 can slide relative to a torque-loaded set screw applying pressure to the tether 862 to allow distal movement of the sheath 850 and unsheathing of the prosthetic device in a controlled fashion. In some embodiments, the tether 862 can deform (e.g., plastically deform, elastically deform, etc.). In some embodiments, for example, the tether 862 experiences primarily elastic deformation. The hydraulic forces in the fluid chamber 892 can be decreased to allow the tether 862 to return to its initial state to pull the sheath 850 back to the closed position (FIG. 33). In other embodiments, the tether 862 can experience primarily permanent deformation. FIG. 34 shows an unsheathed portion 892 of the prosthetic device 880 expanding outwardly through an opening 890. The volume of fluid in the fluid chamber 892 can be increased to move the sheath 850 from an intermediate position (FIG. 34) to an open position (FIG. 35).

FIG. 36 is a cross-sectional view of a distal portion of a catheter configured in accordance with various embodiments of the present technology. A distal portion 904 can include a delivery capsule 910 and an elongated catheter body 940 ("catheter body 940"). The delivery capsule 910, for example, includes a sheath 912, a piston device 914, and a positioner in the form of a ratchet element 924. The sheath 912 includes a hollow inner rod 944 that extends through the ratchet element 924 such that the ratchet element 924 facilitates controlled delivery of a prosthetic device throughout a substantial portion of the piston stroke (e.g., throughout most of the piston stroke). A biasing device 930 can react against a self-ejection load of a prosthetic device 962 (if any) for controlled delivery of the prosthetic device 962 throughout most of the entire piston stroke.

The sheath 912 and a cover 916 can define the containment chamber 960. The catheter body 940 can include an outer member 942 coupled to the piston device 914 and the inner rod 944 coupled to the sheath 912. A mounting portion 952 of the biasing device 930 can be fixedly coupled to the inner rod 944. The piston device 914 includes a piston head 920 and a sealing member 922. The ratchet element 924 can be fixedly coupled to the piston head 920 and can include engagement features 926a, 926b (collectively "926").

FIGS. 36 and 37 illustrate a method of deploying the prosthetic device 962. For example, the cover 916 can be moved proximally along elongated catheter body 940. Fluid can flow along a lumen 972 of the inner rod 944 and through a port 980. The fluid can fill a fluid chamber 915 and cause distal movement of the sheath 912. FIG. 37 shows the end 982 of the biasing device 930 contacting the engagement features 926. The biasing device 930, for example, can exert a biasing force that can be overcome by the hydraulic forces to further move the sheath 912 in the distal direction. The prosthetic device 962 moves outwardly through a gap 970. The ratchet element 924 can self-seat within the biasing device 930 and ensure that the biasing device 930 is properly positioned. In some embodiments, the engagement features 926 can be centered relative to the spring end 982. The ratchet element 924 can inhibit or prevent rotation of the piston head 920.

FIG. 38 is an isometric view of the ratchet element 924 configured in accordance with an embodiment of the present technology. The ratchet element 924 can include, for example, a tubular main body 1000 and a plurality of engagement features 926. The engagement features 926 can be, without limitation, fingers, notched members, cantilevered members, or other features capable of mating with the biasing device 930. In some embodiments, the engagement features 926 can extend inwardly to closely surround the inner rod 944 (FIG. 37). In some embodiments, the engagement features 926 can be biased against the inner rod 944 such that the ends of the engagement features 926 slidably contact the inner rod 944. In other embodiments, the ratchet element 924 may include different features and/or have a different configuration.

FIG. 39 is a partially schematic cross-sectional side view of the delivery capsule 910 ready for assembly. The ratchet element 924 can facilitate assembly of the delivery capsule 910. An end 1004 of the inner rod 944 can be inserted into an opening 1006 of the ratchet element 924. The engagement features 926 can help guide the end 1004 into the outer member 942. The piston device 914 can be moved into an interior region 1020 of the sheath 912 such that the sealing member 922 (FIGS. 36 and 37) forms a seal with the inner surface 1028 of the sheath 912. The biasing device 930 (FIGS. 32 and 33) can then be coupled to the inner rod 944.

Figure 40:
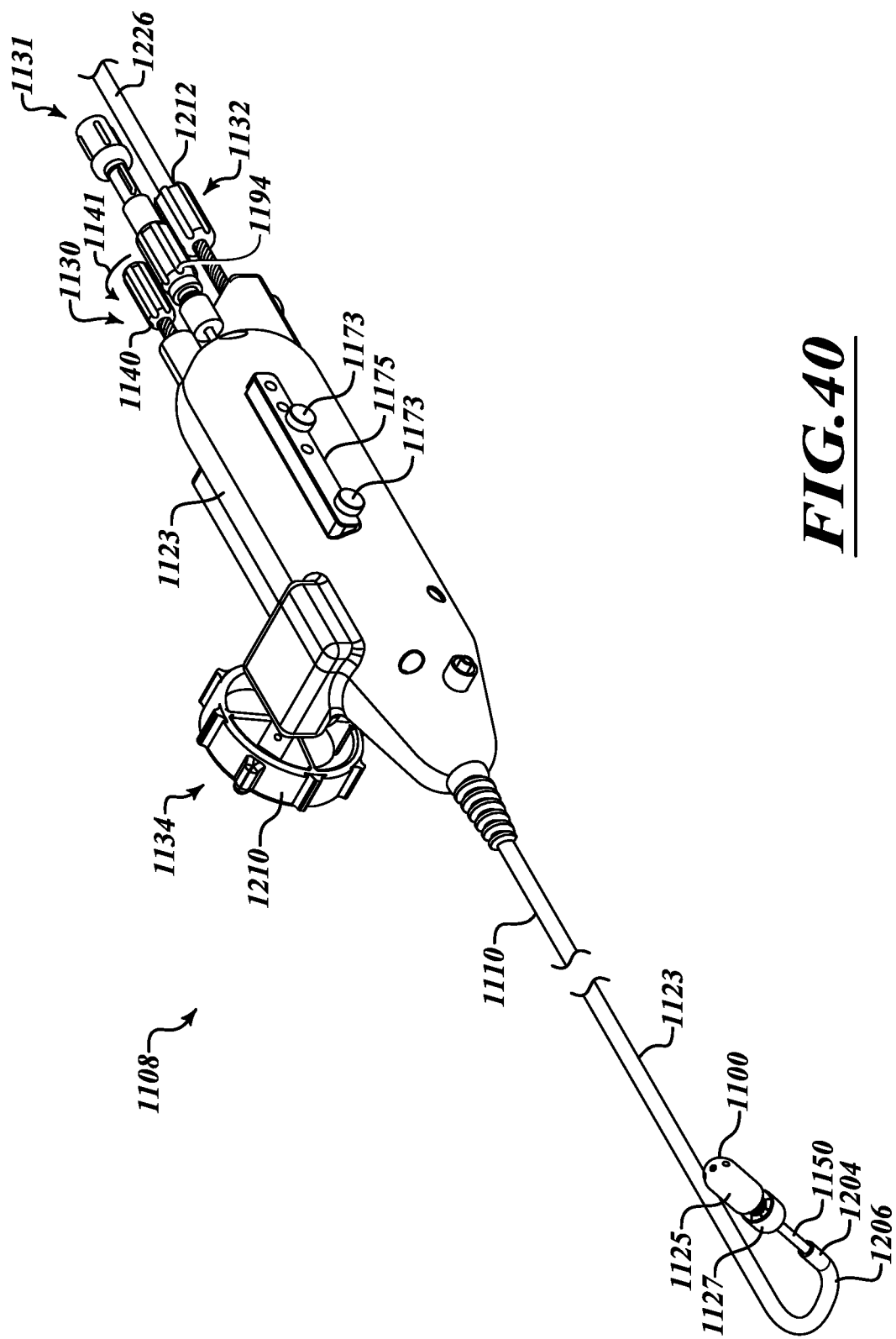
FIG. 40 is an isometric view of a catheter for delivering a prosthetic device in accordance with various embodiments of the present technology.

FIG. 40 is an isometric view of a catheter 1108 configured for delivering a prosthetic device in accordance with various embodiments of the present technology. The catheter 1108 can include an elongated catheter body 1110 ("catheter body 1110"), a control unit 1123, and a delivery capsule 1100. The delivery capsule 1100, for example, includes a hydraulically actuatable distal sheath 1125 and a mechanically actuatable proximal sheath 1127. The control unit 1123 can include a drive mechanism 1130 for actuating the proximal sheath 1127, a rotational control assembly 1131 for rotating the catheter body 1110 relative to control unit 1123, an articulation mechanism 1132, and a side-steering assembly 1134. The control unit 1123, for example, has features and functionality similar to the control unit 210 of FIG. 3, except as detailed below.

Figure 41:
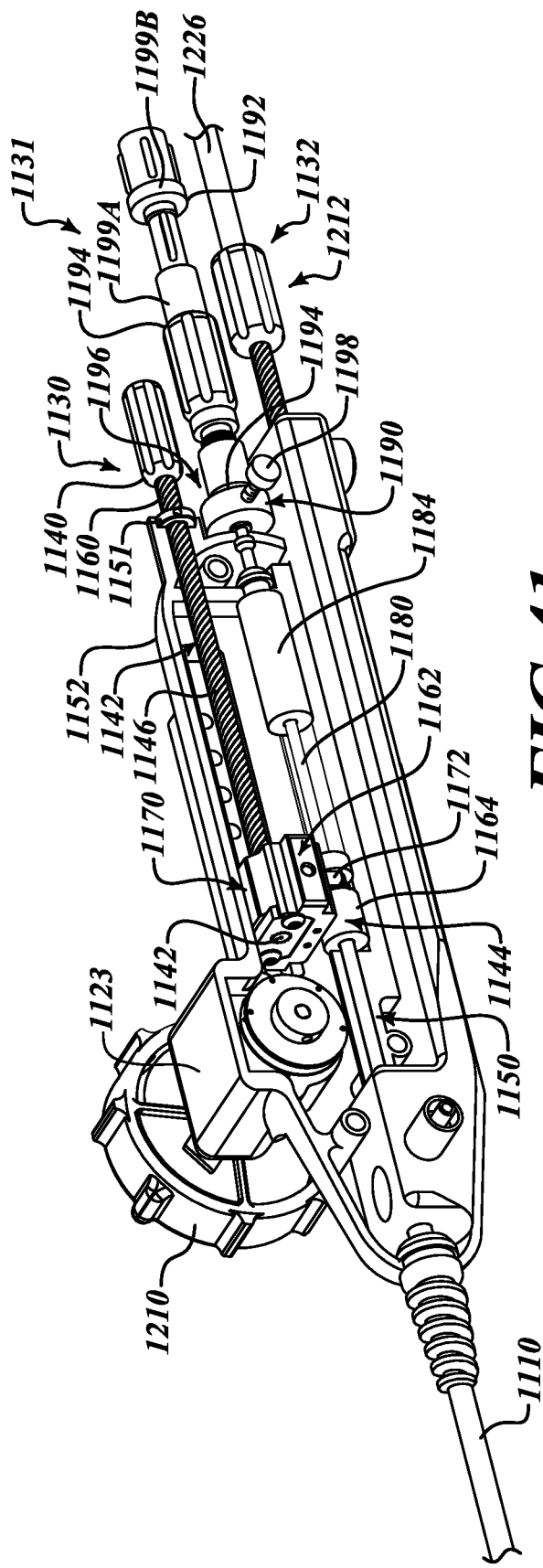
FIG. 41 is an isometric cutaway view of a control unit of the catheter of FIG. 40 in accordance with various embodiments of the present technology.
Figure 42:
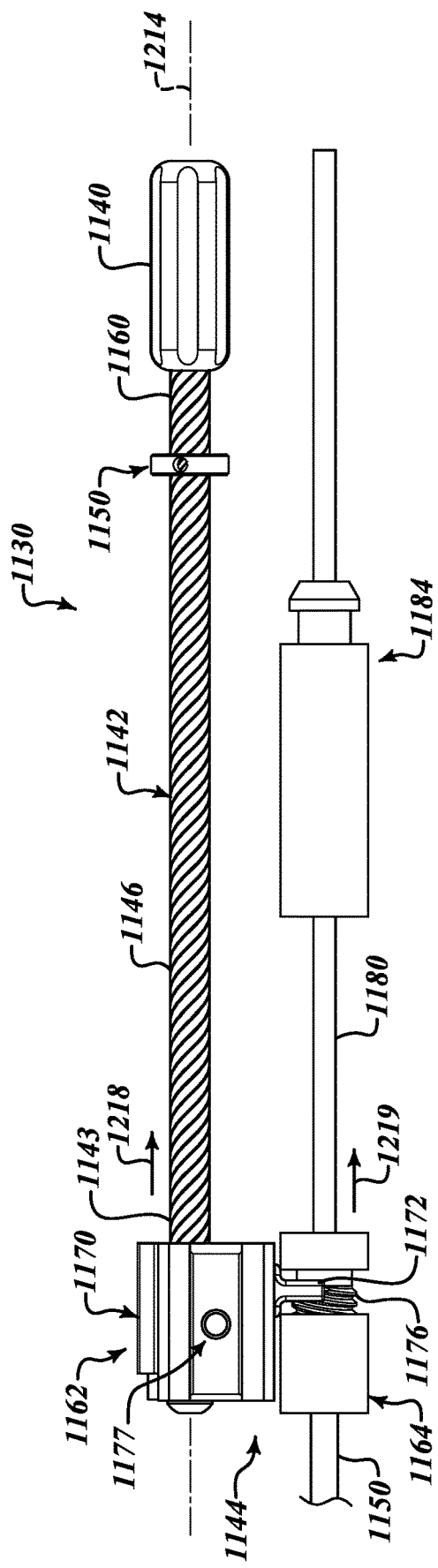
FIG. 42 is a side view of a drive mechanism of the control unit of FIG. 41.

FIG. 41 is a cross-sectional isometric view of the control unit 1123, and FIG. 42 is a side view of the drive mechanism 1130. Referring to FIGS. 40-42 together, the drive mechanism 1130 can include a retraction locking mechanism 1175 (FIG. 40) and the drive mechanism 1139. Generally, the retraction locking mechanism 1175 ("locking mechanism 1175") can be used to lock and unlock the drive mechanism 1130. When the drive mechanism 1130 is unlocked, a user can rotate a handle 1140 to move the proximal sheath 1127.

As best seen in FIG. 41, the drive mechanism 1130 can include the handle 1140, a drive member 1142, and a connection assembly 1144. The drive member 1142 can include a proximal end 1160 connected to the handle 1140, a distal end 1143 (FIG. 42) connected to the connection assembly 1144, and a threaded main body 1146. The main body 1146 extends through an internally threaded collar 1151, which is held by an outer housing 1152. In some embodiments, the drive member 1142 is a drive screw. The length, thread pitch, and other characteristics of the drive member 1142 can be selected based on, for example, the desired travel of the proximal sheath 1127.

Referring to FIG. 42, the connection assembly 1144 can include a hub assembly 1162 and a fitting 1164. The hub assembly 1162 can include a main body 1170 and a coupler 1172. The main body 1170 can include a threaded feature, such as a nut (e.g., a threaded lead-screw nut, a low friction nut, etc.), or a threaded passageway. In some multi-piece embodiments, for example, the main body 1170 can include one or more nuts. In one-piece embodiments, the main body 1170 can have an internally threaded passageway. A receiving feature 1177 (e.g., an opening, a hole, etc.) of the main body 1170 can receive a plunger 1173 (FIG. 40) of the locking mechanism 1175.

The coupler 1172 is configured to engage the fitting 1164 such that translation of the coupler 1172 causes translation of the fitting 1164 along a shaft 1180. In some embodiments, the coupler 1172 extends along opposite sides of the fitting 1164. In other embodiments, the coupler 1172 can be a pin, fastener, or other structure capable of coupling the hub assembly 1162 to the fitting 1164. The fitting 1164 can be a compression fitting that is fixedly coupled to the shaft 1180.

Figure 43:
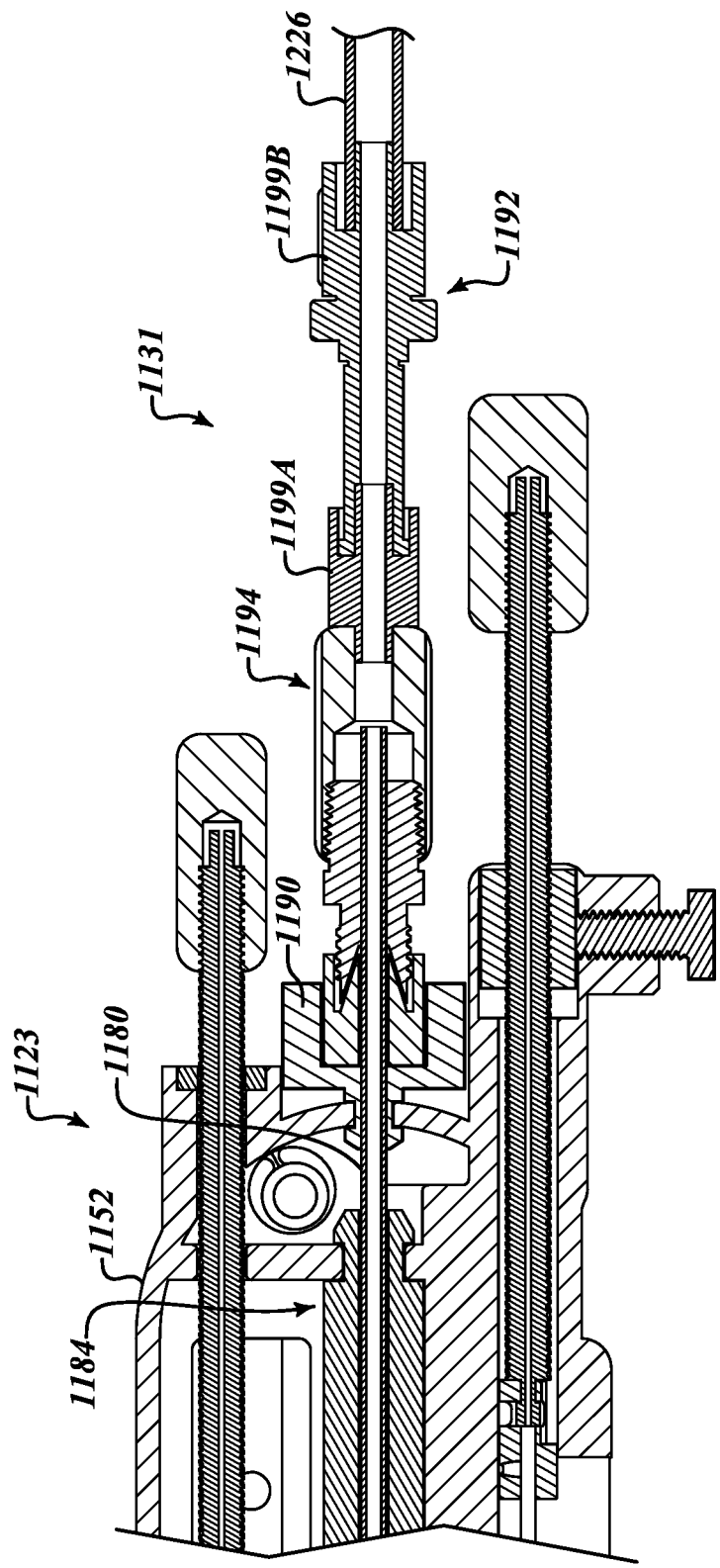
FIG. 43 is a detailed side view of a portion of the control unit of FIG. 41.

Referring to FIGS. 42 and 43 together, the stop 1184 can be positioned along the shaft 1180 and can be translationally fixed to the housing 1152 (FIG. 43) to limit the distance of travel of the fitting 1164. The longitudinal length of the stop 1184 can be increased or decreased to decrease or increase the length of travel of the fitting 1164. In operation, a user can manually rotate the handle 1140 (indicated by arrow 1141 of FIG. 40) to displace the hub assembly 1162 in the proximal direction (indicated by arrow 1218 of FIG. 42). As the hub assembly 1162 moves along the drive member 1142, the coupler 1172 moves the fitting 1164 in the proximal direction (indicated by arrow 1219 of FIG. 42). In this manner, the hub assembly 1162 and fitting 1164 can move together when the hand 1140 is rotated.

As best seen in FIG. 42, the fitting 1164 can include engagement features in the form of threads 1176 that engage the coupler 1172. A user can rotate a handle 1194 (FIGS. 40 and 41) to rotate the shaft 1180 and the fitting 1164 to move the fitting 1164 relative to the hub assembly 1162.

FIG. 43 is a detailed side view of a portion of the control unit 1123 of FIG. 41. The rotational control assembly 1131 can include a mount device 1190, a fitting assembly 1192, and the handle 1194. The fitting assembly 1192, for example, can include a pair of fittings 1199A, 1199B. The fittings 1199A, 1199B can be, without limitation, Luer fittings or other types of fittings that can establish fluid communication with the shaft 1180 and another component, such as a fluid line or other fluid source.

Referring again to FIG. 40, a user can rotate both the steering knob 1210 and handle 1212 to steer the delivery capsule 1100 towards a target site. The rotational control assembly 1131 can be used to rotationally position the delivery capsule 1100 and prosthetic device contained therein about a longitudinal axis of the elongated catheter body 1110. In some embodiments, a posterior side of the prosthetic device can be aligned with the posterior leaflet using, for example, a marker located on the posterior side of the prosthetic device, a marker located on posterior side of the prosthetic device, and/or a marker on one or both of the sheaths 1127, 1125. Once the delivery capsule 1100 is positioned at the target site, the handle 1140 can be rotated about a rotational axis 1214 (FIG. 42) to retract the proximal sheath 1127 in a controlled manner.

Securing tools (e.g., clamps, hemostats, etc.) can be used to position the delivery capsule 1100. The catheter body 1110 includes a nut 1204 coupled to a distal end 1206 of an outer guide sheath 1123. A securing tool can grip the nut 1204 to manually position the delivery capsule 1100. Such embodiments can be manually positioned using open or semi-open procedures. The nut 1204 can be a hexagonal nut or other type of nut configured to be gripped by a securing tool.

Prosthetic devices may have a preferential delivery orientation. For example, if the treatment site is at the mitral valve, the configuration of the prosthetic device may be selected to match the anatomy of the mitral valve. The prosthetic device can be moved to a desired orientation (e.g., a desired rotational position relative to the delivery site, a desired axial position relative to the delivery site, etc.). Because a delivery capsule may be generally symmetric (e.g., rotationally symmetric about its longitudinal axis), it may be difficult to determine the orientation (e.g., rotational position) of the prosthetic device relative to the delivery site. Systems, catheters, and features for orienting prosthetic devices relative to the native anatomy are discussed in connection with FIGS. 44-76. The features for orienting prosthetic devices can be incorporated into the catheters disclosed herein (e.g., catheters discussed in connection with FIGS. 1F and 2A-43).

Figure 44:
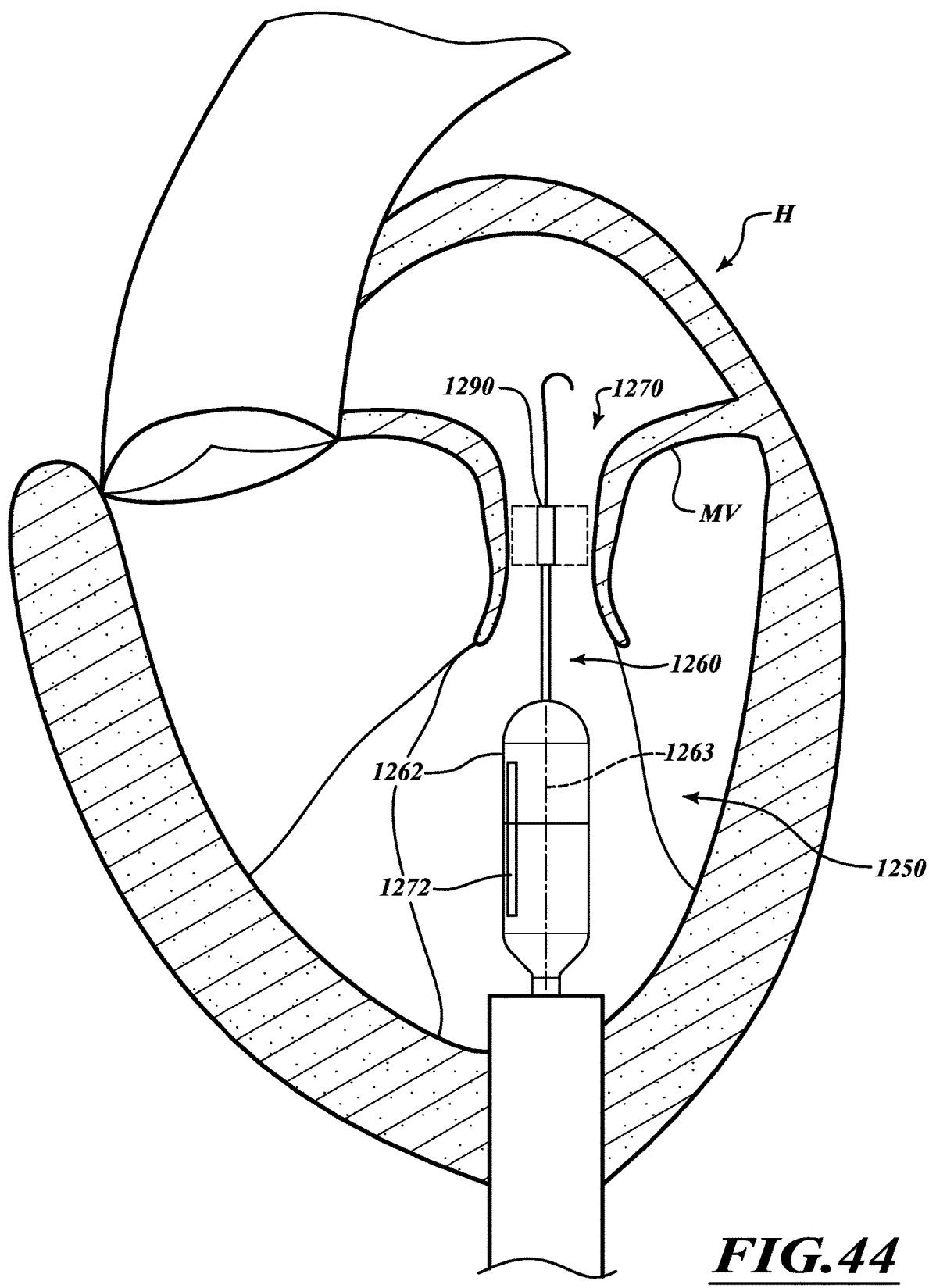
FIG. 44 is a schematic cross-sectional illustration of the heart and a catheter for transapically delivering a prosthetic device within a native mitral valve in accordance with various embodiments of the present technology.

FIG. 44 shows a trans-apical catheter 1250 configured for delivering a prosthetic device within a mitral valve MV. The catheter 1250 can include a positioning assembly in the form of a rotational positioning assembly 1260 ("positioning assembly 1260") and the delivery capsule 1262. The positioning assembly 1260 is positioned in an opening 1270 of the mitral valve MV. An intravalve positioner 1290 of the positioning assembly 1260 and a marker 1272 on delivery capsule 1262 can be used to position the delivery capsule 1262 at a desired rotational position relative to the mitral valve MV. The intravalve positioner 1290 is preferably radiolucent, being composed of a radiopaque material or containing a marker or dye (e.g., radiopaque dye), or it may have radiopaque marker couple or affixed to it. Alternatively, it may be visualized using ultrasound or other suitable technique. When the mitral valve MV closes, the mitral valve MV can move the intravalve positioner 1290 from a misaligned position (shown in dashed line in FIG. 44) to the illustrated aligned orientation in FIG. 45. With the physician visualizing the device using, e.g., fluoroscopy, the delivery capsule 1262 can be rotated about its longitudinal axis 1263 to move the marker 1272 to an aligned position relative to the intravalve positioner 1290 (FIG. 45).

Figure 45:
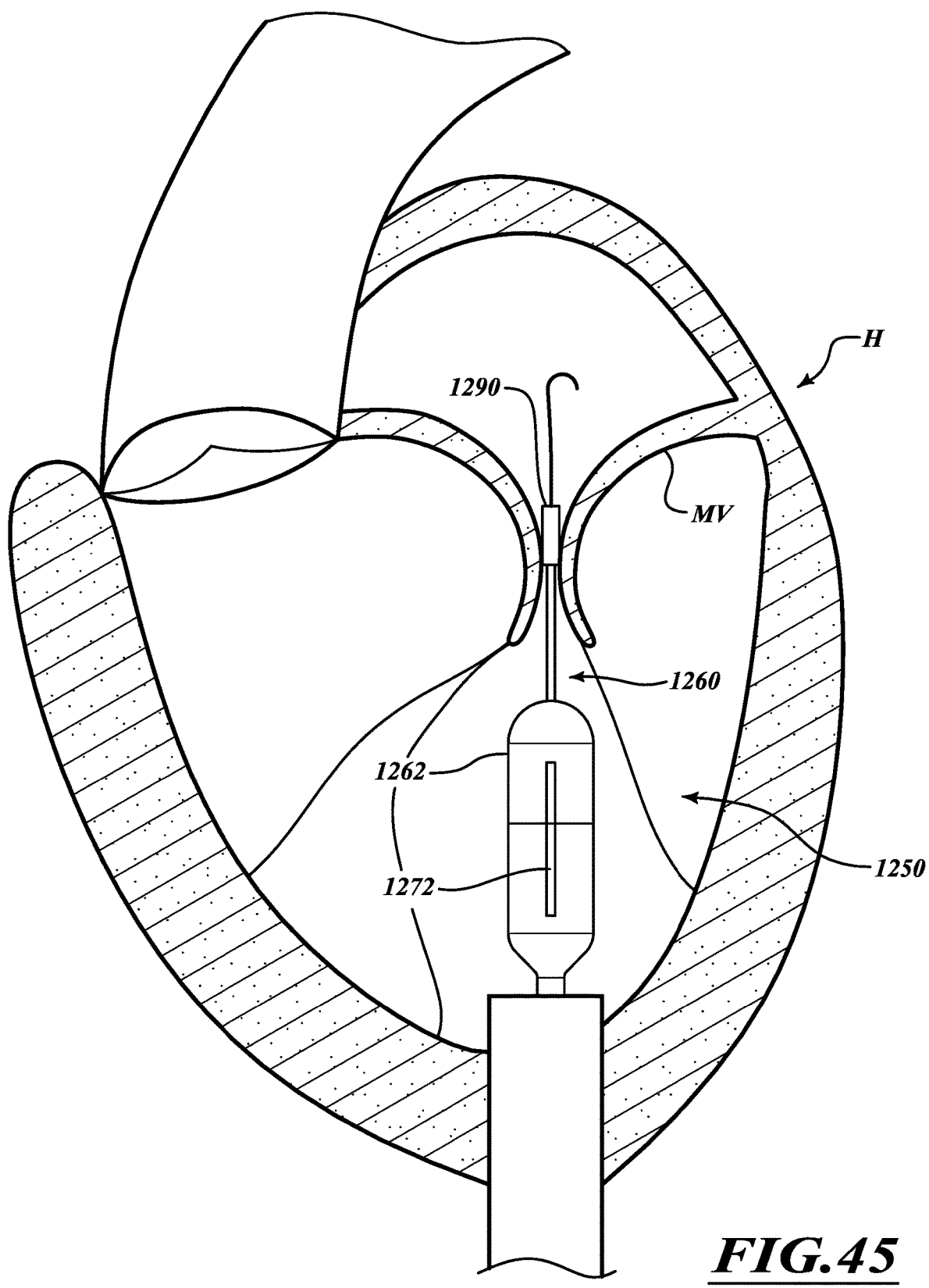
FIG. 45 shows a delivery capsule of the catheter of FIG. 44 aligned with the mitral valve.

FIG. 45 shows the delivery capsule 1262 rotationally aligned with the intravalve positioner 1290. In this arrangement, the marker 1272 and intravalve positioner 1290 can lie in the same plane. The aligned delivery capsule 1262 can then be advanced distally into the mitral valve MV.

FIG. 46 is an isometric view of a distal portion 1280 of a catheter configured in accordance with various additional embodiments of the present technology. The distal portion 1280 can include, for example, the positioning assembly 1260, the delivery capsule 1262, and an elongated catheter body 1282. The positioning assembly 1260 can include the intravalve positioner 1290 and a rod 1292. The intravalve positioner 1290 is configured to rotate about an axis of rotation 1294. The marker 1272 can extend generally parallel to a longitudinal axis 1300 of the delivery capsule 1262. The length of the marker 1272 can be selected to allow convenient determination of the orientation of the marker 1272. In some embodiments, the length L is generally equal to the length of the prosthetic device contained in the delivery capsule 1262. The marker 1272 can be laterally adjacent the prosthetic device and used to axially align the prosthetic device. In the illustrated embodiment, the marker 1272 can be located on an exterior surface 1298 of the delivery capsule 1262. In other embodiments, however, the marker 1272 can be located along an interior surface of the delivery capsule 1262, embedded in the sidewall of the delivery capsule 1262, or at another desired location. Additionally, the marker 1272 can have a wide range of different configurations (e.g., a series of parallel lines, dots, or other shapes, a zig-zag configuration, a serpentine configuration, etc.) and can be at different orientations suitable for evaluating the orientation of the delivery capsule 1262. When the prosthetic device is loaded into the delivery capsule 1262, the orientation of the prosthetic device can be selected based on the position of the marker 1272. For example, a feature (e.g., an anchor, positioning member, or the like) of the prosthetic device can be angularly offset from or angularly aligned with the marker 1272. For example, anchors for contacting leaflets can be offset an angle (e.g., an angle in a plane that is generally perpendicular to the longitudinal axis 1300) about 90 degrees from the marker 1272.

FIG. 47 is a top view of a portion of the positioning assembly 1260, and FIG. 48 is a cross-sectional view of the positioning assembly 1260 of FIG. 47 taken along line 48-48. Referring to FIGS. 47 and 48 together, the intravalve positioner 1290 can be rotatably coupled to the rod 1292. In other embodiments, the intravalve positioner 1290 is fixedly coupled to the rod 1292, which is rotatably coupled to the delivery capsule 1262. The intravalve positioner 1290 can have a generally planar shape and can have a length L, a width W, and a thickness t (FIG. 48) selected to allow natural functioning of the mitral valve MV. The length L can be less than a length of an opening of the mitral valve. The width W can be selected such that the flaps of the mitral valve can securely hold the intravalve positioner 1290 while the delivery capsule 1262 is rotated. When the mitral valve is closed (FIG. 50), the native leaflets seal against the opposing faces of the intravalve positioner so as to seal and prevent backflow of blood through the mitral valve MV.

The intravalve positioner 1290 can comprise a material that enhances viewing. For example, the intravalve positioner 1290 can be made, in whole or in part, of a radiopaque material to provide viewing under fluoroscopy. In some embodiments, the intravalve positioner 1290 can include one or more markers (e.g., radiopaque markers, echocardiographic markers, etc.). The markers of the intravalve positioner 1290 and the marker 1272 (FIG. 46) can be viewed simultaneously. In some embodiments, the intravalve positioner 1290 is a rudder (e.g., a swiveling rudder) with a non-planar configuration. The non-planar configuration can be selected based on the configuration of the anatomical features in which the intravalve positioner is placed. In other embodiments, however, the intravalve positioner 1290 may include other features and/or have a different arrangement.

Referring to FIG. 48, the rod 1292 can include one or more rotation features 1306 (e.g., annular bands, bearings, etc.) that permit rotation of the intravalve positioner 1290 relative to the rod 1292. The rod 1292 can define a guidewire lumen 1310 and can be made, in whole or in part, of plastic, thermoplastic elastomers (e.g., resins such as Pebax®), metal, or combinations thereof. In non-guidewire embodiments, the rod 1292 can have a solid cross-section.

FIGS. 49-53 show one method of positioning the delivery capsule 1262 within the mitral valve MV. Generally, the intravalve positioner 1290 can be positioned within the mitral valve MV. The mitral valve MV can cause rotation of the intravalve positioner 1290 from a misaligned position to an aligned position. The delivery capsule 1262 can be aligned with the intravalve positioner 1290. After aligning the delivery capsule 1262, the delivery capsule 1262 is inserted into the mitral valve MV, and the prosthetic device can be deployed.

FIG. 49 shows a guidewire 1314 positioned between an anterior leaflet AL and a posterior leaflet PL of the mitral valve MV. A tip 1316 of the guidewire 1314 can be positioned in the left ventricle. In this embodiment, the intravalve positioner 1290 can be moved over the guidewire 1314 and inserted into an opening 1320 of the open mitral valve MV. FIG. 49 shows the intravalve positioner 1290 in a misaligned orientation. When the mitral valve MV closes on the intravalve positioner 1290, the anterior leaflet AL and posterior leaflet PL can cause rotation of the intravalve positioner 1290 such that the intravalve positioner 1290 is aligned with the curved coaptation line 1330 defined by a coaptation zone 1328 defined by the anterior leaflet AL and posterior leaflet PL. FIG. 50 shows the intravalve positioner 1290 generally parallel to the coaptation line 1330. As the mitral valve MV opens and closes, it can continue to reposition the intravalve positioner 1290 along the coaptation line 1330.

Referring to FIG. 50, the marker 1272 is angularly offset from the intravalve positioner 1290 relative to a longitudinal axis 1300 of the catheter. The catheter body 1282 can be rotated clockwise about the longitudinal axis 1300, as indicated by arrow 1342, to align the marker 1272 with the positioner 1290. FIG. 51 (and FIG. 45 described previously) show the marker 1272 aligned with the intravalve positioner 1290 relative to the longitudinal axis 1300. FIG. 45, for example, shows the marker 1272 aligned with intravalve positioner 1290 in the superior-inferior direction when viewed from the side.

Figure 53:
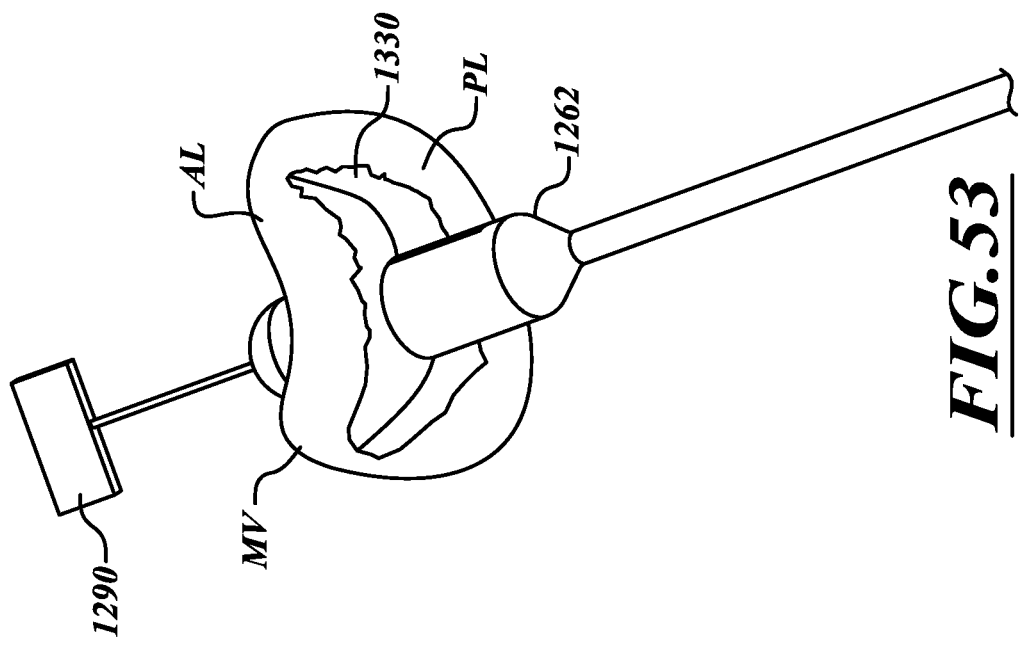
Figure 52:
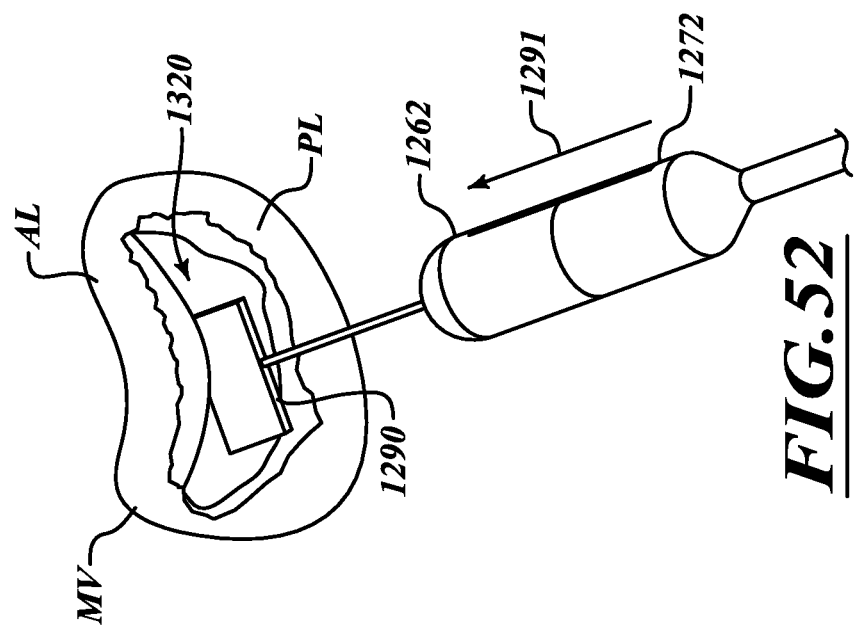

FIG. 52 shows the delivery capsule 1262 ready to be delivered into the mitral valve MV. The delivery capsule 1262 can be translated distally, indicated by arrow 1291, without an appreciable amount of rotation to maintain alignment of the delivery capsule 1262. The marker 1272 can be viewed to confirm that alignment has been maintained. FIG. 53 shows the delivery capsule 1262 ready to deploy a prosthetic device (not shown). The marker 1272, for example, can be generally positioned along the coaptation line 1330. The delivery capsule 1262 can include retaining features (e.g., posts, pins, or the like) that can inhibit rotation of the prosthetic device, thereby maintaining alignment of the prosthetic device. When properly positioned, the delivery capsule 1262 can be opened to release the prosthetic device.

Figure 56:
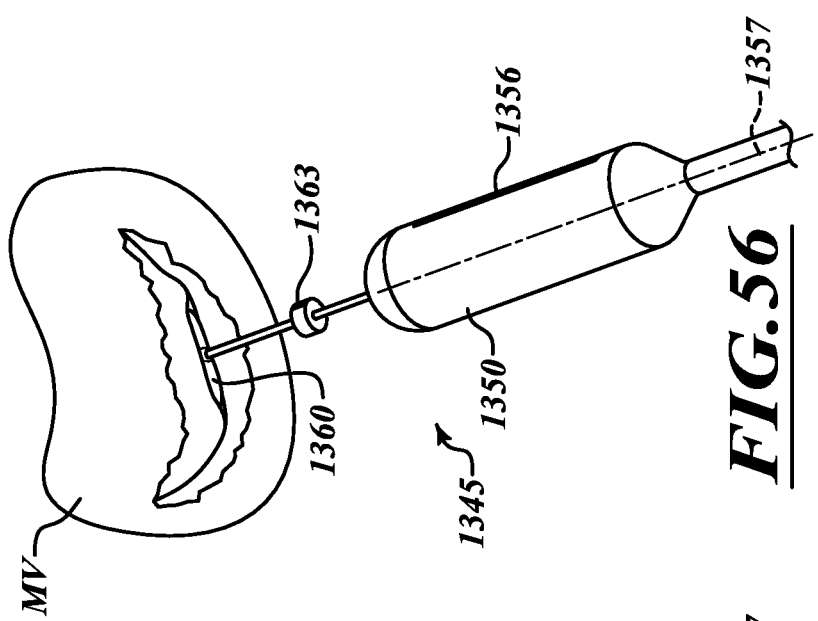
FIGS. 54-56 are a series of views of a method of aligning a delivery capsule with a native mitral valve in accordance with another embodiment of the present technology.
Figure 55:
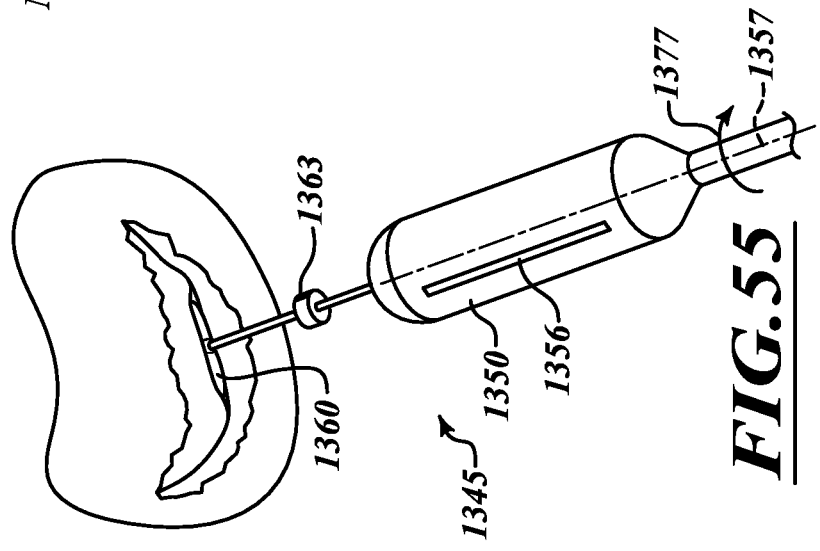
Figure 54:
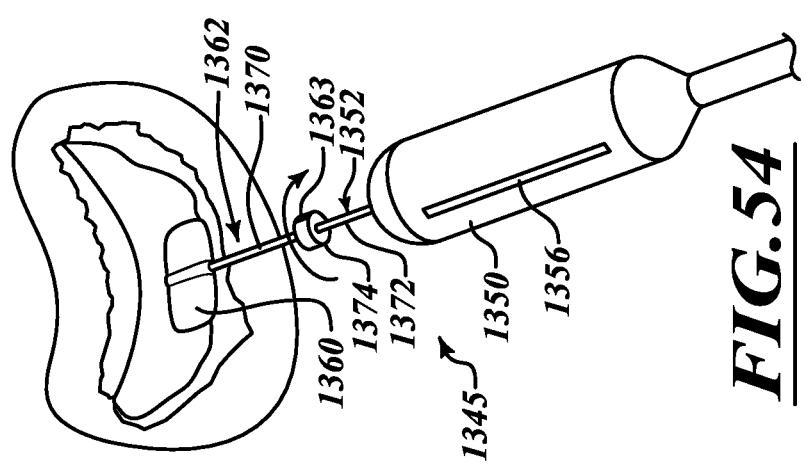

FIGS. 54-56 are a series of views of a method of positioning a distal portion 1345 of a catheter in accordance with another embodiment of the present technology. Referring to FIG. 54, for example, the distal portion 1345 can include a delivery capsule 1350 and a positioning assembly 1352. The delivery capsule 1350 can include an alignment feature in the form of a marker 1356. The positioning assembly 1352 can include an intravalve positioner 1360 and a rod assembly 1362. The rod assembly 1362, for example, can include a distal rod member 1370, a proximal rod member 1372, and an alignment feature 1374. In this embodiment, the distal rod member 1370 is fixedly coupled to the intravalve positioner 1360 and the alignment feature 1374. The proximal rod member 1372 may be rotatably coupled to the distal rod member 1370 and fixedly coupled to the delivery capsule 1350. The alignment feature 1374 can include, without limitation, one or more bearings, swivels, or other features that allow rotation between the rod members 1370, 1372.

In operation, when the mitral valve MV closes, the anterior leaflet AL and the posterior leaflet PL can move the intravalve positioner 1360 to an aligned position. FIGS. 55 and 56, for example, show the intravalve positioner 1360 is an aligned position. The delivery capsule 1350 of FIG. 55 can be rotated (as indicated by arrow 1377) about its longitudinal axis 1357 to align the marker 1356 with an alignment feature 1363. For example, the delivery capsule 1350 of FIG. 55 can be rotated about 90 degrees about the longitudinal axis 1357 in a clockwise direction to align the marker 1356 with the alignment feature 1363. FIG. 56 shows the markers 1356, 1363 aligned with one another relative to the longitudinal axis 1377. The aligned delivery capsule 1350 of FIG. 56 is ready to be advanced into the mitral valve MV.

The delivery capsules discussed in connection with FIGS. 44-56 can be aligned with the mitral valve prior to positioning the delivery capsules within the valve. However, delivery capsules of catheters can also be aligned with mitral valves when the delivery capsules are positioned within the mitral valves, as discussed below in connection with FIGS. 57-66.

Figure 57:
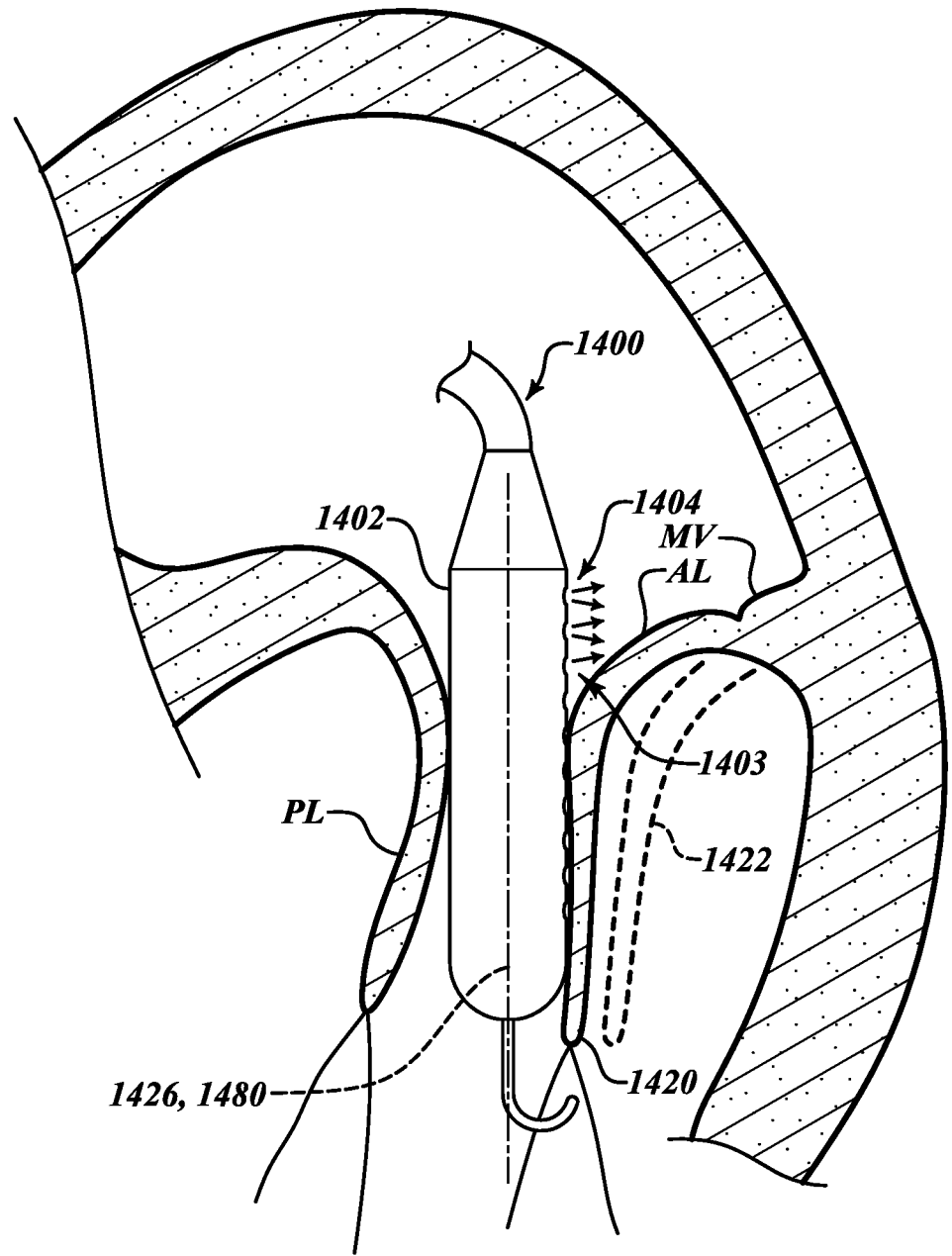
FIG. 57 is a schematic cross-sectional illustration of the heart and a distal portion of a catheter positioned in a mitral valve in accordance with another embodiment of the present technology.
Figure 58:
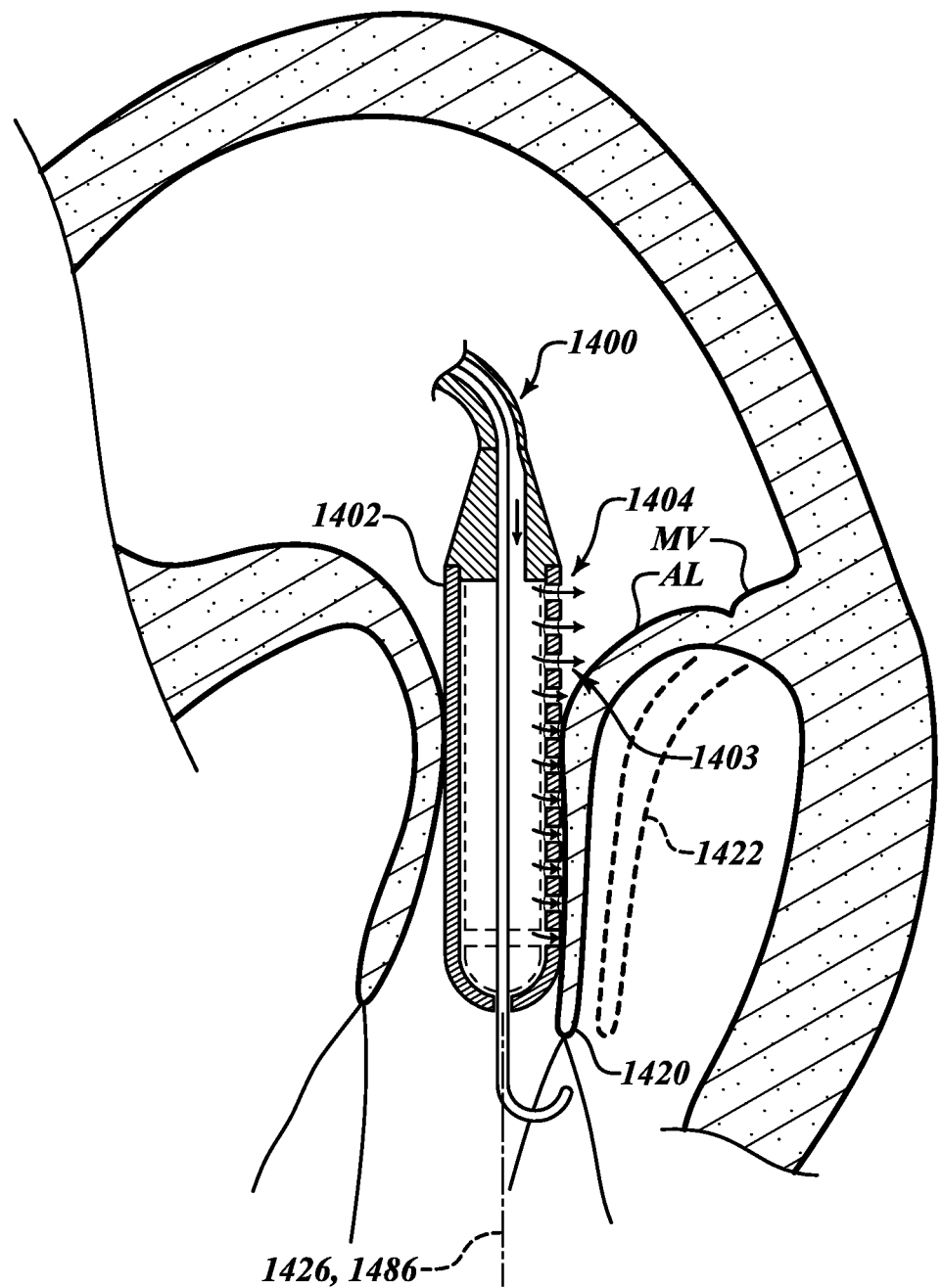
FIG. 58 is a cross-sectional side view of the distal portion of FIG. 57.

FIG. 57, for example, shows a distal portion 1400 of a catheter positioned in a mitral valve MV. FIG. 58 is a cross-sectional view of the distal portion 1400. Generally, distal portion 1400 can interact with tissue to indicate the position of the distal portion 1400 relative to one or more native anatomical structures of the heart. In some embodiments, for example, the distal portion 1400 can apply a fluidic force to tissue to alter the position of the tissue, thereby indicating the orientation (e.g., longitudinal position, rotational position, etc.) of the distal portion 1400. For example, the distal portion 1400 can output fluid to move the anterior leaflet, posterior leaflet, or other anatomical structures of the mitral valve MV. Additionally or alternatively, the distal portion 1400 can output fluid to move the distal portion 1400 relative to one or more anatomical structures of the mitral valve MV.

FIGS. 57 and 58 show a position indicator 1403 in the form of ports 1404 outputting fluid (represented by arrows) to move the anterior leaflet AL from an initial position 1420 to a displaced position 1422 (shown in dashed line). The position of the anterior leaflet AL can be viewed, for example, via echocardiography. The delivery capsule 1402 can be rotated about an axis of rotation 1426 to rotationally align the deliver device 1402 with the mitral valve MV. The maximum amount of displacement of the anterior leaflet AL caused by the fluid will typically occur when the ports 1404 face the anterior leaflet AL. Once the delivery capsule 1402 is located at the desired orientation, the delivery capsule 1402 can deliver a prosthetic device.

Figure 59:
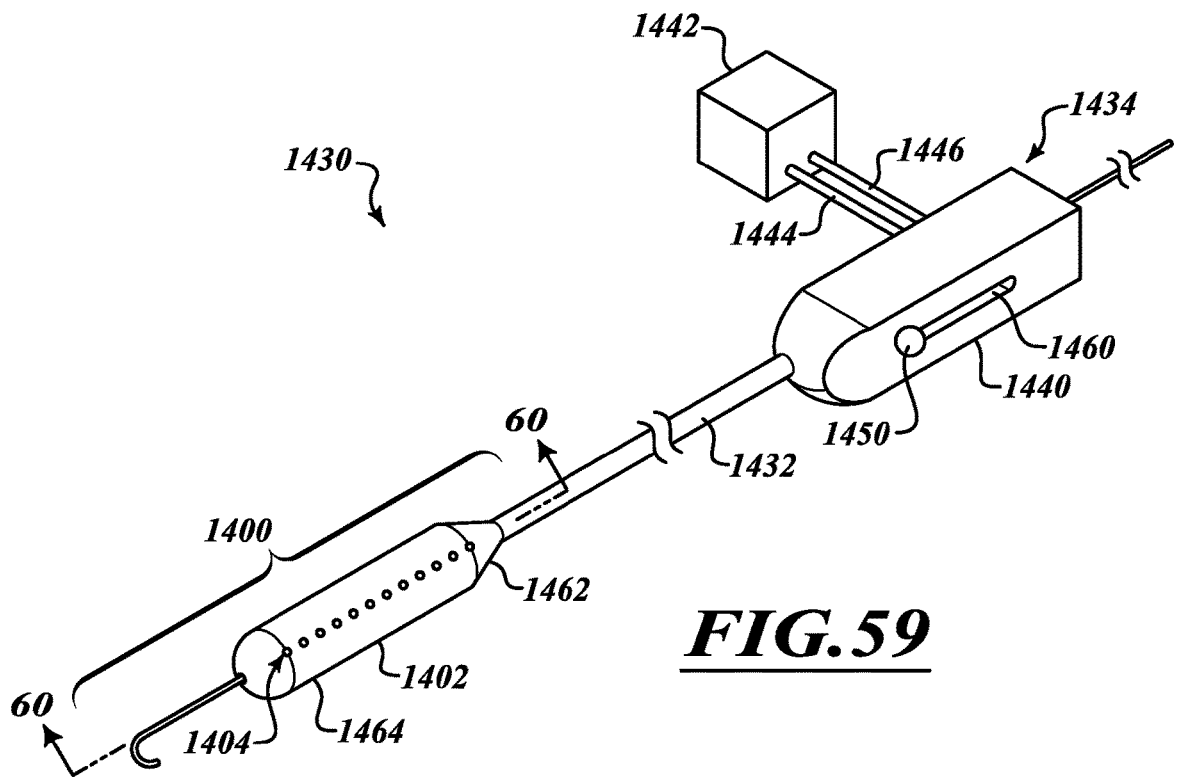
FIG. 59 is an isometric view of a system for delivering a prosthetic device in accordance with various embodiments of the present technology.

FIG. 59 is an isometric view of a catheter system 1430 for delivering a prosthetic device configured in accordance with various embodiments of the present technology. The catheter system 1430 can include, for example, an elongated catheter body 1432 ("catheter body 1432"), a control unit 1434, and a fluid system 1442. The fluid system 1442 is configured to independently deliver fluids to the lines 1444, 1446. Fluid flowing through the line 1444 can be delivered distally along the catheter body 1432 and out of the ports 1404. For example, fluid flowing through the line 1446 can be delivered distally along the catheter body 1432 and used to hydraulically operate the delivery capsule 1402. The fluid system 1442 can include, without limitation, one or more pressurization devices, containers (e.g., internal tanks or containers), valves, controllers, and/or power sources. The control unit 1434 can include an actuator element 1450 movable along a slot 1460 to move a cover 1462 of the delivery capsule 1402. In other embodiments, the control element 1450 can be used to move the sheath 1464 distally.

Figure 60:
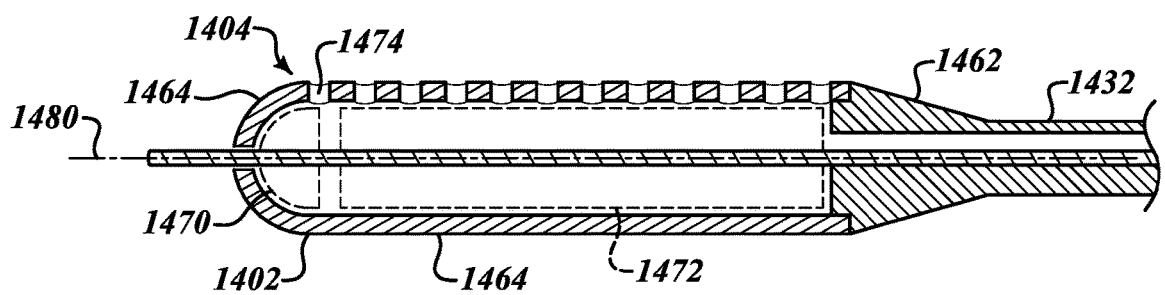
FIG. 60 is a cross-sectional view of a distal portion of the system taken along line 60-60 of FIG. 59.

FIG. 60 is a cross-sectional view of the distal portion 1400 of the catheter system 1430 taken along line 60-60 of FIG. 59. The delivery capsule 1402 can include, for example, a piston device 1470 (illustrated schematically in dashed line) positioned within a sheath 1464. The ports 1404, for example, may comprise a plurality of through-holes 1474 (only one port is identified). The through-holes 1474 can be spaced apart from one another and positioned in a linear arrangement to apply a radially directed fluid force to the mitral valve MV. In some embodiments, for example, the through-holes 1474 are substantially evenly spaced apart from one another in a direction that is substantially parallel to a longitudinal axis 1480 of the delivery capsule 1402. In other embodiments, however, the through-holes 1474 can define a serpentine configuration, a substantially zig-zag configuration, or other suitable configuration and pattern.

FIGS. 61-64 show a method of positioning the delivery capsule 1402 in accordance with one embodiment of the present technology. The prosthetic device 1472 may have a preferential deployment position to engage, for example, tissue of the heart (e.g., anterior leaflet AL, posterior leaflet PL, anterior annulus AA, posterior annulus PA, etc.). For example, the portion of the prosthetic device 1472 adjacent the ports 1404 can be configured to engage the anterior tissue (e.g., anterior leaflet AL, anterior annulus AA, etc.). Once the delivery capsule 1402 is at the desired position, the delivery capsule 1402 can release the prosthetic device 1472.

Figure 61:
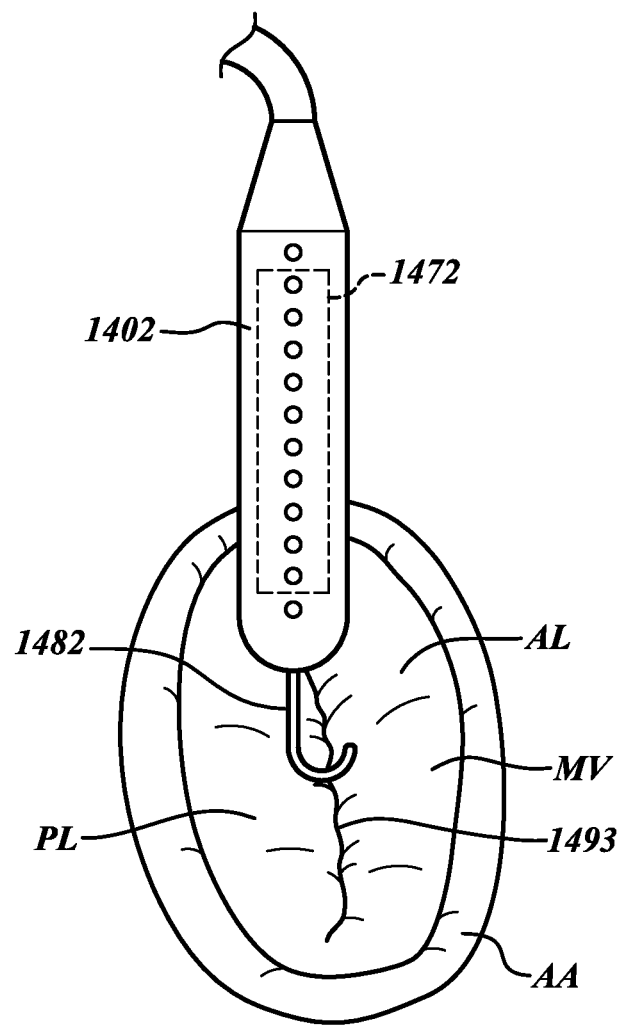
FIGS. 61-65 are a series of views of a method of positioning the distal portion of FIG. 60 in accordance with various embodiments of the present technology.

Referring first to FIG. 61, the delivery capsule 1402 is ready to be inserted into the mitral valve MV. A guidewire 1482 can be inserted between the leaflets PL, AL. After positioning the guidewire 1482, the delivery capsule 1402 can be advanced distally over the guidewire 1482 and into the mitral valve MV. The length of the delivery capsule 1402 positioned directly between the leaflets PL, AL can be selected based upon the size of a prosthetic device 1472 (shown schematically in dashed line in FIG. 61), the position of the prosthetic device 1472 relative to the delivery capsule 1402, and other procedure parameters.

Figure 62:
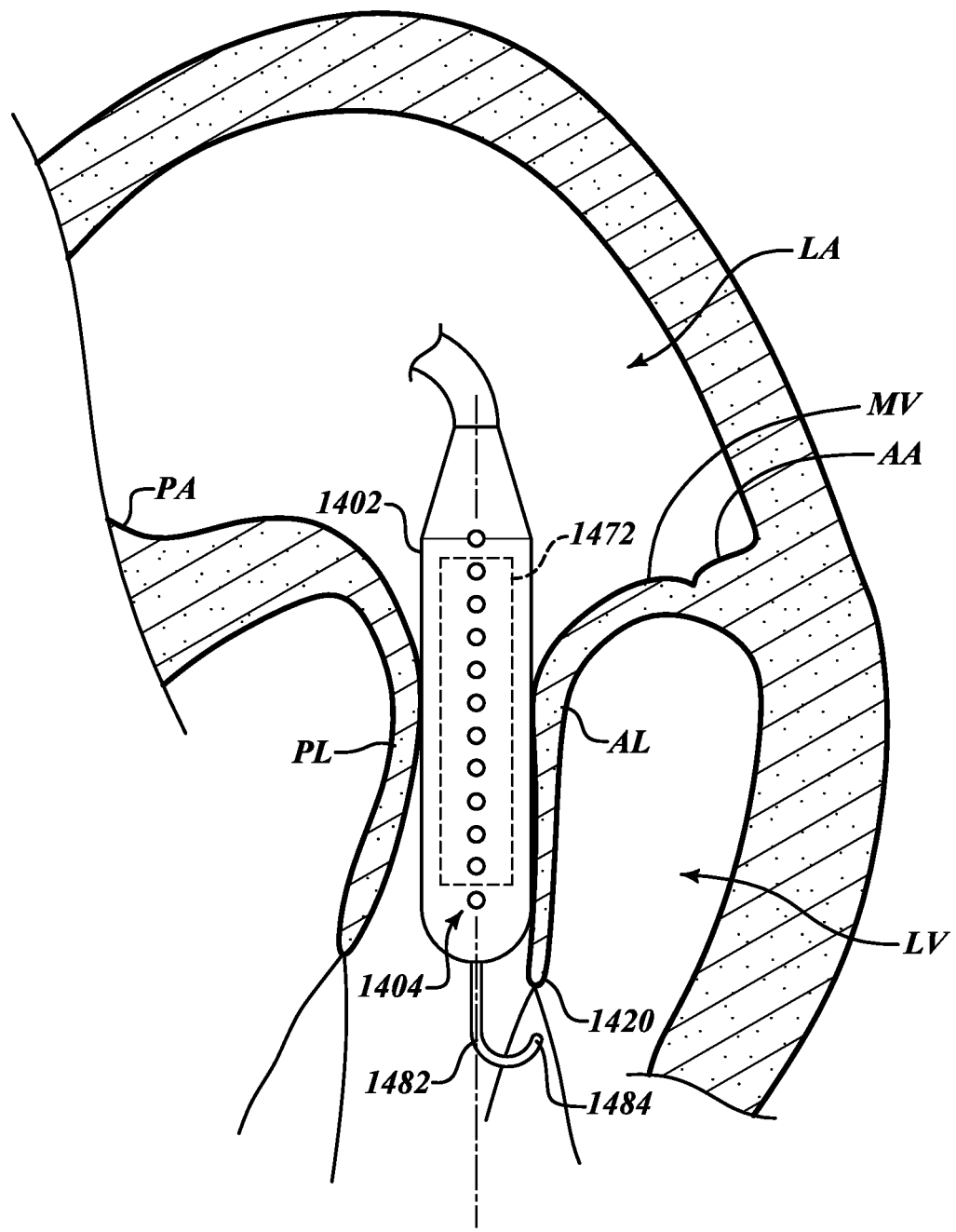

FIG. 62 shows the delivery capsule 1402 positioned in the mitral valve MV. A tip 1484 of the guidewire 1482 is positioned in the left ventricle LV. The ports 1404 are arranged to face a coaptation line 1493 (FIG. 61) between the anterior and posterior leaflets AL, PL. Accordingly, if fluid is delivered out of the ports 1404, the fluid can flow along the coaptation line 1493 (FIG. 61) and cause minimal displacement of the leaflets PL, AL. Additionally, movement (if any) of the posterior and anterior leaflets PL, AL may not be clearly identifiable under many visualization techniques. Thus, it may be difficult to determine whether the ports 1404 face the right side or left side of the mitral valve.

Figure 63:
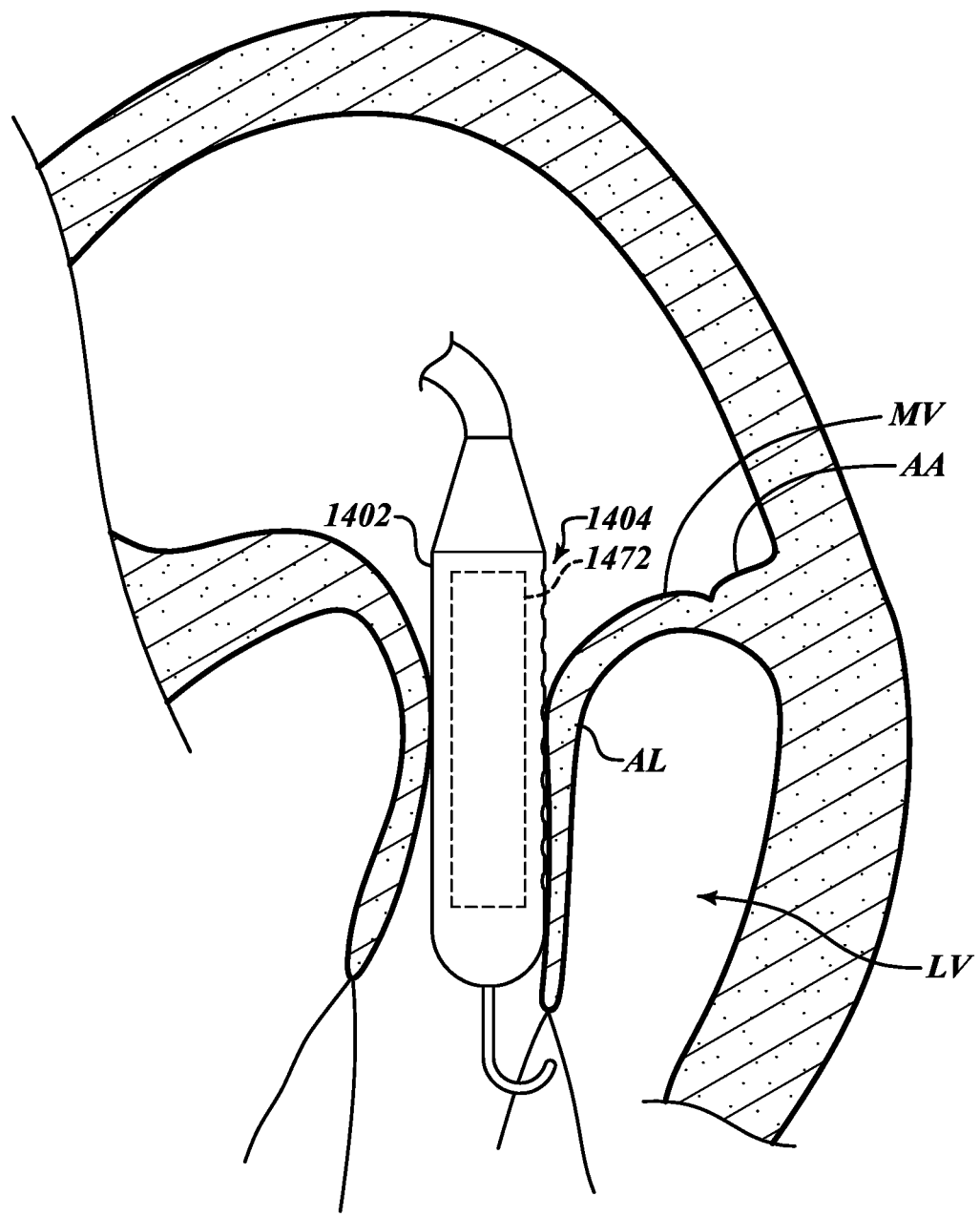
Figure 64:
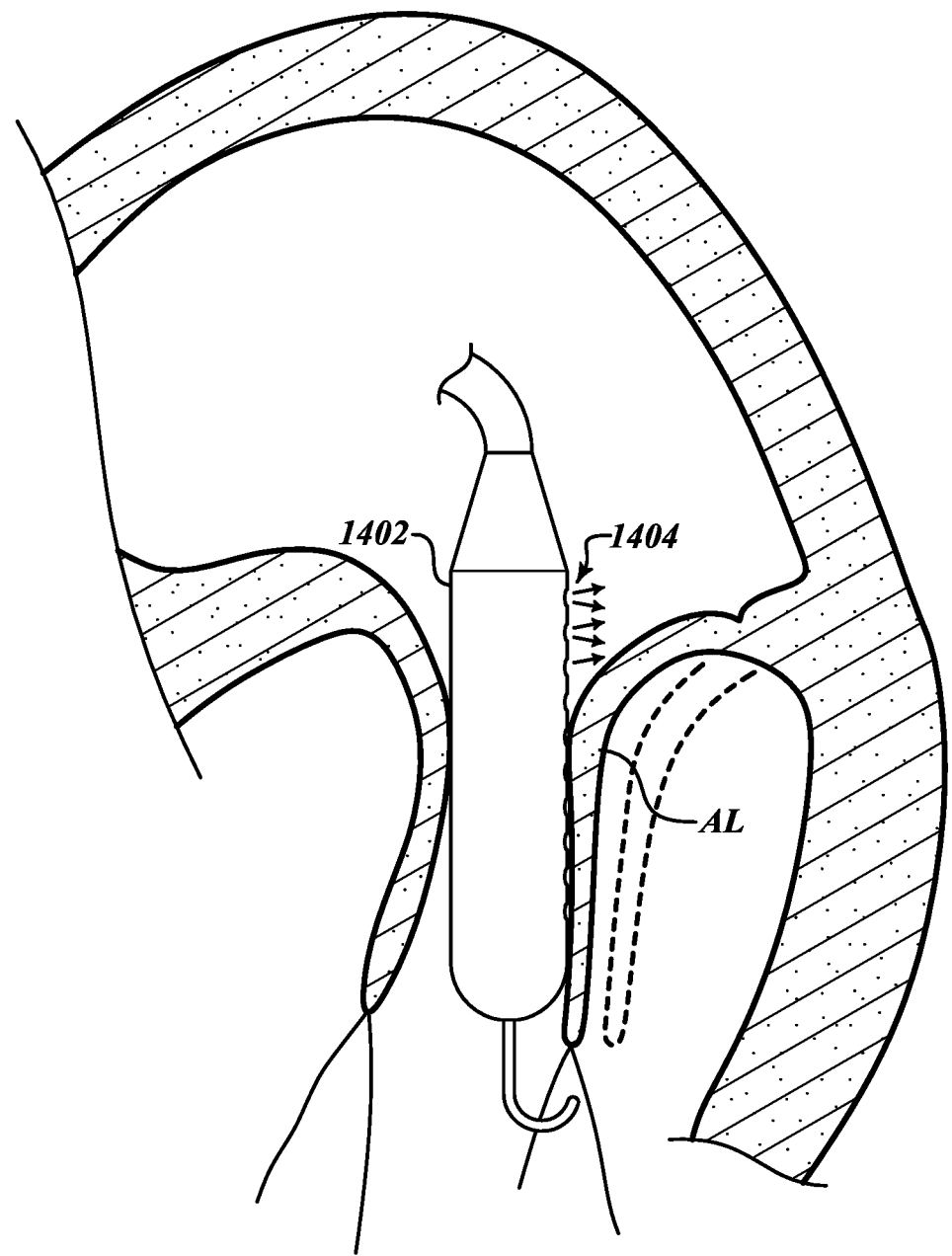

FIGS. 63 and 64 shows the ports 1404 facing the anterior leaflet AL. Referring to FIG. 63, for example, the anterior leaflet AL can contact the delivery capsule 1402. Fluid can be delivered out of the ports 1404 to, for example, displace the anterior leaflet AL. FIG. 64 shows fluid (represented by arrows) outputted towards the anterior leaflet AL. The fluid can be outputted to maintain a gap between the anterior leaflet AL and the delivery capsule 1402. For example, the anterior leaflet AL can move between a fully open position and a partially open position (shown in dashed line). In some procedures, the fluid can keep the anterior leaflet AL in a fully open position (e.g. spaced well apart from the delivery capsule 1402 and adjacent to the heart wall).

Figure 65:
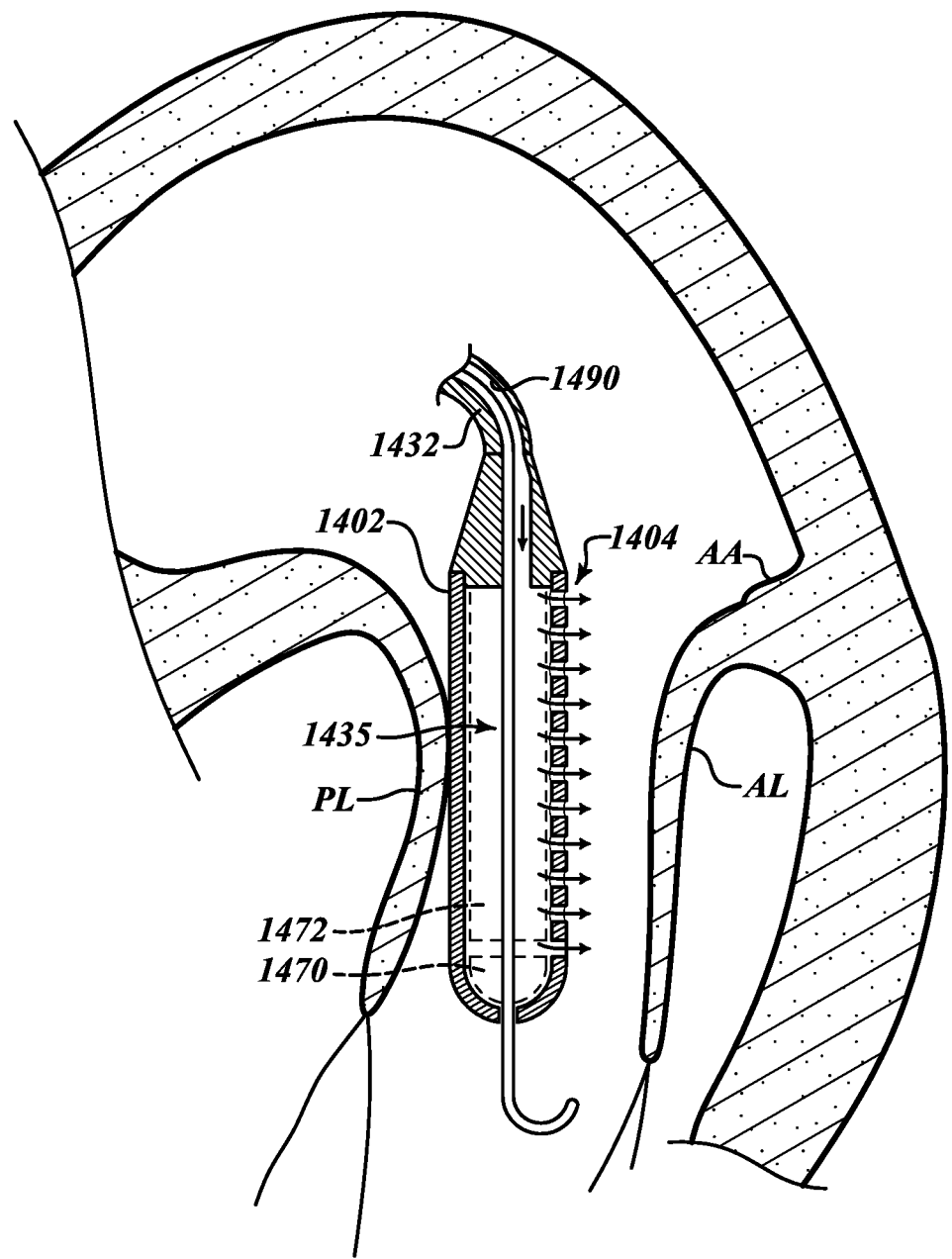

Referring to FIG. 65, fluid can flow along a lumen 1490, into a containment chamber 1435, and through the ports 1404. Other configurations can be used to deliver fluid to the ports 1404. The fluid can be saline or other suitable biocompatible fluid. In some embodiments, the fluid is a viewable fluid (e.g., a radio opaque fluid, a fluid containing a radiopaque material or markers, or the like). The fluid can be viewed to evaluate the orientation of the delivery capsule 1402.

Figure 66:
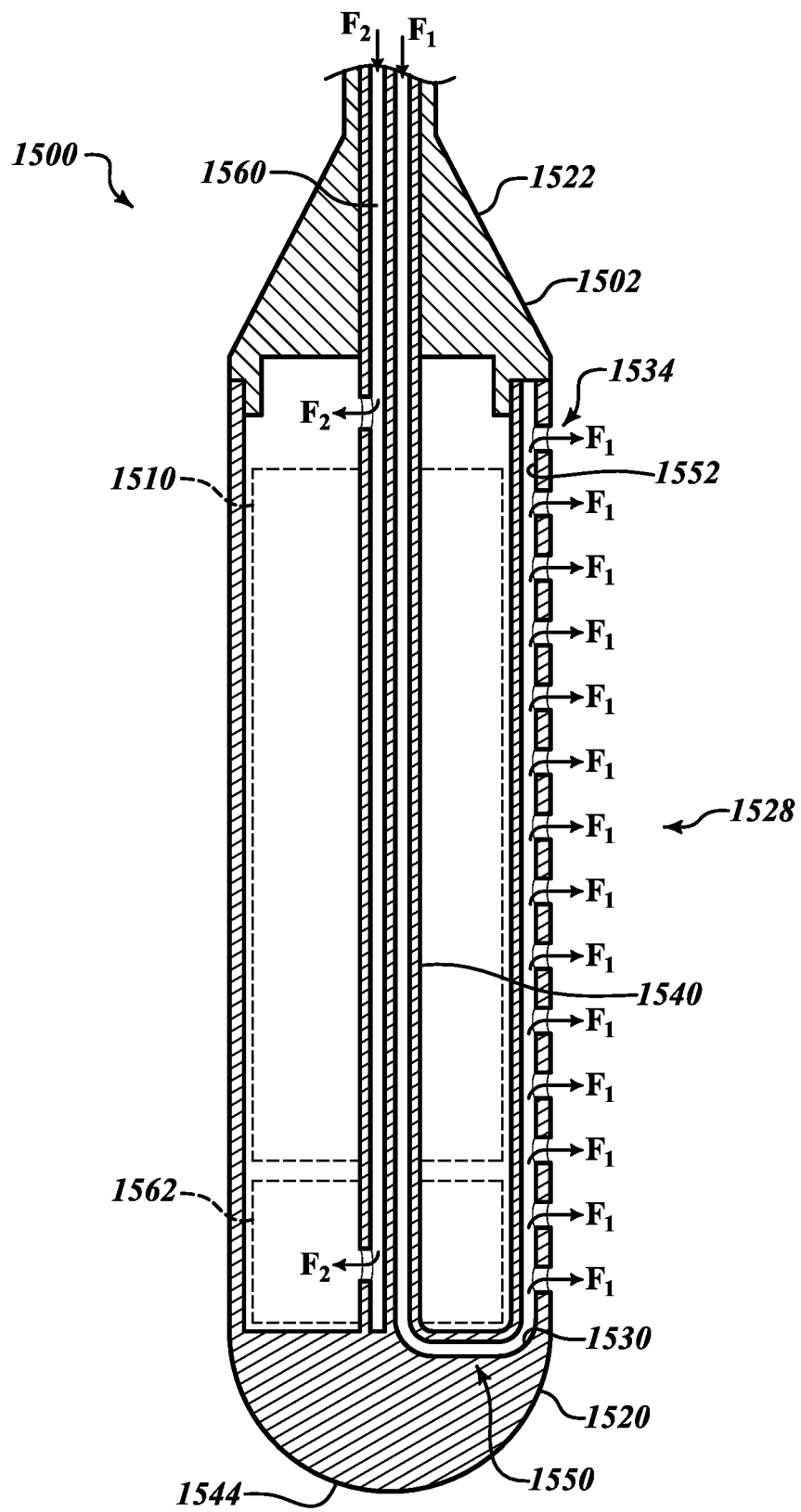
FIG. 66 is a cross-sectional side view of a distal portion of a catheter in accordance with various embodiments of the technology.

FIG. 66 is a cross-sectional view of a distal portion 1500 of a catheter configured in accordance with various embodiments of the technology. The distal portion 1500 can include, for example, a delivery capsule 1502 configured to output fluid without disrupting a prosthetic device 1510. Fluids $F_1$, $F_2$ can be independently delivered through the delivery capsule 1502 to position the delivery capsule 1402 and actuate the delivery capsule 1502 at different times. The delivery capsule 1502 can include a distal sheath 1520 and a proximal sheath or cover 1522. The distal sheath 1520 can include a position indicator 1528 and a passageway 1530. The position indicator 1528 can include a plurality of spaced apart ports 1534 in fluid communication with the passageway 1530. The passageway 1530 extends proximally through a rod 1540 of the distal sheath 1520. To position the delivery capsule 1502, the fluid $F_1$ can flow distally along the passageway 1530 towards an end 1544 of the distal sheath 1520. The fluid $F_1$ can flow through a U-shaped section 1550 of the passageway 1530 and proceed proximally along a feed passageway 1552. The fluid $F_1$ is configured to flow along the feed passageway 1552 and out of the ports 1534.

Fluid $F_2$ can flow distally along a lumen 1560 and, in some embodiments, can operate a piston device 1562 (shown schematically in dashed line). The fluid $F_2$ can be delivered to loosen the distal sheath 1520 from the proximal sheath 1522. The fluid $F_1$ can then be outputted to position the delivery capsule 1502. After positioning the delivery capsule 1502, the flow of the fluid $F_1$ can be inhibited or stopped, and the fluid $F_2$ can be used to hydraulically actuate the distal sheath 1520. In other embodiments, the delivery capsule 1502 may include a different arrangement and/or have different features.

Figure 67:
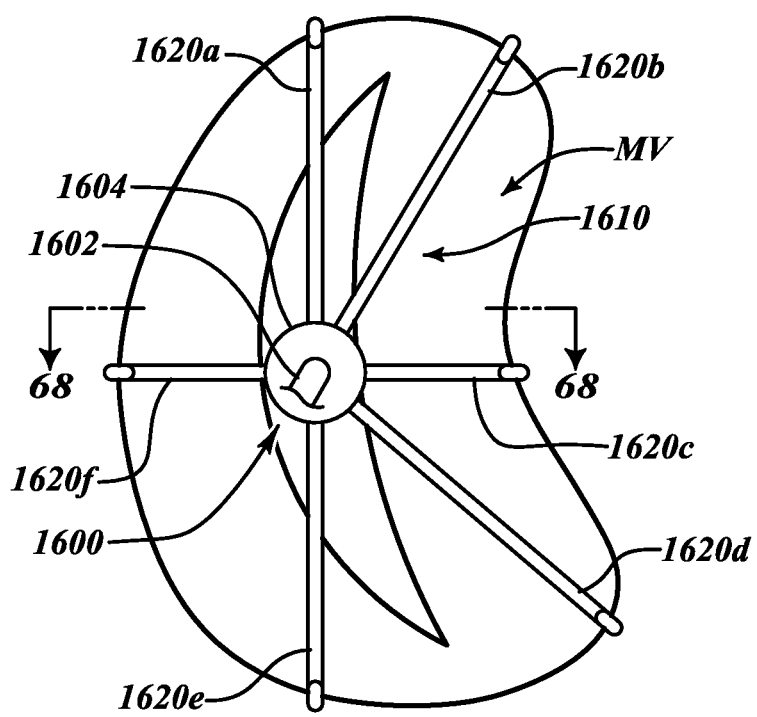
FIG. 67 is a top view of a distal portion of a catheter positioned in a native mitral valve in accordance with various embodiments of the technology.
Figure 68:
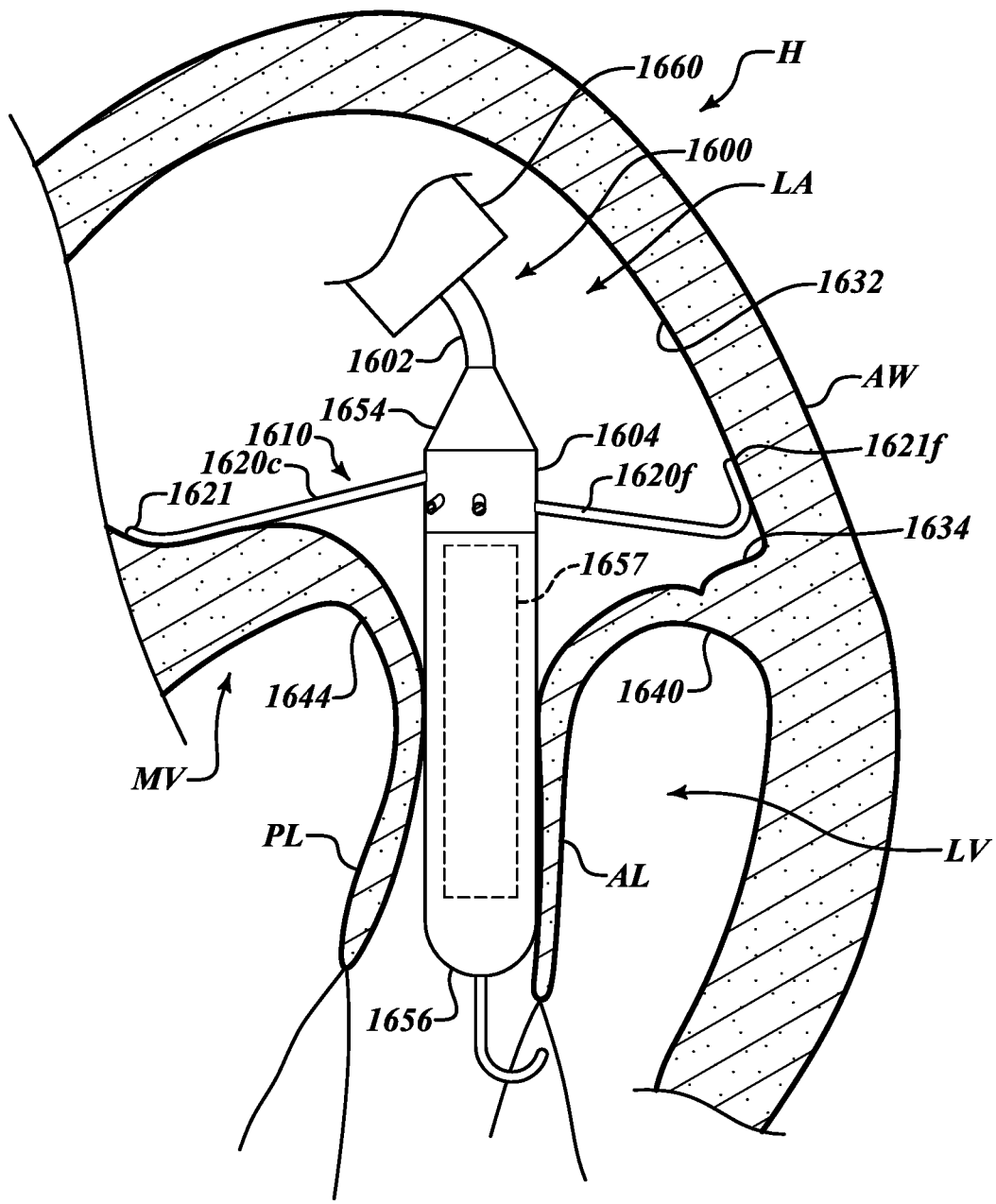
FIG. 68 is a cross-sectional side view of the distal portion of FIG. 67 taken along line 68-68.

FIGS. 67 and 68 show a distal portion 1600 comprising an elongated catheter body 1602 ("catheter body 1602"), a delivery capsule 1604, and a position indicator in the form of a mechanical positioner assembly 1610 movable between a delivery state for delivery through a guide catheter 1660 and a tissue-contacting state for engaging tissue of the heart. The positioner assembly 1610, for example, can include an array of positioners in the form of deployable members 1620a-f (collectively "deployable members 1620") configured to help position the delivery capsule 1604 relative to the mitral valve MV. For example, the deployable members 1620 can be deployed to guide the delivery capsule 1604 into the mitral valve MV, to keep the delivery capsule 1604 positioned within the mitral valve MV, and/or to otherwise position (e.g., axially align, rotationally align, etc.) the delivery capsule 1604 relative to anatomy of the heart. The deployable members 1620 can be made, in whole or in part, of radiopaque material or may comprise one or more radiopaque markers. The members 1620 can be viewed under fluoroscopy to help position the delivery capsule 1604 and/or locate anatomical features of the heart. In some embodiments, tips 1621 of the members 1620 can carry radiopaque markers used to locate the annulus 1634, the inner surface 1632 of the atrial wall AW, or other anatomical features of interest.

Figure 69:
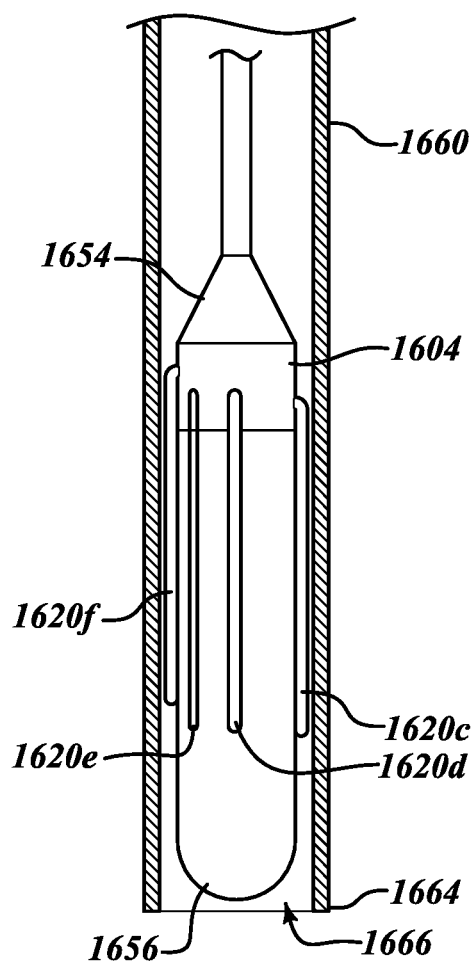
FIG. 69 shows a distal portion of a catheter in a guide catheter in accordance with various embodiments of the technology.
Figure 70:
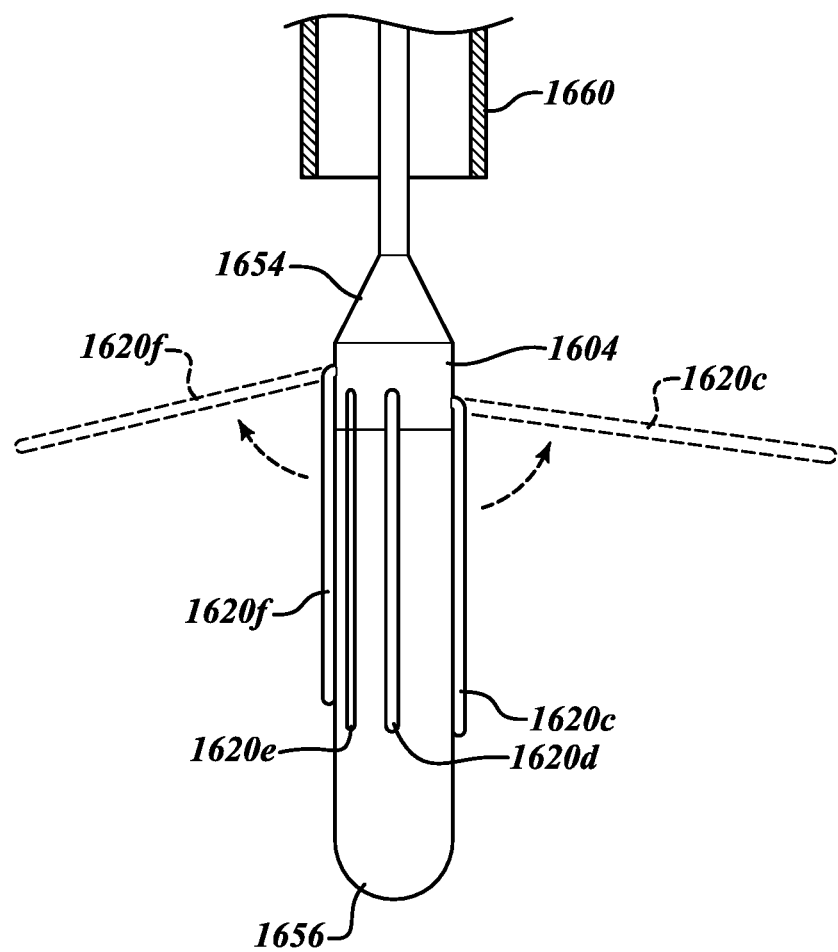
FIG. 70 shows a delivery capsule that has been delivered out of the guide catheter of FIG. 69.

FIG. 69 shows the delivery capsule 1604 positioned in the guide catheter 1660, and FIG. 70 shows the delivery capsule 1604 after delivery out of the guide catheter 1660. Referring first to FIG. 69, the guide catheter 1660 can hold the members 1620 in the delivery state (e.g., a collapsed configuration, an unexpanded configuration, etc.). The delivery capsule 1604 can be moved out of an opening 1666 at an end 1664 of the guide catheter 1660. As the members 1620 exit the end 1664, the members 1620 can moved to the tissue-contacting state (e.g., a deployed configuration, an expanded configuration, etc.).

Referring next to FIG. 70, the members 1620c, 1620f are shown varying between the delivery state (shown in solid line) and the tissue-contacting state (shown in dashed line). The members 1620, for example, can be self-deploying or deployable using deploying devices (e.g., one or more balloons, push rods, etc.). The members 1620 can be coupled to the proximal sheath 1654 via one more joints, pivots, welds, or the like. The dimensions (e.g., lengths, cross-sectional profiles, etc.), composition, and/or number of the members 1620 can be selected based on the location of the treatment site and/or the tissue to be contacted. In the illustrated embodiment, six members 1620 in the form of flexible elongated arms or tines can be made, in whole or in part, of metal, polymers, or other materials suitable to contact tissue of the heart H. In other embodiments, however, the number of members 1620 may vary.

The transverse dimension defined by the members 1620 can be selected to avoid passing the members 1620 through the mitral valve MV. In some embodiments, for example, the transverse diameter may be greater than an inner diameter (e.g., a minimum diameter, a maximum diameter, etc.) defined by the inner region of the annulus 1634 (FIG. 68). The members 1620 can be configured contact opposing sides of the atrial wall.

One method of deploying the prosthetic device 1657 comprises delivering the delivery capsule 1604 through the left atrium LA and into the mitral valve MV. In particular, the members 1620 of the delivery capsule 1604 can be moved to the tissue-contacting state of FIG. 68. The members 1620 positioned to contact the tissue of the annulus 1634 may be less compliant than the tissue of the leaflets. Thus, when the members 1620 contact heart tissue on the atrial side of the annulus 1634, the members 1620 can prevent or limit movement of the delivery capsule 1604 in the distal or downstream direction. A tip 1621f of the member 1620f can be deformed to prevent damage or trauma to the atrial wall AW. In some procedures, the catheter body 1602 can apply a distally or downstream directed force to the delivery capsule 1604 to keep the members 1620 seated on the annulus 1634 while the delivery capsule 1604 deploys the prosthetic device 1657. In some embodiments, the members 1620 can also be configured to contact the leaflet bases 1640, 1644 of the anterior and posterior leaflets AL, PL, respectively. The distal sheath 1656 can be advanced distally into the left ventricle LV while the members 1620 substantially prevent distal movement of the proximal sheath 1654. After the prosthetic device 1657 has been deployed, the catheter can be pulled proximally and removed from the subject. The delivery capsule 1604 can also be used in trans-apical approaches.

Figure 71:
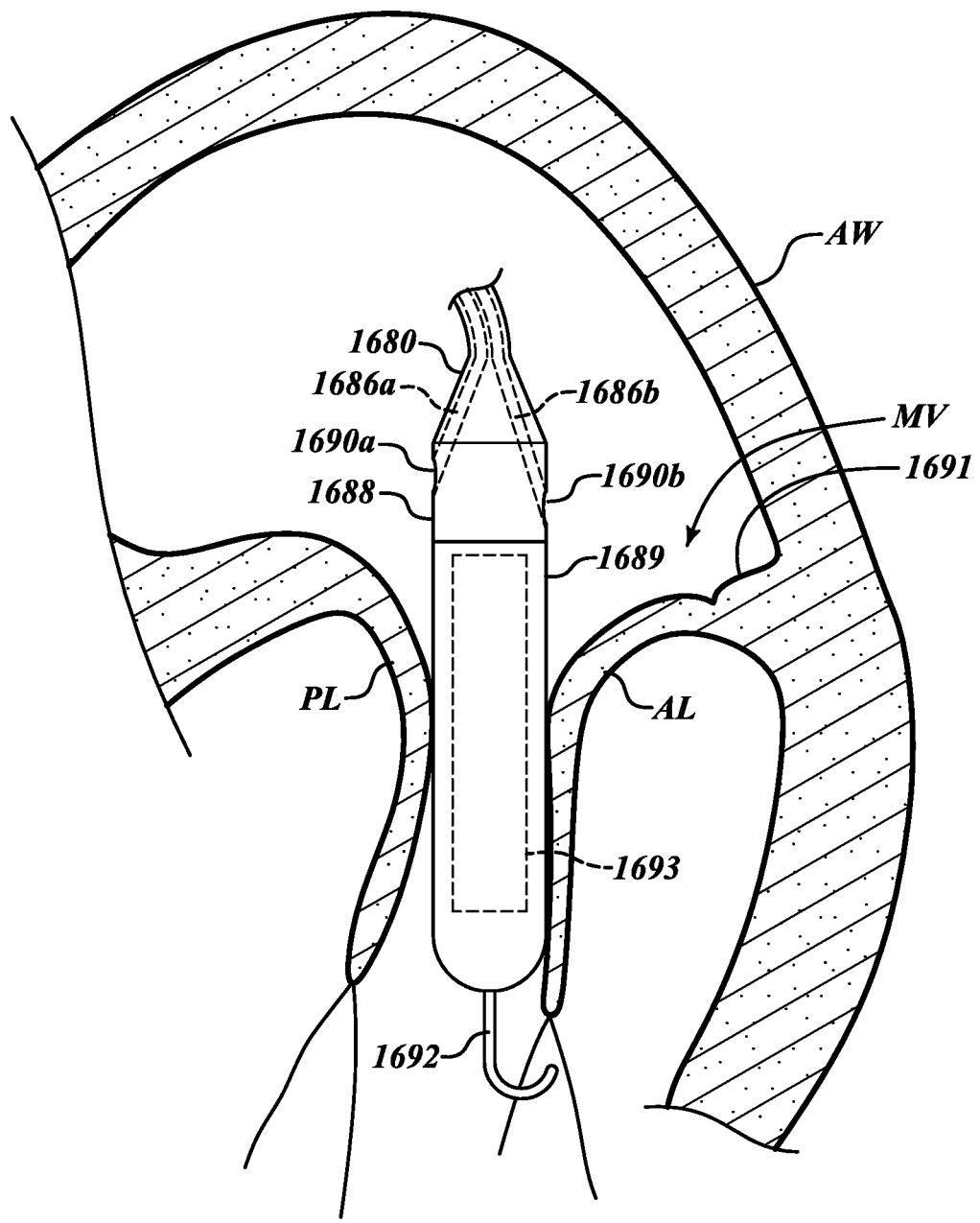
FIG. 71 is a schematic cross-sectional illustration of the heart and a distal portion of a catheter positioned in a mitral valve in accordance with another embodiment of the technology.
Figure 72:
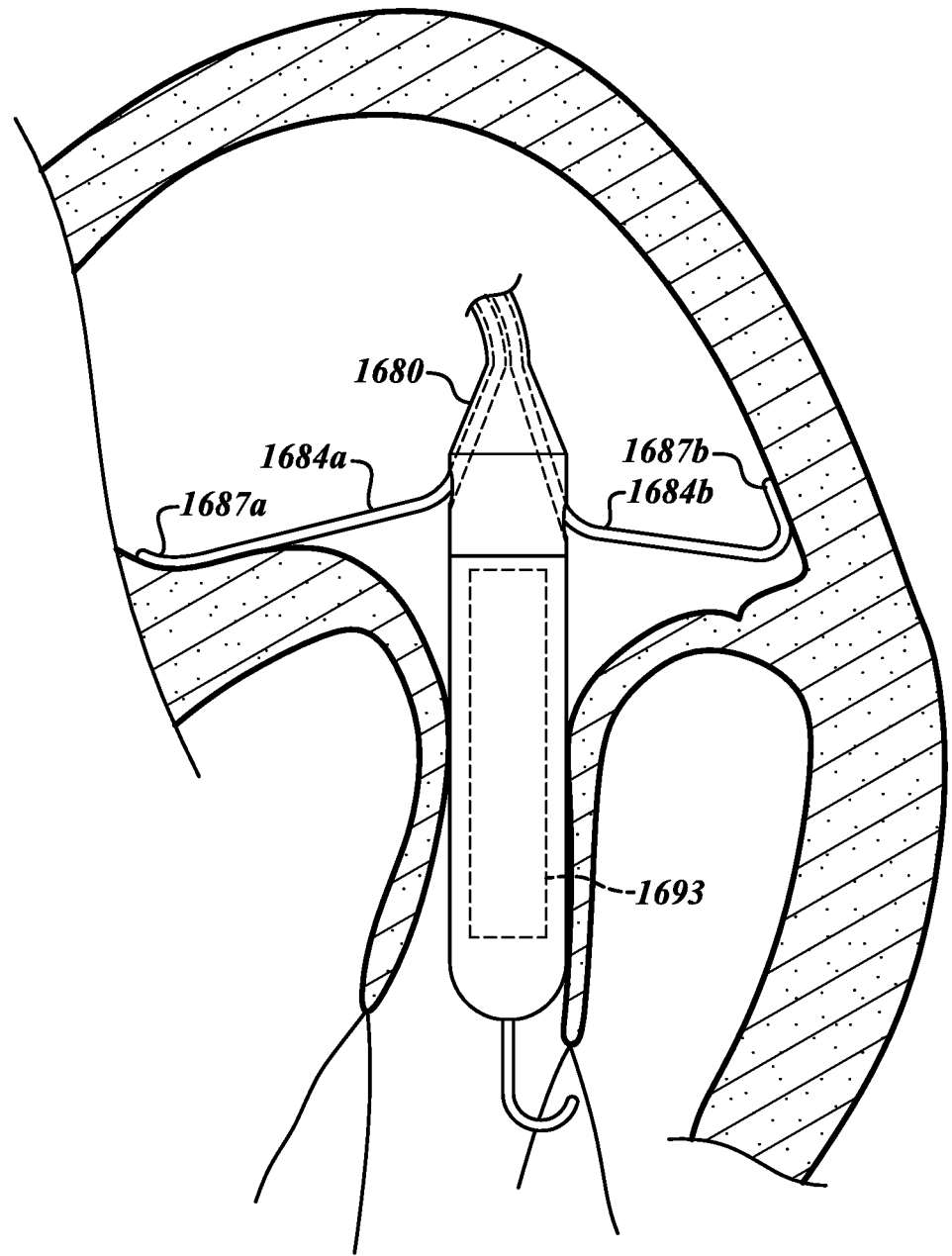
FIG. 72 shows deployed positioners of the distal portion of FIG. 71 contacting the heart.

FIG. 71 shows a delivery capsule 1680 positioned in a mitral valve MV, and FIG. 72 shows positioners in the form of deployable members 1684a, 1684b (collectively "members 1684"). Referring to FIGS. 71 and 72 together, the delivery capsule 1680 can include a cover 1688 and a sheath 1689. The members 1684 can be moved distally through passageways 1686a, 1686b and out of corresponding openings 1690a, 1690b. In some embodiments, the members 1684 can be manually pushed through the passageways 1686a, 1686b. In other embodiments, however, the members 1684 can be move using, for example, an advancing device (e.g., a motorized pusher assembly, an actuator, etc.). The members 1684 can have atraumatic tips 1687a, 1687b (FIG. 72) with pre-formed curved configurations, blunted end, or the like. Additionally or alternatively, the tips 1687a, 1687b can be made of a highly compliant material that deforms to prevent or limit injury or trauma to the tissue of the heart.

As best seen in FIG. 71, the delivery capsule 1680 can be delivered over a guidewire 1692 and into the mitral valve MV. The sheath 1689, for example, can be positioned between the posterior leaflet PL and the anterior leaflet AL. The openings 1690a, 1690b are positioned superiorly of the contact interface between the leaflets PL, AL and the sheath 1689. The members 1684a, 1684b can be moved until the tips 1687a, 1687b contact the heart wall and/or tissue of the annulus 1691. A distal force can be applied to press the members 1684a, 1684b against the annulus 1691, thereby seating the members 1684. In some embodiments, a slight pressure can be continually applied to hold the delivery capsule 1680 in a seated position. The prosthetic device 1693 can be deployed while maintaining its longitudinal position relative to the mitral valve MV. The members 1684a, 1684b can be held against the annulus 1691 to prevent movement of the prosthetic device 1693 in a superior-inferior direction while the prosthetic device 1693 is deployed.

Positioner assemblies of FIGS. 67 and 68 and FIGS. 71 and 72 can also be used in transapical approaches. By way of example, the delivery capsule 1604 of FIGS. 67 and 68 can be delivered into the mitral valve MV via the left ventricle LV, and the members 1620 can be configured to be seated on the ventricular side of the annulus 1634 defining the left ventricle LV. The members 1620 can be positioned on distal or atrial end of delivery capsule 1604. Other positions and configurations of the members 1620 can also be used.

Figure 73:
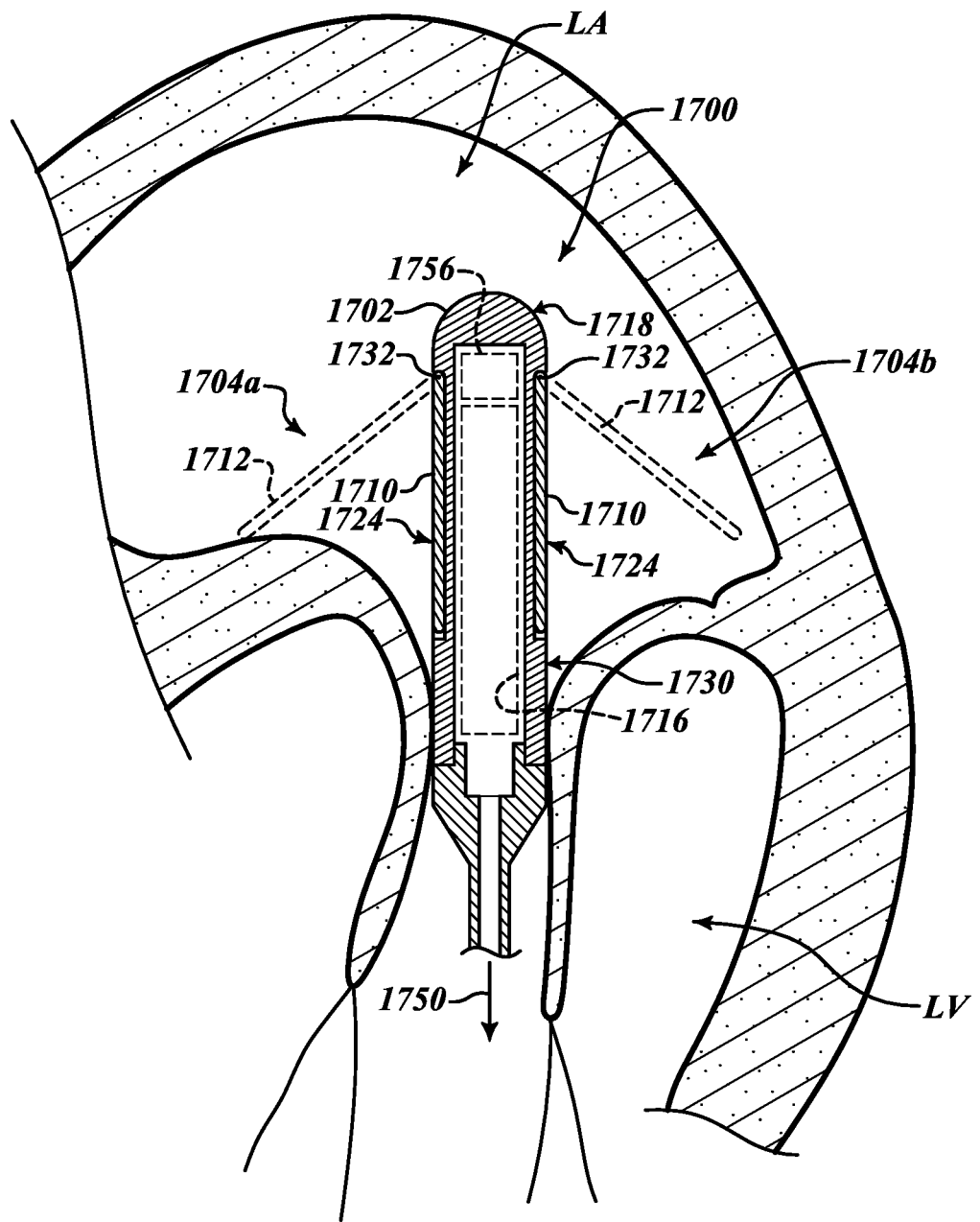
FIGS. 73 and 74 are a series of views of a method of positioning a distal portion of a catheter using a transapical approach in accordance with various embodiments of the technology.
Figure 74:
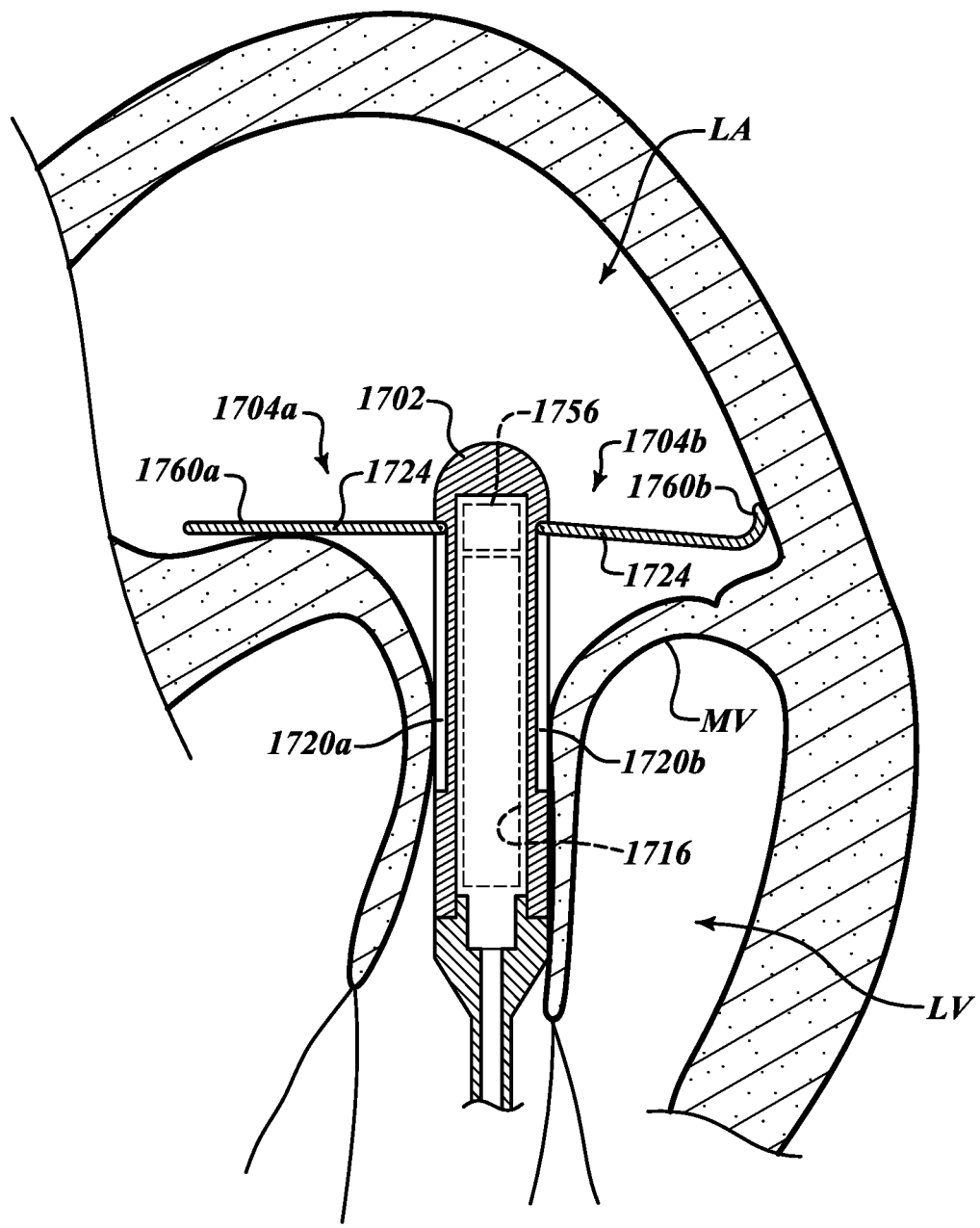

FIGS. 73 and 74 illustrate a method of positioning a distal portion of a catheter using a transapical approach in accordance with additional embodiments of the technology. Referring to FIG. 73, for example, a delivery capsule 1700 is ready to be seated in a mitral valve MV and includes a hydraulically actuatable sheath 1702 and a positioner assembly in the form of deployable members 1704a, 1704b (collectively "members 1704") rotatably coupled to the sheath 1702. The members 1704 can be moved from an undeployed state or a delivery state 1710 to a deployed state 1712 (shown in dashed line). In this embodiment, the outer surfaces 1724 of the members 1704 in the undeployed state or delivery state are configured to be generally flush with the exterior surface 1730 of the main body 1718. The sheath 1702 can include a main body 1718 and receiving features 1720a, 1720b (FIG. 74). The receiving features 1720 may comprise, without limitation, recesses, slots, or other features capable of at least partially receiving the respective members 1704.

FIG. 73 shows pins 1732 pivotally coupling the members 1704 to a main body 1718. Biasing members or push rods can urge the members 1704 outwardly. Tethers coupled to the members 1704 can be used to control movement of the members 1704 towards the deployed position 1712. In some embodiments, tethers can be used to hold the members 1704 in the undeployed positions 1710. When the tethers are lengthened, biasing devices move the members 1704 to the deployed positions 1712. In other embodiments, however, flexible members can couple the members 1704 to the main body 1711.

A transapical approach can be used with the delivery capsule 1700. The delivery capsule 1700 can be into the mitral valve MV via the left ventricle LV. After proximal ends of the members 1704 have cleared the mitral valve MV, the members 1704 can be moved to the deployed state 1712.

After deploying the members 1704, the delivery capsule 1700 can be moved proximally, as indicated by arrow 1750 of FIG. 73. FIG. 74, for example, shows members 1704 having tissue-contacting tips 1760a, 1760b (collectively "tips 1760") contacting the cardiac tissue. The members 1704 can be made, in whole or in part, of radiopaque material or may comprise one or more radiopaque markers and can be viewed under fluoroscopy. In some embodiments, tips 1760 can carry radiopaque markers used to locate anatomical features of interest. After deploying the prosthetic device 1716 using a piston device 1756, the members 1704 can be returned to the undeployed positions 1710. The delivery capsule 1700 can then be removed from the heart.

The catheters disclosed herein can also include other types of positioning features. In some embodiments, for example, a delivery capsule can have an asymmetrical profile. When the delivery capsule is rotated, the profile of the delivery capsule can be used to determine its orientation. For example, a radiopaque sheath can have asymmetrical shape. Under fluoroscopy, the viewable profile of the sheath can be used to determine the rotational position of the delivery capsule. Mechanical position indicators can include, without limitation, one or more push rods, deployable arms, or other types of positioner assemblies. In some embodiments, both fluid position indicators and mechanical position indictors can be used.

Figure 75:
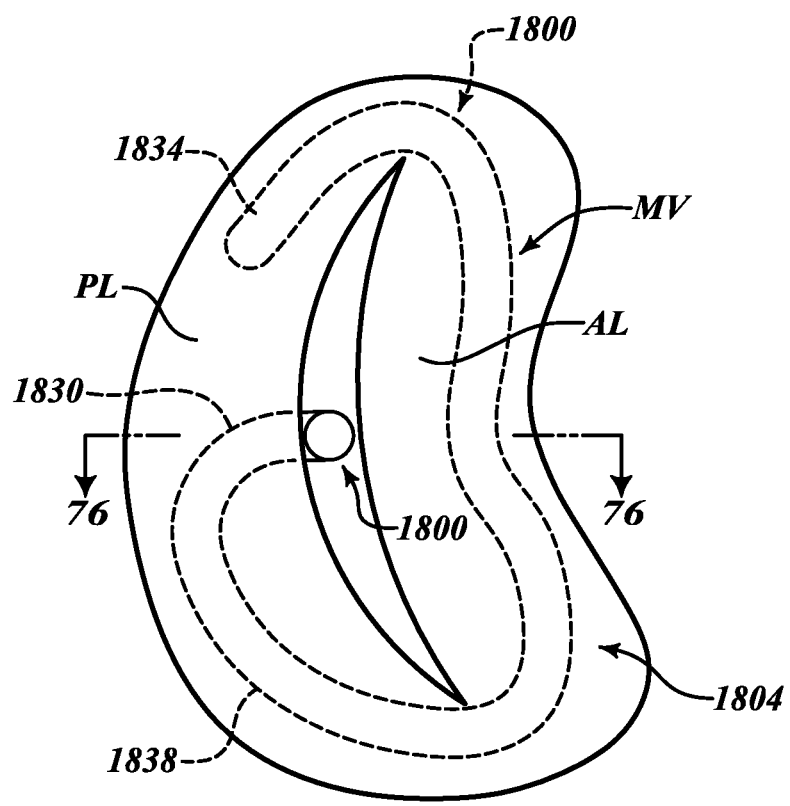
FIG. 75 is a top view of a valve locator engaging a native mitral valve in accordance with various embodiments of the technology.
Figure 76:
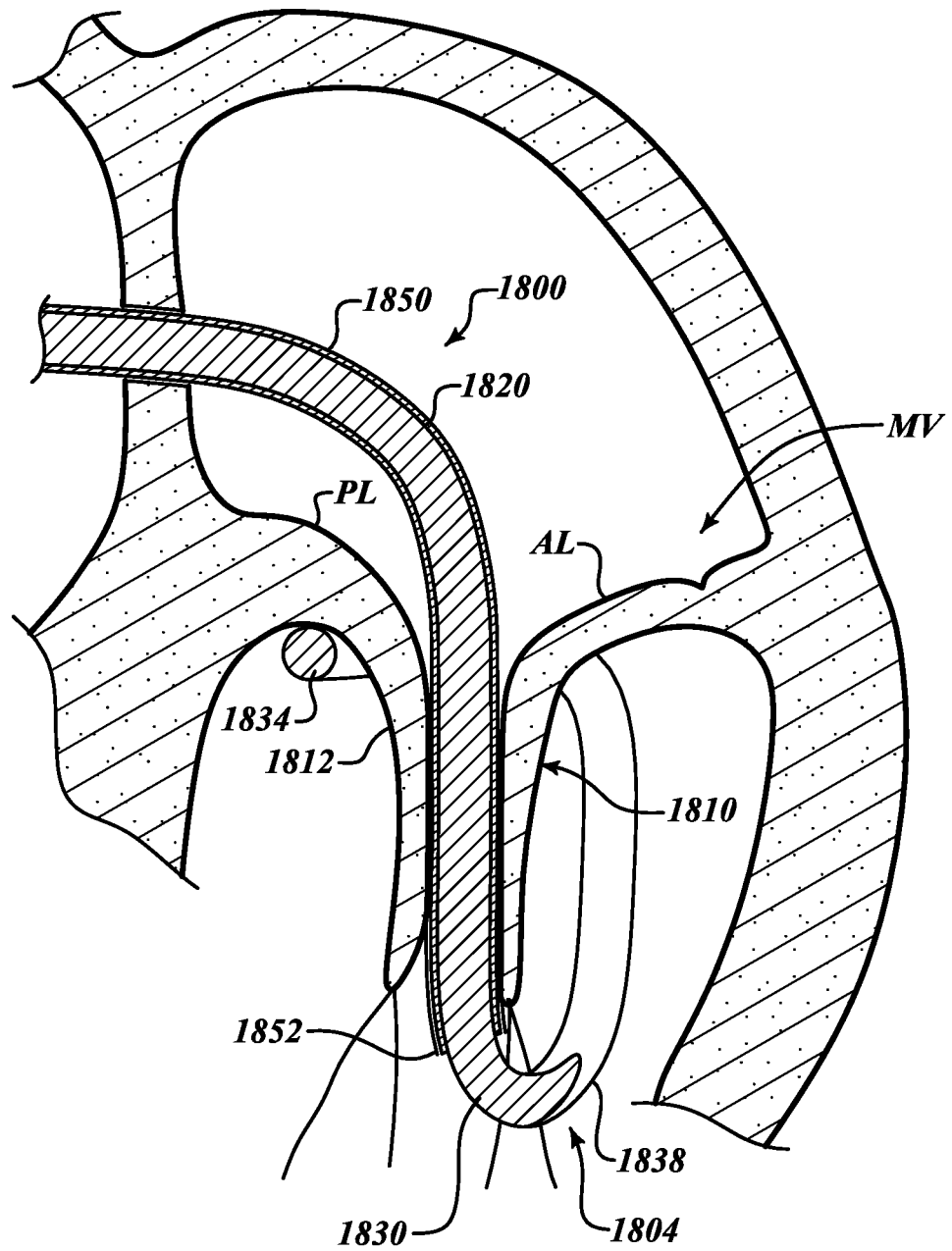
FIG. 76 is a schematic cross-sectional illustration of the heart and the valve locator taken along line 76-76 of FIG. 75.

Locators can be used to locate anatomical features, position delivery capsules, or otherwise identify features of interest. FIGS. 75 and 76, for example, show a locator in the form of valve locator 1800 configured to identify the location of leaflets AL, PL of the mitral valve MV. The valve locator 1800 in a viewing configuration can include a visualization feature 1804 that contacts the inferior surfaces 1810, 1812 (FIG. 76) of the anterior and posterior leaflets AL, PL, respectively.

The valve locator 1800 can include a shaft 1820 and the visualization feature 1804. In some embodiments, the valve locator 1800 is made of highly conformable material to prevent damaging tissue while the visualization feature 1804 is moved to the illustrated position. The shaft 1820 can be made, in whole or in part, of metal, a polymer, an elastomer and can be flexible to navigate along a delivery path. The visualization feature 1804 can include a proximal portion 1830, a distal end or portion 1834, and a main body 1838. The proximal portion 1830 is connected to the shaft 1820. The main body 1838 can be configured to wrap about the anterior and posterior leaflets AL, PL.

The visualization feature 1804 can be made, in whole or in part, of a visualizable material. In embodiments where visualization comprises fluoroscopy, for example, the visualization feature 1804 can be made, in whole or in part, of a radiopaque material. Other types of materials can be used for other types of visualization techniques. The visualization feature 1804 can also be made, in whole or in part, of a shape memory material, such as nickel-titanium (e.g., nitinol), shape memory plastic or polymers, copper-nickel-aluminum alloy, or the like so as to assume a desired shape in an unconstrained condition. In some embodiment, the shape memory material can have one or more shape-transition temperatures. When the temperature of the shape memory material reaches a shape-transition temperature, the visualization feature 1804 can assume a preset configuration. In some embodiments, the visualization feature 1804 can change shapes when the warm blood warms the visualization feature 1804. Additionally or alternatively, a fluid (e.g., a warm or hot fluid), heaters (e.g., resistive heaters, Peltier devices, etc.), or other types of active heating elements can be used to change the temperature of the visualization feature 1804. In non-shape memory embodiments, the visualization feature 1804 can be made, in whole or in part, of metals (e.g., steel, titanium, aluminum, etc.), polymers (e.g., conductive polymers), or other resilient materials. For example, the delivery sheath 1850 of FIG. 76 can be made of rigid plastic. As the visualization feature 1804 is delivered out of an end 1852 of the delivery sheath 1850, the visualization feature 1804 can assume the delivered configuration.

After positioning the visualization feature 1804 on the inferior side of the mitral valve MV, the delivery sheath 1850 can be pulled proximally to expose the visualization feature 1804 and allow it to assume its unconstrained shape. Shaft 1820 is then retracted to move the visualization feature 1804 against the anterior and posterior leaflets AL, PL. The main body 1838 can extend posteriorly from the proximal portion of 1830 and wraps around the intersection of the posterior leaflet and the anterior leaflet as shown in FIG. 75. Of course, various other shapes may be used which will seat in a known position relative to the native anatomy to provide a reference to guide the positioning of the prosthetic device.

With a slight pressure applied to leaflets, a physician can view the position of the base of the leaflets AL, PL. In some embodiments, the visualization feature 1804 is configured to engage the junction of the anterior and posterior leaflets and the annulus. The physician can thus identify the location of the annulas and other anatomical features of the mitral valve based, at least in part, on the position of the position feature 1804.

Valve locator 1800 can be used in combination with the catheters disclosed herein. For example, the valve locator 1800 can serve as a guidewire that is delivered into the heart. After positioning the valve locator 1800, the delivery capsule can be moved over the valve locator 1800. Other types of visualization locators can also be used. In transapical approaches, a visualization locator can be delivered through the left ventricle, through an opening the mitral valve, and into the left atrium. The visualization locator can be deployed to engage the annulus, the junction between the leaflets and the annulus, or other features of interest.

The embodiments of catheters, catheter components, prosthetic devices, and associated methods disclosed herein can be mixed and matched based on, for example, the procedure to be performed. It will be appreciated, for example, that specific elements, substructures, advantages, uses, and/or other features of the different embodiments can be suitably interchanged, substituted or otherwise configured with one another. For example, the mechanical position indicators discussed in connection with FIGS. 44-56 can be incorporated into the catheters and/or delivery capsules discussed in connection with FIGS. 2A-43. By way of another example, the fluid position indicators discussed in connection with FIGS. 57-65 can be incorporated into the delivery capsules discussed in connection with FIGS. 2A-43. The orientation evaluation process can involve, without limitation, determination of (1) relative position(s) between one or more features of a catheter and the target site, (2) relative position(s) between one or more features of a catheter and a prosthetic device, and (3) absolute position(s) of one or more features of a catheter and/or prosthetic device.

The target delivery sites can be at different location within a subject. The embodiments disclosed herein can be used to deliver devices to target delivery sites in the vascular system, respiratory system, digestive system, or other systems of a patient. In the vascular system, the target delivery sites can be with in the heart, arteries, or the like. Within the heart, any of the native valves may be targeted, including the mitral, aortic, or tricuspid valve. Target delivery sites in the respiratory system can be within the trachea, lungs, or the like. Target delivery sites in the digestive system can be located along the stomach, colon, intestines, etc. The prosthetic devices can be selected based on the location target delivery site. The prosthetic devices can be, without limitation, self-expanding devices, non-self-expanding devices (e.g., devices expandable via a balloon), stents (e.g., self-expanding stents, balloon expanding stents, coronary stents, ureteral stents, prostatic stents, aneurysm stents, peripheral stents, tracheobronchial stents, etc.), grafts (e.g., self-expanding grafts, intraluminal grafts, etc.), occlusion devices (e.g., septal device occlusion devices, patent foramen ovale occlusion devices, etc.), valves (e.g., one-way valves, duckbill valves, check valves, valves with leaflets or flaps, etc.), implants (e.g., micro-pumps, implantable electrodes, etc.), or the like.

Figure 77:
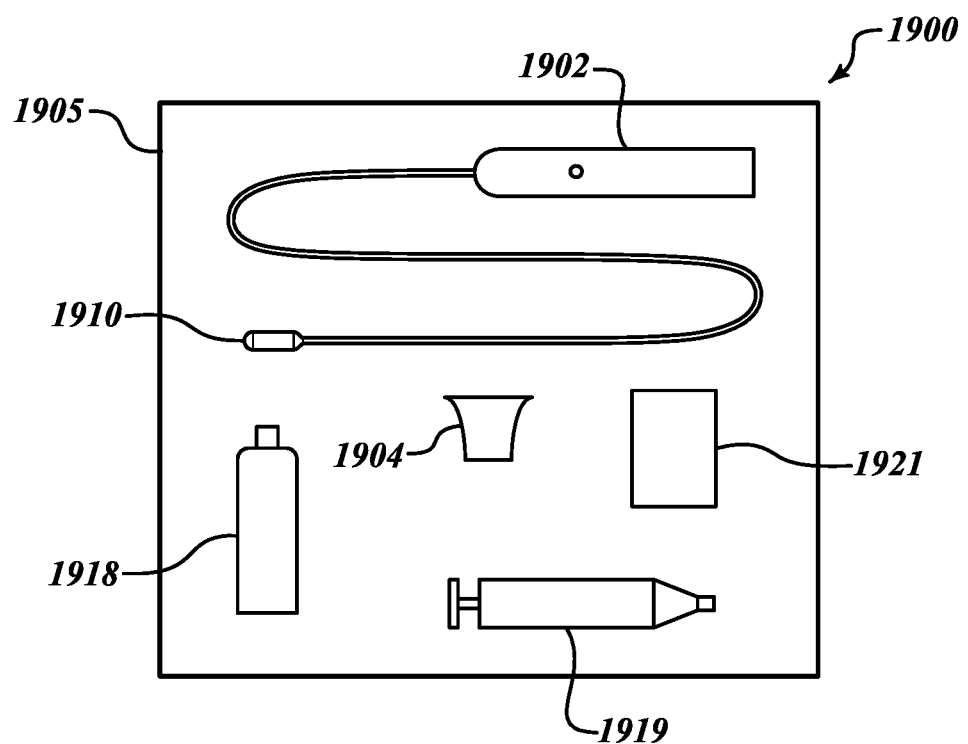
FIG. 77 is a top view of a kit for delivering devices into a patient in accordance with various embodiments of the technology.

FIG. 77 shows a kit 1900 that can include a catheter 1902, a device 1904, and packaging 1905. The catheter 1902, for example, can be any of the catheters discussed herein. The device 1904 can be a prosthetic device loadable into a delivery capsule 1910 of the catheter 1902. In some embodiments, the kit 1900 can include an array of prosthetic devices. A physician can select one of the prosthetic devices based on, for example, the anatomy of the subject. The packaging 1905 can be sterilized packaging that includes, for example, a tray, a bag, a pouch, and/or the like.

The kit 1900 can further include a container 1918 and instructions for use 1921. The container 1918 can hold packing substance (e.g., a gel, a flowable substance, a fluid, etc.). For example, the packing substance can be a lubricant that reduces or limits friction between the device 1904 and the delivery capsule 1910. A syringe 1919 can be used to deliver the packing substance into the delivery capsule 1910. In some procedures, the packing substance can be delivered onto the device 1904 prior to loading the device 1904 into the delivery capsule 1910. In other procedures, the packing substance is delivered onto surfaces of the delivery capsule 1910 before, during, and/or after loading the device 1904. In other embodiments, the kit 1900 may have a different arrangement and/or include different features. The instructions for use may include instructions for the use of the catheter 1902 and device 1904. In preferred embodiments, the instructions will comprise instructions for implanting the prosthetic device in the heart to repair or replace a native heart valve in accordance with the methods described elsewhere herein.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. As provided above, the present application incorporates the subject matter in (1) International PCT Patent Application No. PCT/US2012/043636, entitled "PROSTHETIC HEART VALVE DEVICES AND ASSOCIATED SYSTEMS AND METHODS," filed on Jun. 21, 2012; (2) U.S. Provisional Patent Application No. 61/549,037, entitled "SYSTEM FOR MITRAL VALVE REPLACEMENT," filed on Oct. 19, 2011; (3) International PCT Patent Application No. PCT/US2012/061215, entitled "DEVICES, SYSTEMS AND METHODS FOR HEART VALVE REPLACEMENT," filed on Oct. 19, 2012, and (4) U.S. Provisional Patent Application No. 61/605,699, entitled "SYSTEM FOR MITRAL VALVE REPLACEMENT," filed on Mar. 1, 2012. Each of these applications is incorporated herein by reference in its entirety.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A delivery system comprising:
    a catheter body having a distal portion and a proximal portion;
    a control unit coupled to the proximal portion of the catheter body;
    a delivery capsule coupled to the distal portion of the catheter body, the delivery capsule being a split capsule including a proximal capsule having an open distal end and a distal capsule having an open proximal end, wherein in a containment configuration, the proximal capsule is configured to house a first portion of a prosthetic heart valve therein and the distal capsule is configured to house a second portion of the prosthetic heart valve therein; and
    a fluid chamber disposed within the distal capsule, wherein the distal capsule is configured to be driven axially towards a deployment configuration to uncover the second portion of the prosthetic valve when fluid is delivered to the fluid chamber,
    wherein the fluid chamber is distal of a piston device disposed within the distal capsule, wherein the distal capsule is configured to be driven axially distally towards the deployment configuration to uncover the second portion of the prosthetic valve when fluid is delivered to the fluid chamber.

2. The delivery system of claim 1, further comprising a lock, wherein with the lock in a locked configuration, axial translation at least a portion of the delivery capsule is prevented and with the lock in an unlocked configuration, axial translation of the at least a portion of the delivery capsule is enabled.

3. The system of claim 1, wherein the piston device includes a head positioned within the distal capsule when the distal capsule is in the containment configuration, wherein the head is configured to translationally restrain an end of the prosthetic heart valve device such that the prosthetic heart valve device is held substantially stationary relative to the catheter body and a native annulus surrounding leaflets of a valve of the heart as the distal capsule is driven axially to unsheathe the prosthetic heart valve device.

4. A delivery system comprising:
    a catheter body having a distal portion and a proximal portion;
    a control unit coupled to the proximal portion of the catheter body;
    a delivery capsule coupled to the distal portion of the catheter body, the delivery capsule being configured to house a prosthetic heart valve therein, the delivery capsule being axially translatable to uncover the prosthetic heart valve, wherein the delivery capsule includes:
        a containment chamber configured to restrain at least a portion of the prosthetic heart valve device with the delivery capsule in a containment configuration; and
        a fluid chamber, wherein the delivery capsule is configured to be driven axially towards a deployment configuration when fluid is delivered to the fluid chamber; and
    a piston device positioned within the delivery capsule, the piston device and the delivery capsule defining the fluid chamber.

5. The system of claim 4, wherein the delivery capsule has a closed distal end and an open proximal end, wherein the open proximal end is configured to release the prosthetic heart valve device therethrough.

6. The system of claim 5, further comprising a prosthetic heart valve device positioned within the delivery capsule such that in the containment configuration a proximal portion of the prosthetic heart valve device is not disposed within the delivery capsule.

7. The system of claim 6, wherein the proximal portion of the prosthetic heart valve device is configured to be deployed and engage with heart tissue before the housing is driven to release the prosthetic heart valve device from the delivery capsule to anchor the prosthetic heart valve device to a native heart valve.

8. The system of claim 6, wherein the proximal portion of the prosthetic heart valve device is a brim.

9. The system of claim 4, further comprising a biasing device configured to urge at least a portion of the delivery capsule towards the containment configuration when the delivery capsule is driven from the containment configuration towards the deployment configuration.

10. The system of claim 4, further comprising a restraining mechanism configured to provide a resisting force opposing movement of the delivery capsule towards the deployment configuration.

11. The system of claim 10, wherein the piston device includes a head having a hub, wherein the restraining mechanism comprises a tether having a distal end coupled to the housing and a proximal portion at least partially wrapped around the hub of the head of the piston device.

12. A delivery system comprising:
a catheter body having a distal portion and a proximal portion;
a control unit coupled to the proximal portion of the catheter body;
a delivery capsule coupled to the distal portion of the catheter body, the delivery capsule being configured to house a prosthetic heart valve therein, the delivery capsule being axially translatable to uncover the prosthetic heart valve, the delivery capsule including, a containment chamber configured to restrain at least a portion of the prosthetic heart valve device with the delivery capsule in a containment configuration, and a fluid chamber, wherein the delivery capsule is configured to be driven axially towards a deployment configuration when fluid is delivered to the fluid chamber; and
a lock coupled to the control unit, wherein the lock is configured to prevent axial translation of at least a portion of the capsule with the lock in a locked configuration, wherein the lock comprises a plunger.

13. The delivery system of claim 12, further comprising a biasing device configured to urge at least a portion of the delivery capsule towards the containment configuration when the delivery capsule is driven from the containment configuration towards the deployment configuration.

14. The system of claim 12, further comprising a restraining mechanism configured to provide a resisting force opposing movement of the delivery capsule towards the deployment configuration.

15. The system of claim 14, further comprising a piston device positioned within the delivery capsule, the piston device and the delivery capsule defining the fluid chamber, the piston device including a head having a hub, wherein the restraining mechanism comprises a tether having a distal end coupled to the housing and a proximal portion at least partially wrapped around the hub of the head of the piston device.

16. The system of claim 1, wherein the proximal capsule is configured to be translated axially mechanically and the distal capsule is configured to be translated axially hydraulically.

17. The system of claim 1, further comprising a second fluid chamber disposed within the proximal capsule such that when fluid is delivered to the second fluid chamber the proximal capsule is driven axially proximally towards the deployment configuration to uncover the first portion of the prosthetic valve.

* * * * *